US012559768B2

(12) United States Patent
Simon et al.

(10) Patent No.: US 12,559,768 B2
(45) Date of Patent: *Feb. 24, 2026

(54) PLANT VECTORS, COMPOSITIONS AND USES RELATING THERETO

(71) Applicants:University of Maryland, College Park, College Park, MD (US); The Regents of the University of California, Oakland, CA (US)

(72) Inventors: Anne Elizabeth Simon, Upper Marlboro, MD (US); Jingyuan Liu, College Park, MD (US); Georgios Vidalakis, Riverside, CA (US); Sohrab Bodaghi, Laguna Niguel, CA (US)

(73) Assignees: UNIVERSITY OF MARYLAND, COLLEGE PARK, College Park, MD (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 627 days.

This patent is subject to a terminal disclaimer.

(21) Appl. No.: 17/775,822

(22) PCT Filed: Nov. 12, 2020

(86) PCT No.: PCT/US2020/060228
§ 371 (c)(1),
(2) Date: May 10, 2022

(87) PCT Pub. No.: WO2021/097086
PCT Pub. Date: May 20, 2021

(65) Prior Publication Data
US 2024/0279675 A1     Aug. 22, 2024

(51) Int. Cl.
*C12N 15/82*     (2006.01)
(52) U.S. Cl.
CPC ..... *C12N 15/8281* (2013.01); *C12N 15/8218* (2013.01)
(58) Field of Classification Search
None
See application file for complete search history.

(56) References Cited

U.S. PATENT DOCUMENTS

| | | | |
|---|---|---|---|
| 5,304,731 | A | 4/1994 | Masuta et al. |
| 7,217,854 | B1 | 5/2007 | Baulcomb et al. |
| 8,389,804 | B2 | 3/2013 | Dawson et al. |
| 2006/0127364 | A1 | 6/2006 | Christian et al. |
| 2010/0017911 | A1 | 1/2010 | Dawson et al. |
| 2011/0288147 | A1 | 11/2011 | Brown |
| 2013/0212739 | A1 | 8/2013 | Giritch et al. |
| 2014/0296503 | A1 | 10/2014 | Avniel et al. |
| 2015/0096078 | A1 | 4/2015 | Dawson et al. |
| 2015/0315604 | A1 | 11/2015 | Giritch et al. |
| 2017/0044560 | A1 | 2/2017 | Paldi et al. |

| | | | | |
|---|---|---|---|---|
| 2018/0002682 | A1 | 1/2018 | Sternberg et al. | |
| 2018/0235210 | A1 | 8/2018 | Zeng et al. | |
| 2019/0093117 | A1 | 3/2019 | Li et al. | |
| 2021/0130837 | A1* | 5/2021 | Simon | C12N 15/8243 |
| 2021/0324394 | A1 | 10/2021 | Navarro et al. | |
| 2021/0355499 | A1* | 11/2021 | Simon | C12N 15/67 |
| 2022/0002746 | A1* | 1/2022 | Simon | C12N 15/8281 |
| 2024/0002871 | A1* | 1/2024 | Simon | C12N 15/8249 |
| 2024/0381876 | A1* | 11/2024 | Simon | C12N 15/86 |

FOREIGN PATENT DOCUMENTS

| | | | |
|---|---|---|---|
| AU | 2016238902 | B2 | 11/2018 |
| BR | 112015027022 | A2 | 9/2017 |
| CN | 105567728 | A | 5/2016 |
| CN | 115052979 | A | 9/2022 |
| JP | 2007-518412 | A | 7/2007 |
| JP | 2011-015640 | A | 1/2011 |
| JP | 2013-532992 | A | 8/2013 |
| JP | 2016-514465 | A | 5/2016 |
| WO | 0005379 | A1 | 2/2000 |
| WO | 2003087146 | A2 | 10/2003 |
| WO | 2020035619 | A1 | 2/2020 |
| WO | 2020051156 | A1 | 3/2020 |
| WO | 2020102210 | A1 | 5/2020 |
| WO | WO 2020/102210 | | 5/2020 |

OTHER PUBLICATIONS

Aguado, L.C. et al. (2017), *"RNase III nucleases from diverse kingdoms serve as antiviral effectors"*, Nature 547:114-117.
Balachandran, S. et al. (1997), *"Phloem sap proteins from Cucurbita maxima and Ricinus communis have the capacity to traffic cell to cell through plasmodesmata"*, PNAS 94(25):14150-14155.
Barratt et al. (2011), *"Callose Synthase GSL7 Is Necessary for Normal Phloem Transport and Inflorescence Growth in Arabidopsis"*, Plant Physiol 155(1):328-341.
Bendix, C., and Lewis, J.D. (2018), *"The enemy within: phloem-limited pathogens"*, Mo Plant Path 19:238-254.
Cadena-Nava, et al. (2012), *"Self-assembly of viral capsid protein and RNA molecules of different sizes: requirement for a specific high protein/RNA mass ratio"*, J. Virol. 86:3318-3326.
Calderwood, A. et al. (2016), *"Transcript Abundance Explains mRNA Mobility Data in Arabidopsis thaliana"*, Plant Cell 28:610-615.
Chen, X.Y. and Kim, J.Y. (2009), *"Callose synthesis in higher plants"*, Plant Sig Behav 4(6):489-492.
Cheng, et al. (2015), *"Expressing p20 hairpin RNA of Citrus tristeza virus confers Citrus aurantium with tolerance/resistance against stem pitting and seedling yellow CTV strains"*, J. Integrative Agriculture 14(9):1767-1777.
Chin, L.S. et al. (1993), *"The beet western yellows virus ST9-associated RNA shares structural and nucleotide sequence homology with Tombusviruses"*, Virology 192(2):473-482.

(Continued)

*Primary Examiner* — Jason Deveau Rosen

(57) ABSTRACT

The present disclosure relates to a single stranded RNA vector suitable for introducing a therapeutic agent, such as a peptide, a protein or a small RNA, into a host plant. The vector does not encode for any movement protein or coat protein, but is capable of systemic and phloem-limited movement and replication within the host plant.

8 Claims, 46 Drawing Sheets

Specification includes a Sequence Listing.

(56) References Cited

OTHER PUBLICATIONS

Collum, T.D. et al. (2016), "*Tobacco mosaic virus-directed reprogramming of auxin/indole acetic acid protein transcriptional responses enhances virus phloem loading*", Proc Natl Acad Sci USA 113:E2740-E2749.

Deom, C.M. et al. (1987), "*The 30-kilodalton gene product of tobacco mosaic virus potentiates virus movement*", Science (New York, NY) 237:389-394.

Enrique et al. (2011), "*Novel demonstration of RNAi in citrus reveals importance of citrus callose synthase in defense against Xanthomonas citri subsp. Citri*", Plant Biotech J 9:394-407.

Folimonova, S.Y. and Tilsner, J. (2018), "*Hitchhikers, highway tolls and roadworks: the interactions of plant viruses with the phloem*", Curr Opin Plant Biol 43:82-88.

Gao, F. and Simon, A.E. (2017), "*Differential use of 3 ' CITEs by the subgenomic RNA of Pea enation mosaic virus 2*", Virology 510:194-204.

Gaupels, F. et al. (2008), "*Nitric oxide generation in Vicia faba phloem cells reveals them to be sensitive detectors as well as possible systemic transducers of stress signals*", New Phytol 178:634-646.

GenBank Accession JX101610, "*Citrus yellow vein-associated virus isolate YV920, complete genome*", Jul. 31, 2013.

Gómez, G. and Pallás, V. (2004), "*A long-distance translocatable phloem protein from cucumber forms a ribonucleoprotein complex in vivo with Hop stunt viroid RNA*", J Virol 78(18):10104-10110.

Gomez, G. et al. (2005), "*Identification of translocatable RNA-binding phloem proteins from melon, potential components of the long-distance RNA transport system*", Plant J 41:107-116.

Ham, B.K. and Lucas, W.J. (2017), "*Phloem-Mobile RNAs as Systemic Signaling Agents*", Annual Rev Plant Biol 68:173-195.

Ham, B.K. et al. (2009), "*A polypyrimidine tract binding protein, pumpkin RBP50, forms the basis of a phloem-mobile ribonucleoprotein complex*", Plant Cell 21:197-215.

Heinlein, M. (2015), "*Plant virus replication and movement*", Virology 479:657-671.

International Search Report PCT/US2019/060945 (WO 2020/102210) (2020) (5 pages).

International Search Report PCT/US2020/060228 (WO 2021/097086) (2021) (4 pages).

Jia, et al. (2014), "*Xcc-facilitated agroinfiltration of citrus leaves: a tool for rapid functional analysis of transgenes in citrus leaves*", Plant Cell Rep. 33:1993-2001.

Kim, G. et al. (2014), "*Genomic-scale exchange of mRNA between a parasitic plant and its hosts*", Science 345:808-811.

Kim, M. et al. (2001), "*Developmental changes due to long-distance movement of a homeobox fusion transcript in tomato*", Science (New York, NY) 293:287-289.

Koh, H. et al. (2012). "*Silent Information Regulator 2 (Sir2) and Forkhead Box O (FOXO) Complement Mitochondrial Dysfunction and Dopaminergic Neuron Loss in Drosophila PTEN-induced Kinase 1 (PINK1) Null Mutant*", J Biol Chem 287(16):12750-12758.

Lee, J.Y. and Frank, M. (2018), "*Plasmodesmata in phloem: different gateways for different cargoes*", Curr Opin Plant Biol 43:119-124.

May, et al. (2020), "*The Multifunctional Long-Distance Movement Protein of Pea Enation Mosaic Virus 2 Protects Viral and Host Transcripts from Nonsense-Mediated Decay*", mBio 11:300204-20.

Morris, R.J. (2018), "*On the selectivity, specificity and signaling potential of the long-distance movement of messenger RNA*", Curr Opin Plant Biol 43:1-7.

Pallas, V. and Gomez, G. (2013), "*Phloem RNA-binding proteins as potential components of the long-distance RNA transport system*", Front Plant Sci 4:130.

Passmore, B.K. et al. (1993), "*Beet western yellows virus-associated RNA: an independently replicating RNA that stimulates virus accumulation*", PNAS 90(31):10168-10172.

Quito-Avila, D.F. et al. (2015), "*Detection and partial genome sequence of a new umbra-like virus of papaya discovered in Ecuador*", Eur J Plant Pathol 143:199-204.

Ryabov, E.V. et al. (2001), "*Umbravirus-encoded proteins both stabilize heterologous viral RNA and mediate its systemic movement in some plant species*", Virology 288:391-400.

Schoelz, J.E. et al. (2011), "*Intracellular transport of plant viruses: finding the door out of the cell*", Mol Plant 4:813-831.

Senthil-Kumar et al. (2008), "*Virus-induced gene silencing and its application in characterizing genes involved in water-deficit-stress tolerance*", J Plant Physiol 165(13):1404-1421.

Singla-Rastogi, et al. (2019), "*Plant small RNA species direct gene silencing in pathogenic bacteria as well as disease protection*", Preprint posted to bioRxiv (47 pages).

Thieme, C.J. et al. (2015), "*Endogenous Arabidopsis messenger RNAs transported to distant tissues*", Nature Plants 1(4):15025.

Tilsner, J. (2014), "*Techniques for RNA in vivo imaging in plants*", J Microscopy 258(1):1-5.

Turgeon, R. and Wolf, S. (2009), "*Phloem Transport: Cellular Pathways and Molecular Trafficking*", Ann Rev Plant Biol 60:207-221.

Weathers, L. (1957), "*A vein-yellowing disease of citrus caused by a graft-transmissible virus*", Plant Disease Reporter 41:741-742.

Weathers, L.G. (1960), "*Yellow-vein disease of citrus and studies of interactions between yellow-vein and other viruses of citrus*", Virology 11:753-764.

Weathers, L.G. (1963), "*Use of synergy in identification of strain of Citrus yellow vein virus*", Nature 200:812-813.

Written Opinion of the International Searching Authority PCT/US2019/060945 (WO 2020/102210) (2020) (7 pages).

Written Opinion of the International Searching Authority PCT/US2020/060228 (WO 2021/097086) (2021) (7 pages).

Xia, C. et al. (2018), "*Elucidation of the Mechanisms of Long-Distance mRNA Movement in a Nicotiana benthamiana/Tomato Heterograft System*", Plant Physiol 177:745-758.

Xie et al. (2011), "*CalS7 encodes a callose synthase responsible for callose deposition in the phloem*", Plant J 65(1):1-14.

Xoconostle-Cazares, B. et al. (1999), "*Plant paralog to viral movement protein that potentiates transport of mRNA into the phloem*", Science (New York, NY) 283:94-98.

Yang, Y. et al. (2015), "*Messenger RNA exchange between scions and rootstocks in grafted grapevines*", BMC Plant Biol 15, 251.

Yoo, B.C. et al. (2004), "*A systemic small RNA signaling system in plants*", Plant Cell 16:1979-2000.

Zhang, W.N. et al. (2016), "*tRNA-Related Sequences Trigger Systemic mRNA Transport in Plants*", Plant Cell 28:1237-1249.

Japanese Patent Application No. 2021-549930, Office Action dated Oct. 17, 2023.

Indonesian Patent Application No. P00202104029, Office Action dated Dec. 13, 2022.

European Patent Application No. 19884145.4, Extended European Search Report dated Jul. 21, 2022.

Zaidi, S. et al., "Viral Vectors for Plant Genome Engineering", Frontiers in Plant Science, vol. 8, Apr. 11, 2017, pp. 1-6.

Hefferon, K. "Plant Virus Expression Vector Development: New Perspectives", Biomed Research International, vol. 2014, Jan. 1, 2014. pages 1-6.

Kwon, S. et al., "Complete Nucleotide Sequence, Genome Organization, and Comparative Genomic Analyses of Citrus Yellow-Vein Associated Virus (CYVaV)", Frontiers in Microbiology, vol. 12, Jun. 8, 2021, pp. 1-12.

Chilean Patent Application No. 01254-2021, Office Action dated May 19, 2023.

Duan et al., "Complete genome sequence of citrus huanglongbing bacterium, 'Candidatus Liberibacter asiaticus' obtained through metagenomics," Molecular Plant-Microbe Interactions, 22(8), 1011-1020, 2009.

Luck et al., "siRNA-Finder (si-Fi) software for RNAi-target design and off-target prediction", Frontiers in Plant Science, 10, 1023, 2019.

Oxford learner's dictionary meaning of word "effective". https://www.oxfordlearnersdictionaries.com/definition/english/effective. (accessed May 18, 2023).

(56)             References Cited

OTHER PUBLICATIONS

U.S. Appl. No. 17/317,596, Restriction Requirement dated Jan. 4, 2023.
U.S. Appl. No. 17/317,596, Office Action dated May 24, 2023.
U.S. Appl. No. 17/317,596, Final Office Action dated Jan. 12, 2024.
European Patent Application No. 20886307.6, Supplementary Partial European Search Report dated Dec. 14, 2023.
Fagoaga, Carmen et al., "Post-Transcriptional Gene Silencing of the p23 Silencing Suppressor of Citrus tristeza virus Confers Resistance to the Virus in Transgenic Mexican Lime", Plant Molecular Biology, vol. 60, No. 2, Jan. 1, 2006, pp. 153-165.
Thomas et al., 2003, Turnip crinkle virus coat protein mediates suppression of RNA silencing in Nicotiana benthamiana. Virology, 306(1), 33-41. (Year: 2003).
Kappagantu et al., 2020, Viral hacks of the plant vasculature: the role of phloem alterations in systemic virus infection. Annual review of virology, 7, 351-370. (Year: 2020).
Liu et al., 2021, Translation and Movement of an Infectious Umbravirus-like RNA Citrus Yellow Vein Associated Virus (Doctoral dissertation, University of Maryland, College Park). (Year: 2021) (Year: 2021).
European Patent Application No. 20886307.6, Extended European Search Report dated Mar. 6, 2024.
Chilean Patent Application No. 01254-2021, Office Action dated Feb. 16, 2024.
Japanese Patent Application No. 2021-549930, Office Action dated Jun. 14, 2024.
Chinese Patent Application No. 202080093354.9, Office Action dated Jun. 28, 2024.
Yao Lixiao et al., "Advances and strategies in citrus genetic engineering and breeding", Journal of Fruit Science, vol. 30, No. 6, Nov. 10, 2013, pp. 1056-1064.

Abdelhalek et al., 2018, A comparative analysis of the suppressor activity of Tobacco mosaic virus proteins in the tomato plant. Jordan J Biol Sci Short Commun, 11(4), 469-473. (Year: 2018).
Liu Qiyan, "Molecular identification and comparative genomic study of four closteroviruses isolated from wild citrus", China Master's Theses Full-text Database (Electronic Journal), Collection of Agricultural Science and Technology, Jan. 15, 2022, pp. 1-69.
Park et al., 2017, The use of a tobacco mosaic virus-based expression vector system in chrysanthemum. The Plant Pathology Journal, 33(4), 429. (Year: 2017).
Ruiz, M.T. et al. (1998) "Initiation and Maintenance of Virus-Induced Gene Silencing," Plant Cell 10(6):937-946.
Definition of Vector by National Human Genome Research Institute (https://www.genome.gov/, Accessed Mar. 28, 2024) (Year: 2024).
U.S. Appl. No. 17/317,596, Office Action dated Aug. 14, 2024.
Li, C. et al., "Stable expression of foreign proteins in herbaceous and apple plants using Apple latent spherical virus RNA2 vectors", Arch Virol (2004) 149:1541-1558.
Avesani, L. et al., "Stability of Potato virus X expression vectors is related to insert size: implications for replication models and risk assessment", Transgenix Res (2007) 16:587-597.
International Patent Application No. PCT/US2020/060228, International Preliminary Report on Patentability dated May 17, 2022.
International Patent Application No. PCT/US2019/060945, International Preliminary Report on Patentability dated May 18, 2021.
Chinese Patent Application No. 201980088371.0, Office Action dated Jun. 28, 2024.
Japanese Patent Application No. 2021-549930, Office Action dated Dec. 3, 2024.
U.S. Appl. No. 17/291,431, Office Action dated Dec. 18, 2024.
U.S. Appl. No. 17/317,596, Office Action dated Feb. 26, 2025.
U.S. Appl. No. 17/096,593, Office Action dated Mar. 3, 2025.

* cited by examiner

Fig. 4
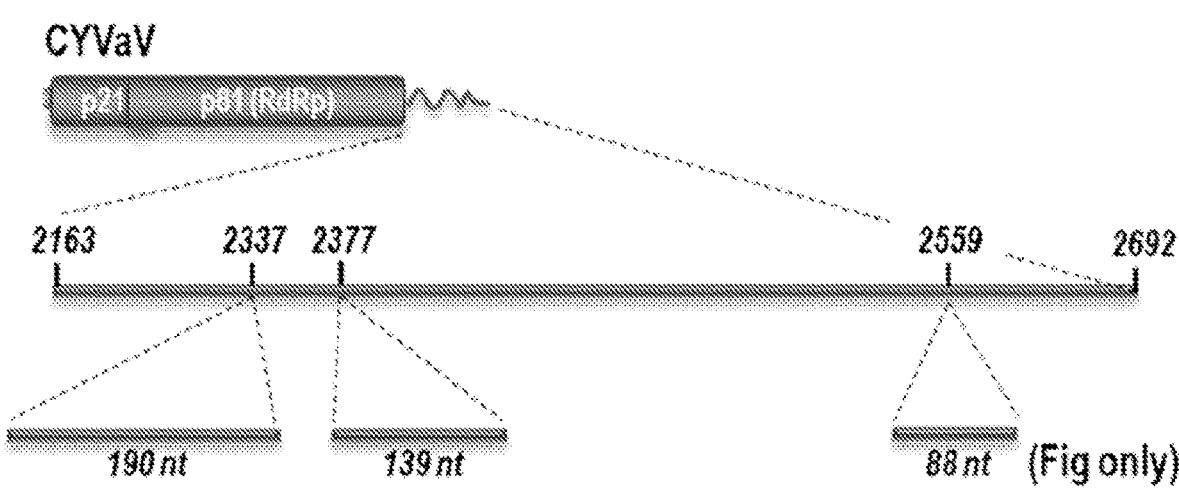
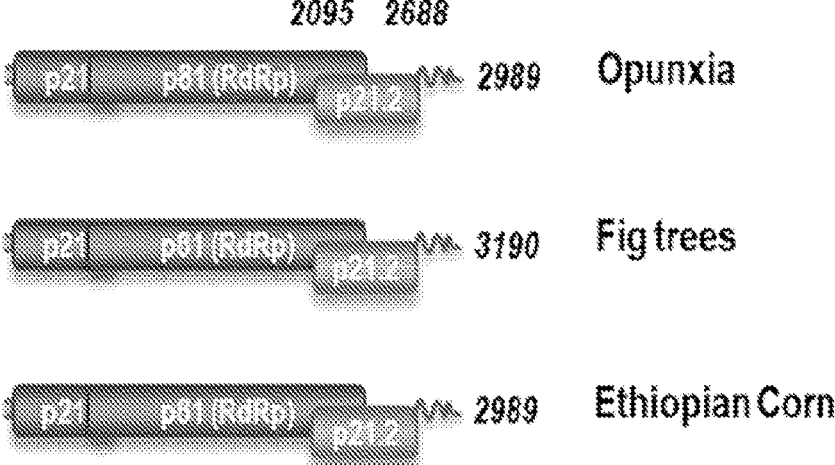

Fig. 7
A
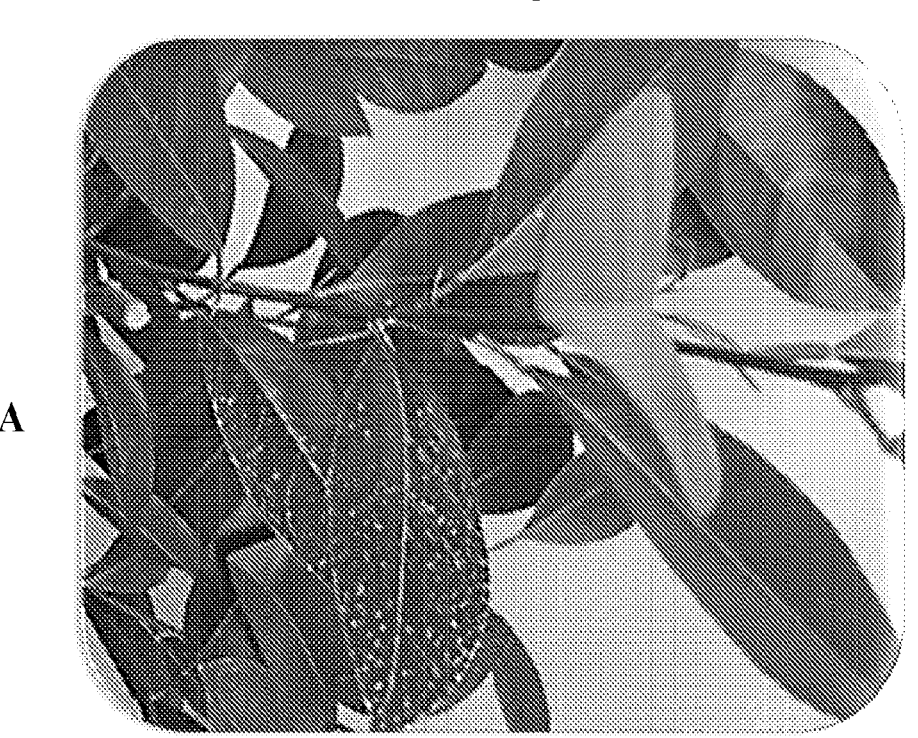
B
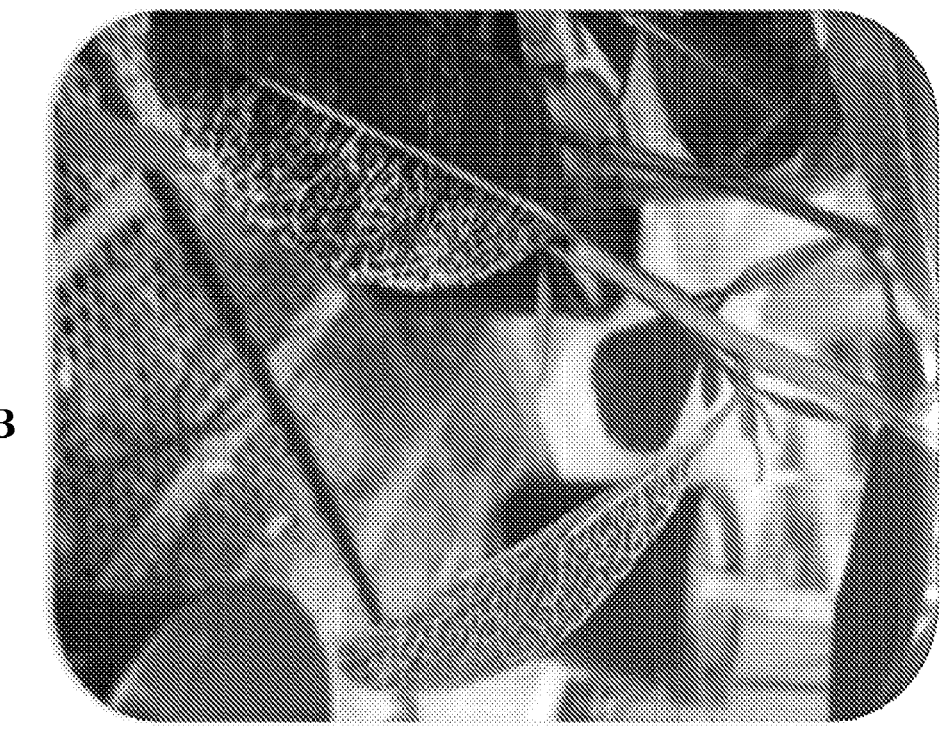

CYVaV
(SEQ ID NOs:
17, 18 and 19)

PEMV2
(SEQ ID NO:25)

(SEQ ID NO: 2)

CYVaV

Fig. 13
(A)                    (B)
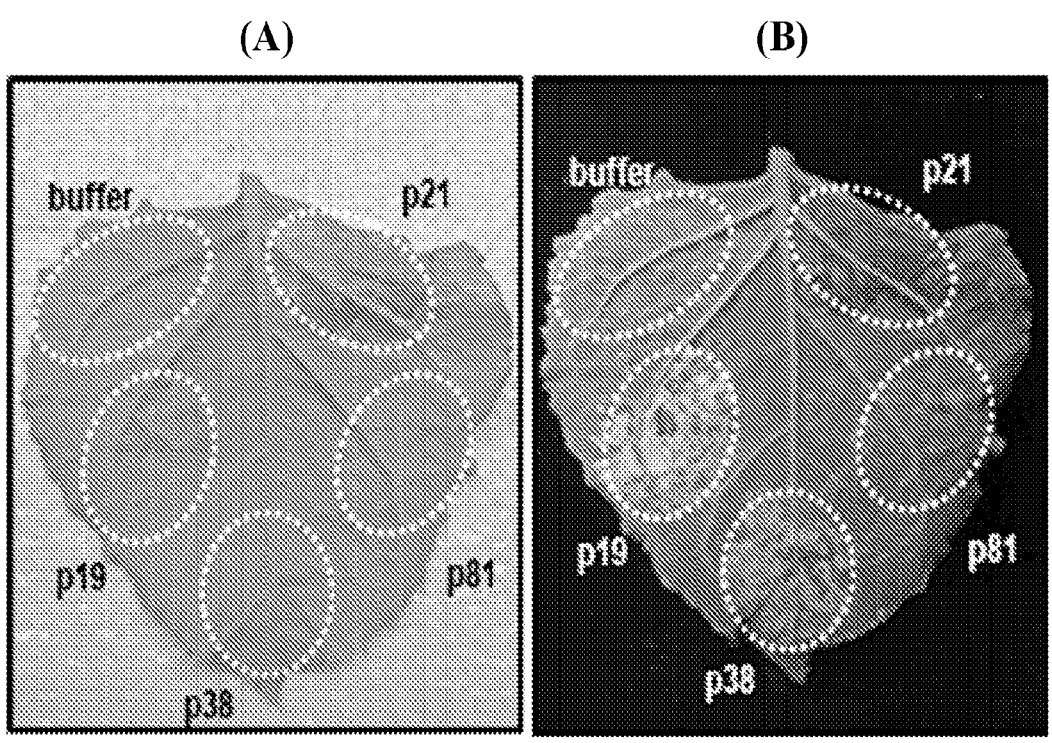
N. Benthamiana 16C
(C)
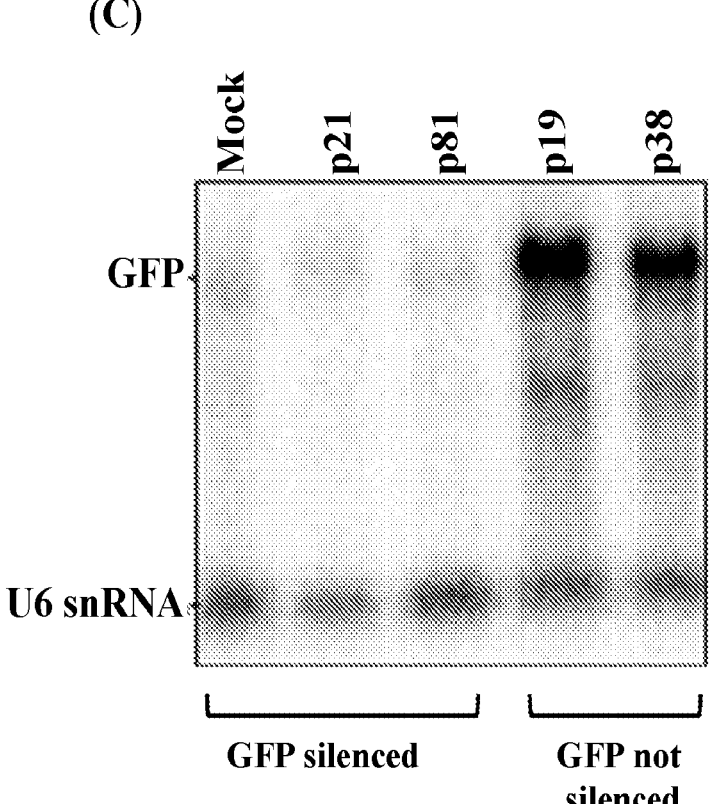

Mock     +CYVaV

| Using Refolding Buffer | No Refolding Buffer (Negative Control) |
|---|---|

(A)        (B)

NW    Ponceau Staining      NW    Ponceau Staining

Fig. 19
(A)
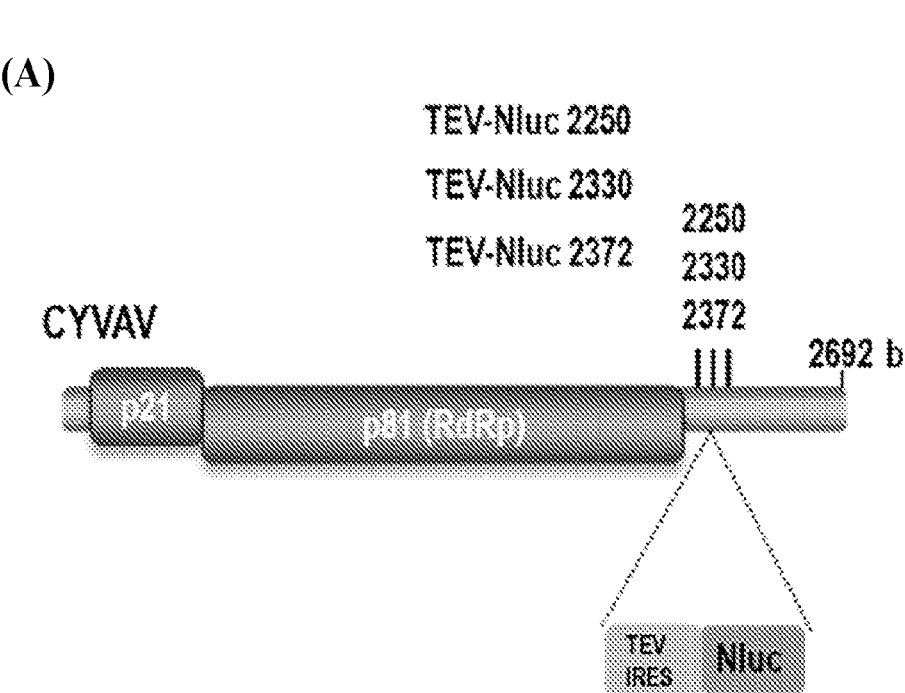
(B)
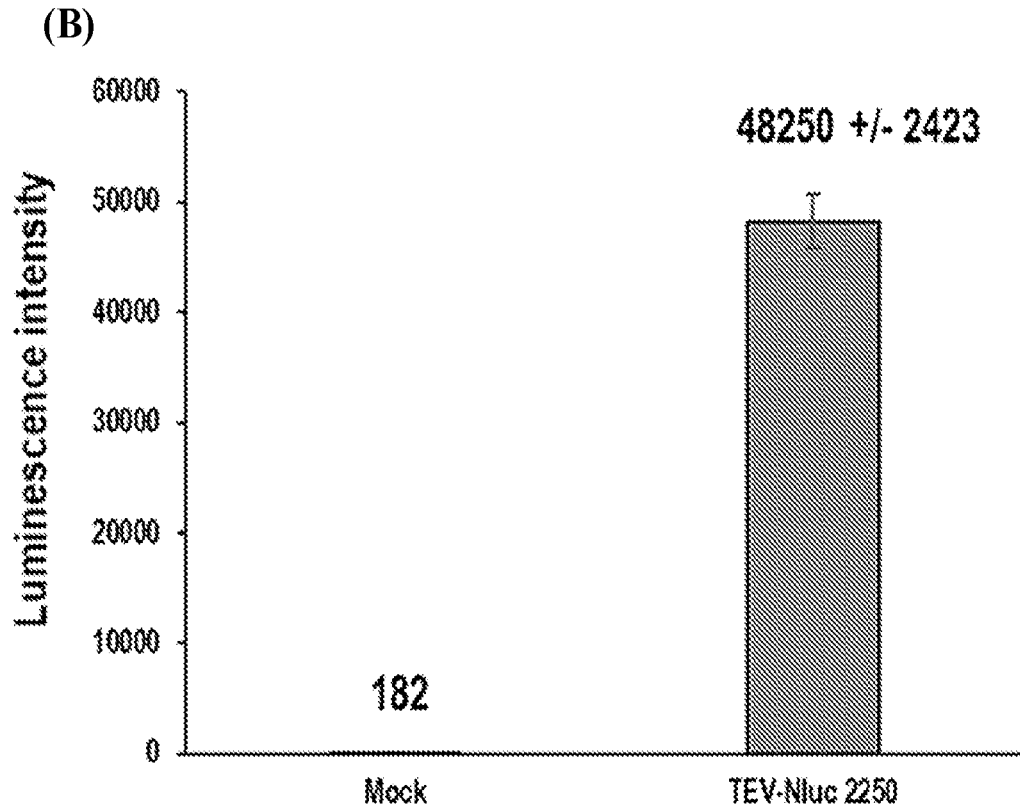

(C)

Fig. 20
A
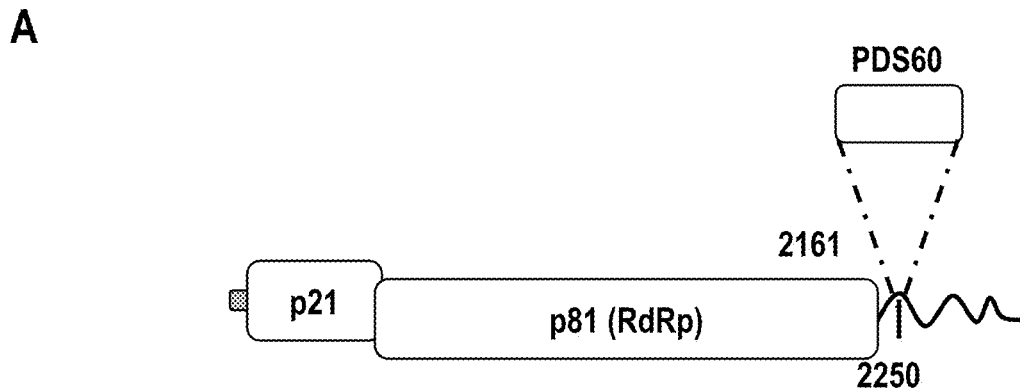
C
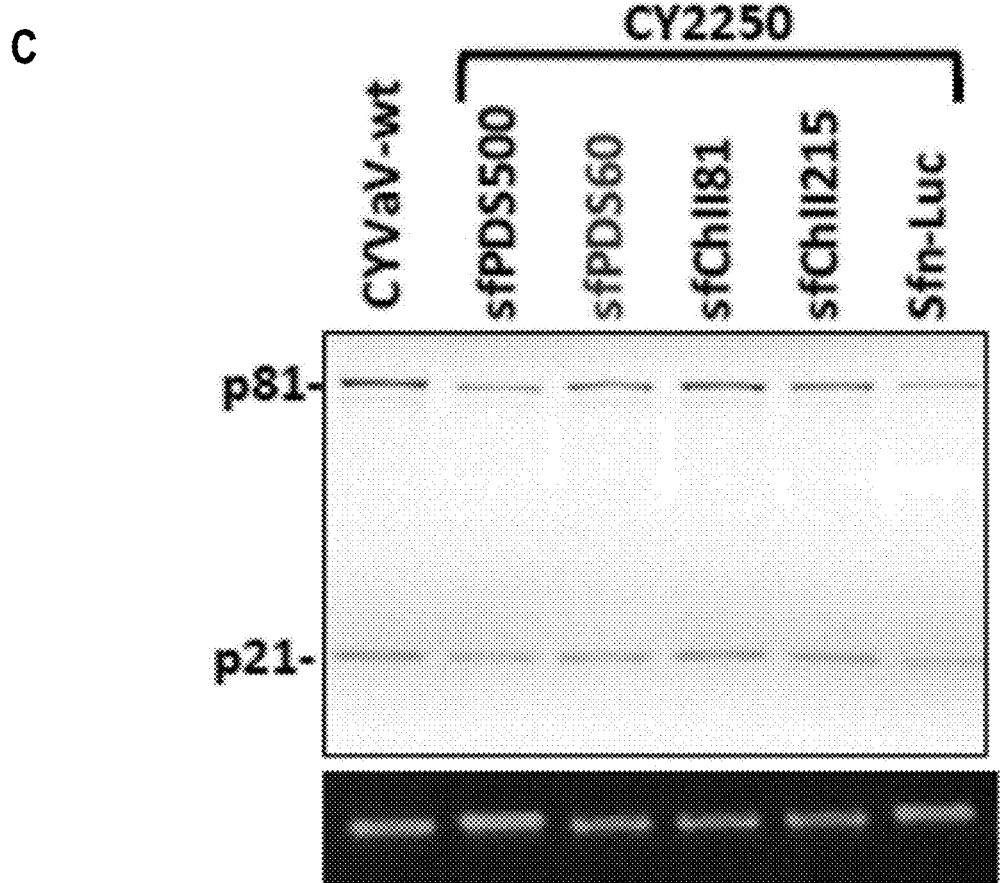

Residues 1893-1971 of SEQ ID NO: 1

Residues 2216-2337 of SEQ ID NO: 1

B

G

2250                                                                                    2251

(SEQ ID NO: 26)

TAGGCCTCGACACGGGAAGGTAGCTGTCCCGGCACTGGGTTGCACATATTCGTGCCGACGCCAC

Fig. 21
A
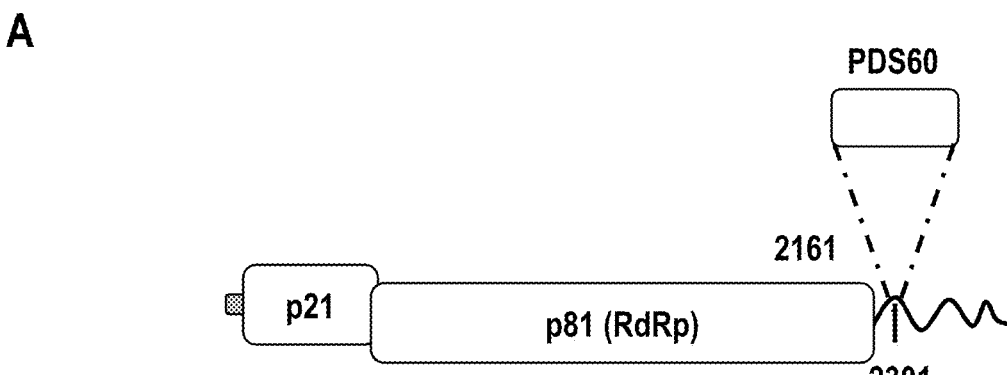
C
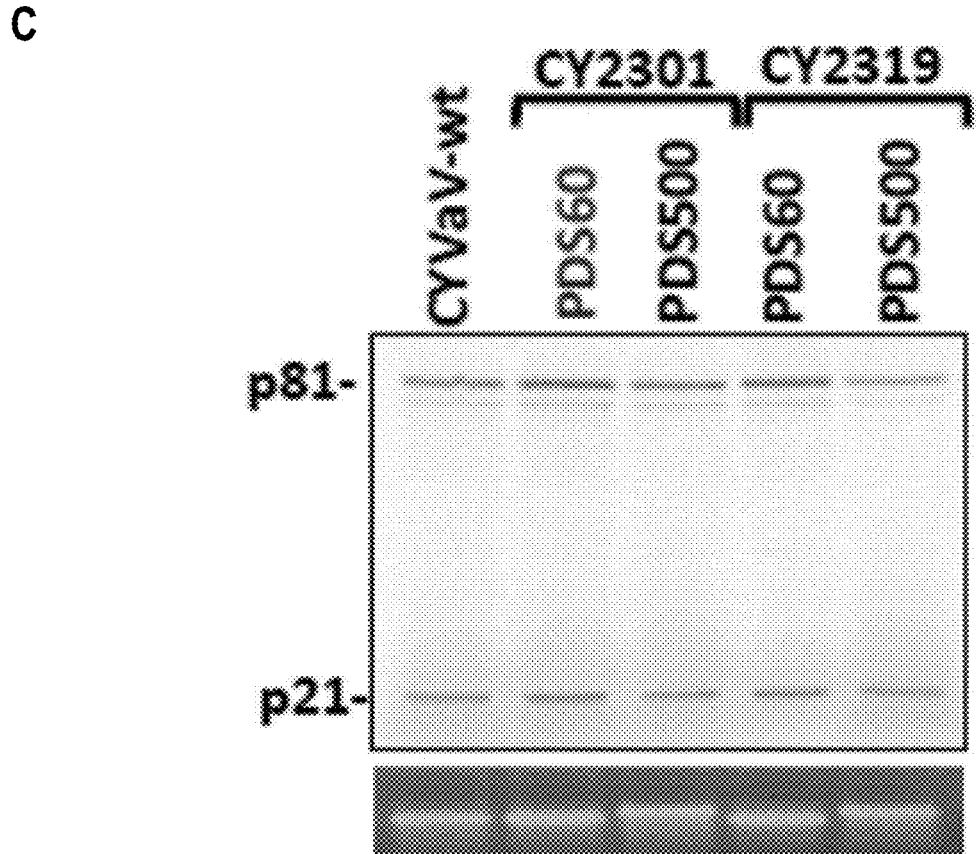

Residues 1893-1971 of SEQ ID NO: 1

Residues 2216-2337 of SEQ ID NO: 1

B

Fig. 22
A
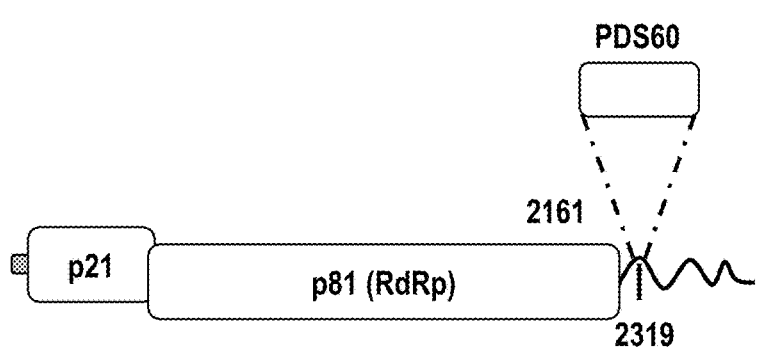
C
D
Local   Systemic

Residues 1893-1971 of SEQ ID NO: 1

Residues 2216-2337 of SEQ ID NO: 1

A

B

CYVaV-wt    +60    CYVaV-GDD

Insert in RdRp ORF

A (SEQ ID NO: 31)

(SEQ ID NO: 30)

(SEQ ID NO: 29)

GAAA/11nt
(SEQ ID NO: 28)

B (SEQ ID NO: 32)

Crystallography scaffold

C

Additional Insert(s) Location

Inserted into an RNA
(SEQ ID NO: 33

Lock sequence 1

Fig. 25
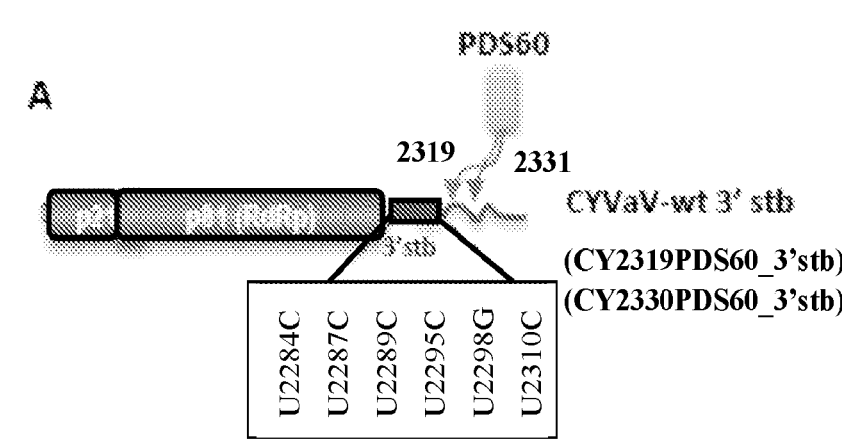
A
PDS60
2319    2331
CYVaV-wt 3' stb
(CY2319PDS60_3'stb)
(CY2330PDS60_3'stb)
U2284C  U2287C  U2289C  U2295C  U2298G  U2310C
B
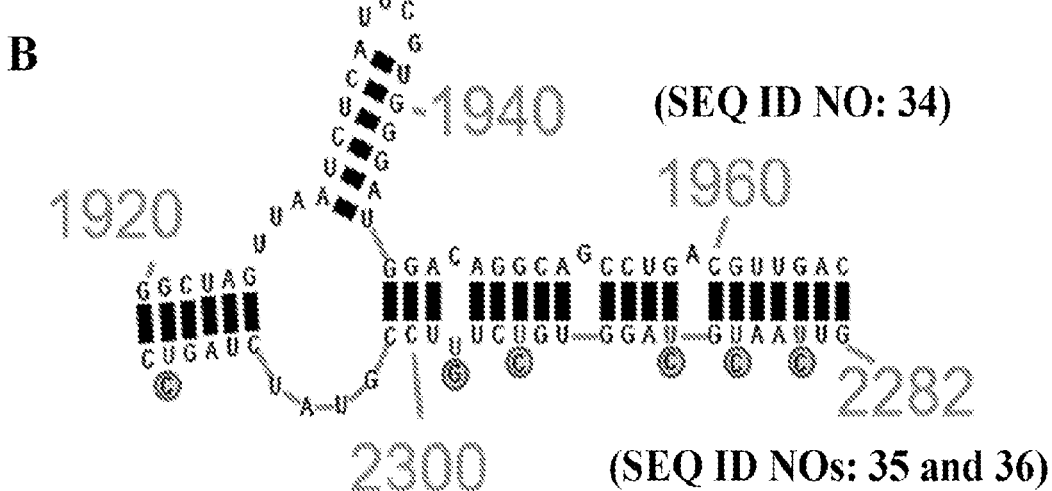
(SEQ ID NO: 34)
(SEQ ID NOs: 35 and 36)

A

Normal *N.benthamiana* (chloroplasts fluoresce red)

B

*N.benthamiana* expressing GFP

C

Infected leaf showing gene silencing in phloem from siRNAs targeting GFP mRNA generated from CYVaV

D siRNAs responsible for gene silencing migrate throughout leaf over time, eventually silencing genes in all most cells

A

CYVaVwt or CYVaV-GFPhp₂₃₀₁

CTV-GFP

CYVaVwt

CYVaV-GFPhp₂₃₀₁

B

```
      A U
   A       U
   G — C
   A — U
   C — G
   C — G
   G — C
   C — G
   G — C
   A — U
   G — C
   A — U
   A — U
   C — G
   U — A
   U — A
   C — G
   U — A
   U — A
   C — G
   A — U
   G — C
   C — G
   A — U
   C — G
   G — C
   G — C
   C — G
   G — C
   A — U
   A — U
   G — C
   U — A
```

Hairpin targeting GFP

(SEQ ID NO: 37)

Fig. 27 (cont.)
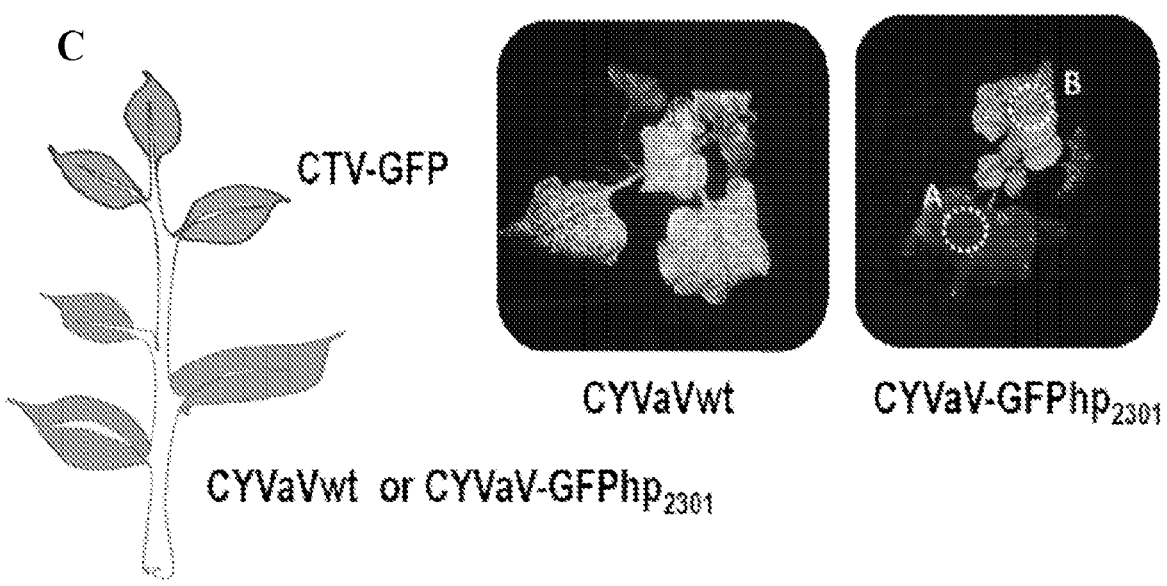
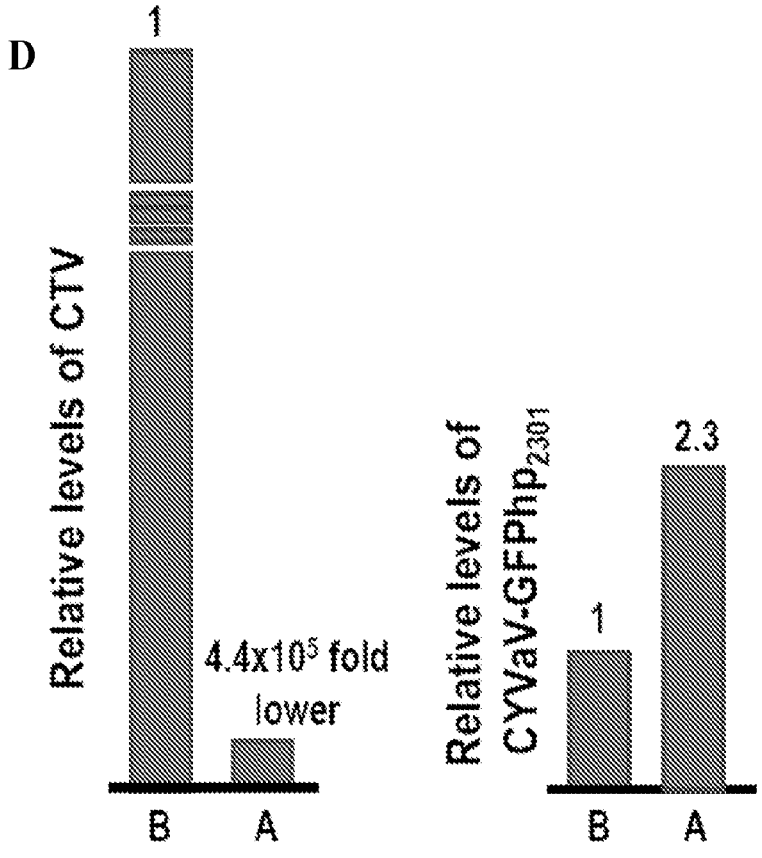

Fig. 27 (cont.)
E
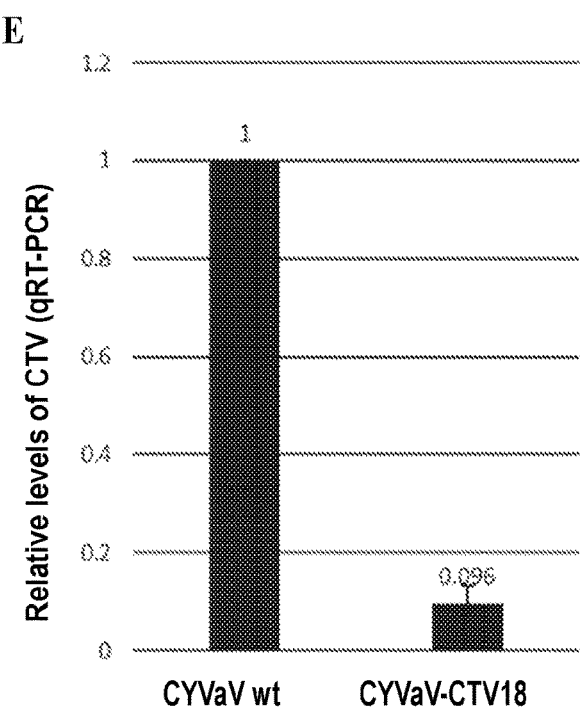
F
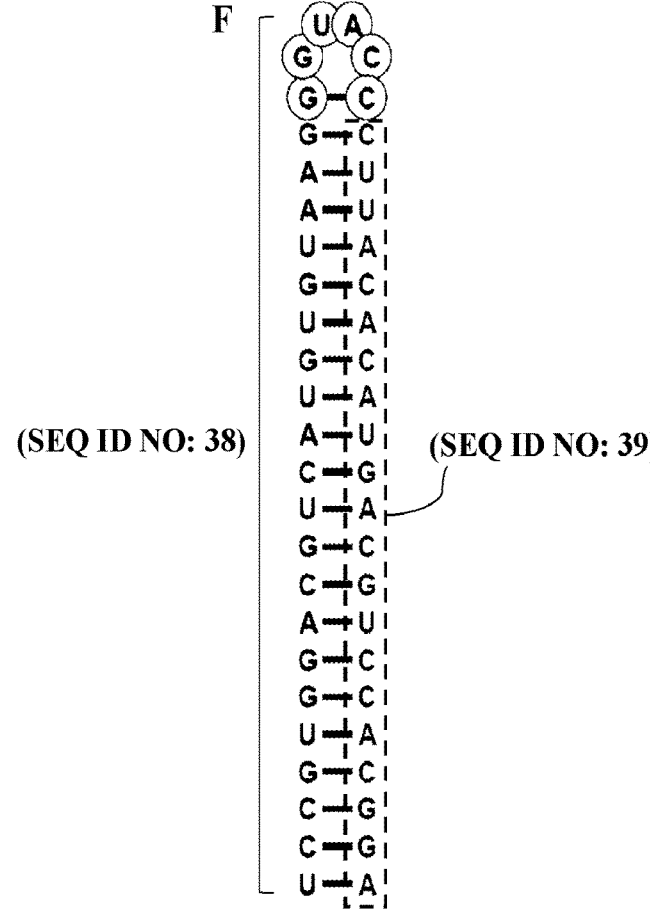
(SEQ ID NO: 38)          (SEQ ID NO: 39)

G

CYVaV
Wild-type

CYVaV-CTV6

H (SEQ ID NO: 40)

(SEQ ID NO: 41)

Fig. 28
A      Cucumber
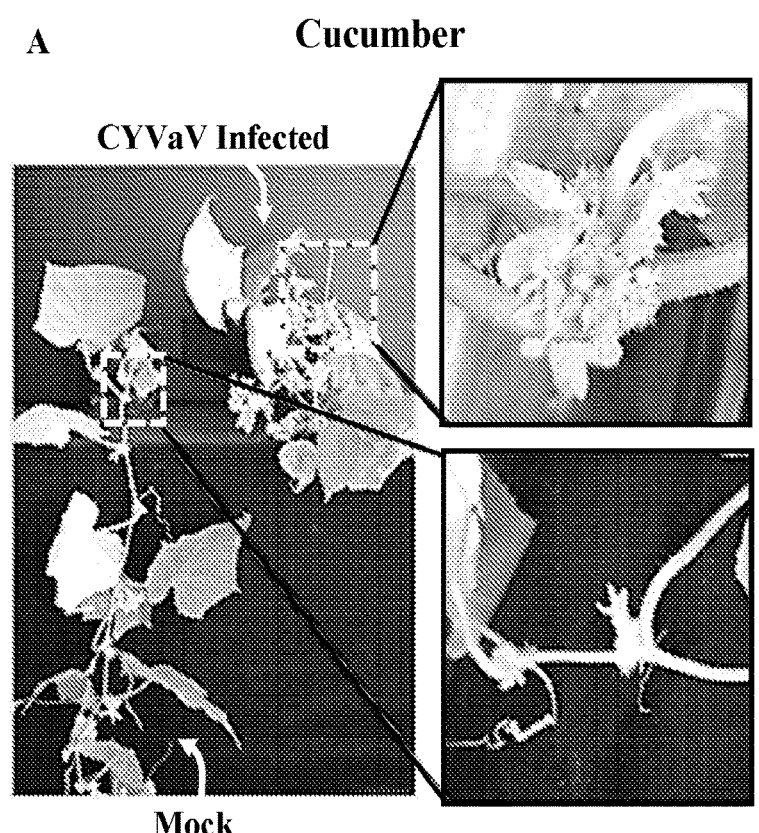
B      Tomato
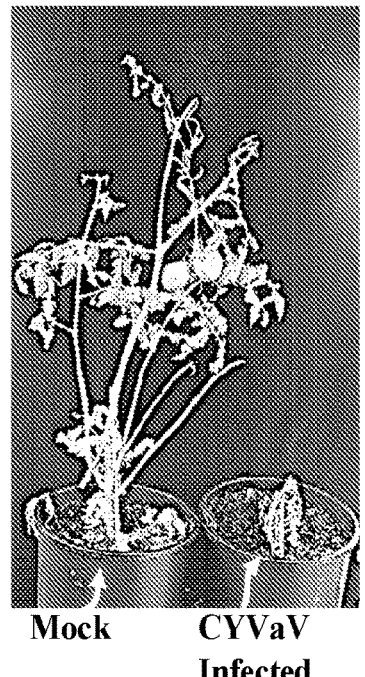

Fig. 29
A
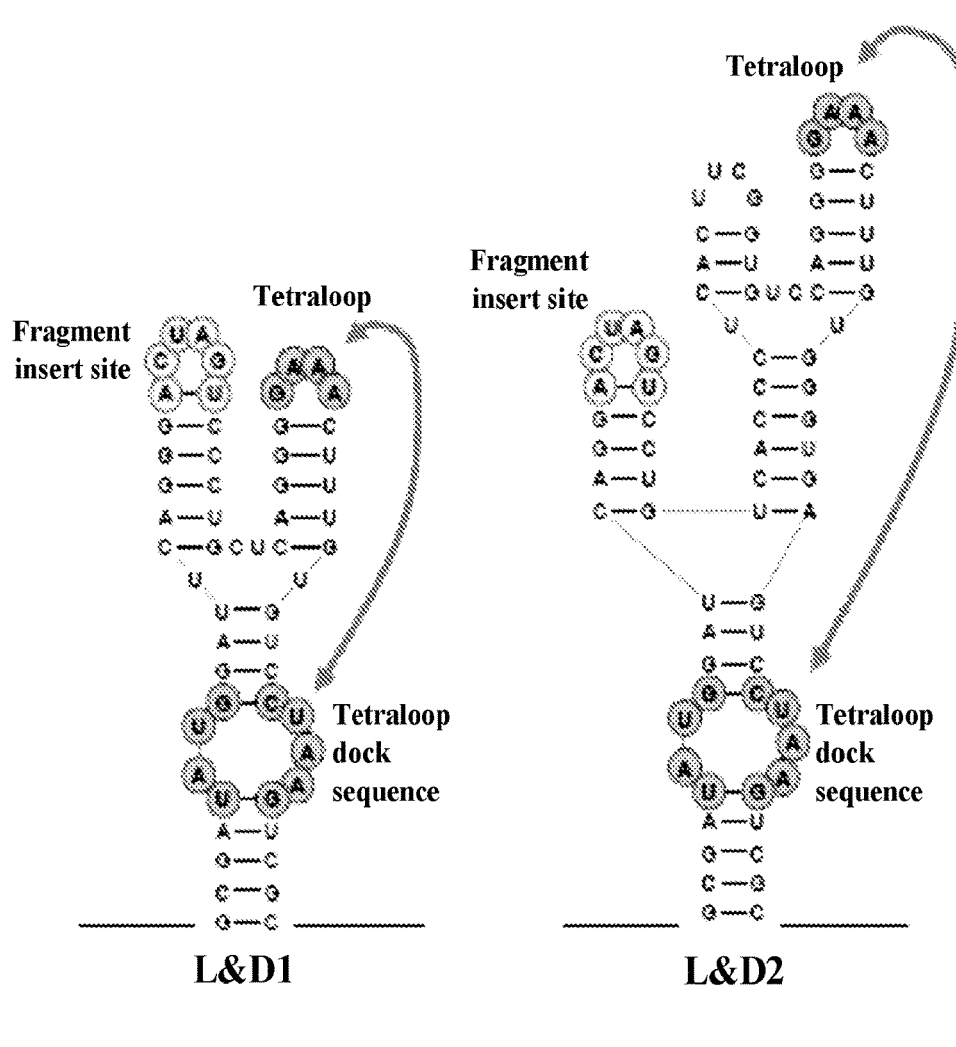
L&D1
L&D2
(SEQ ID NO: 42)
(SEQ ID NO: 43)
B
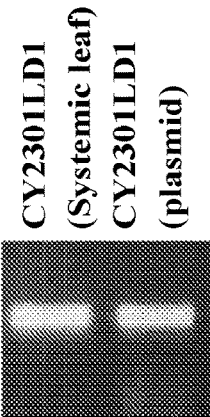

Fig. 30
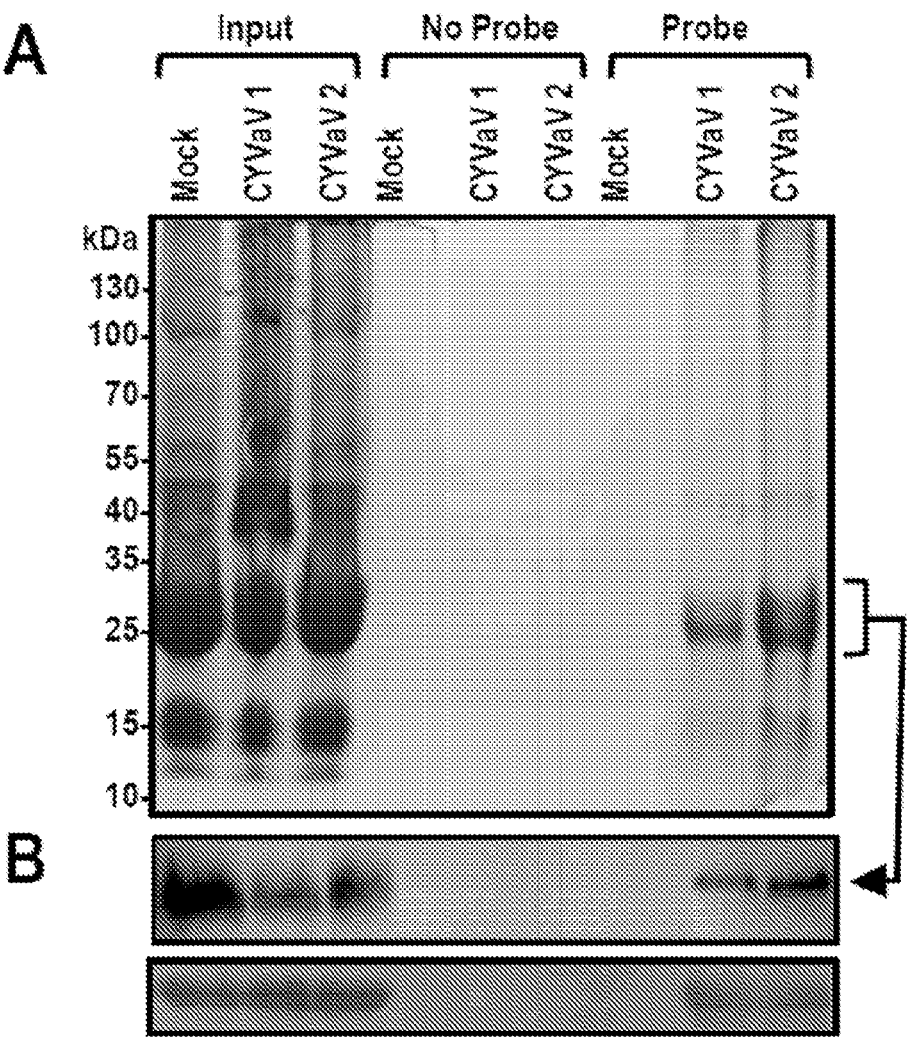
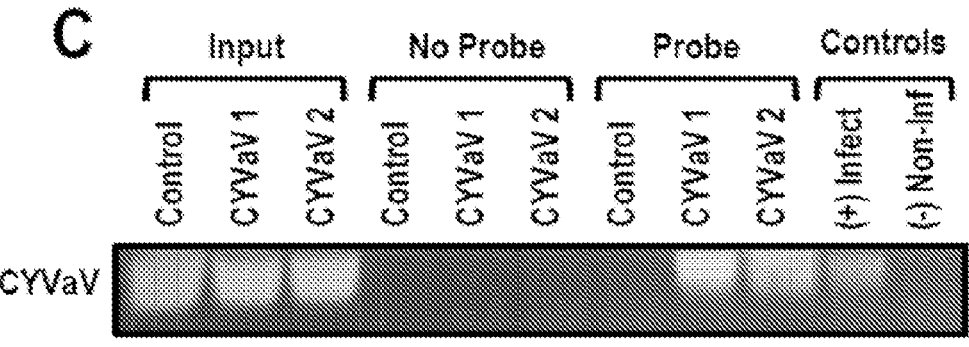

Residues 1889-2341 of SEQ ID NO: 1

CY2301GFP30s

C

CY2301LD1GFP30s

B

2301

(SEQ ID NO: 44)

Original: AGTTAATGTAGGTGTCTTTCCtgaagcggcacgacttcttcaagagcgccaGTATCTAGT

|||||||||||||||||||||||||||||||        19 nt deletion        |||||||||||

Sequencing: AGTTAATGTAGGTGTCTTTCCTGAAGCGGC~~~~~~~~~~~~~~~~~~~~~CAGTATCTAGT (SEQ ID NO: 45)                                          GFP30s          (SEQ ID NO: 46)

D (SEQ ID NO: 47)

Original: AGTTAATGTAGGTGTCTTTCCgcgatatggattcagggacttgaagcggcacgacttctt

||||||||||||||||||||||||||||||||||||||||||||||||||||||||||||

Sequencing: AGTTAATGTAGGTGTCTTTCCgcgatatggattcagggacttgaagcggcacgacttctt (SEQ ID NO: 48)          L&D1          GFP30s caagagcgccaagtccctgctcaggggaaactttgtgtcctaagtcgcGTATCTAGTCAC

|||||||||||||||||||||||||||||||||||||||||||||||||||||||||||| caagagcgccaagtccctgctcaggggaaactttgtgtcctaagtcgcGTATCTAGTCAC

GFP30s          L&D1

E

GFP30 nt: ugaagcggcacgacuucuucaagagcgcca (SEQ ID NO: 49)

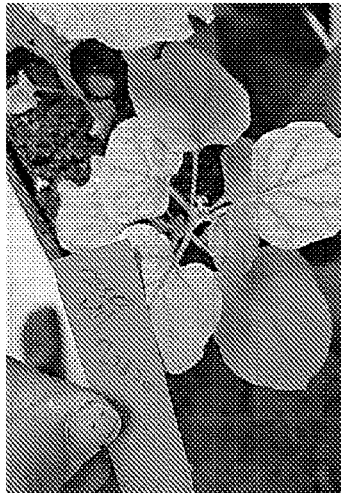

CYm2250LD1

C

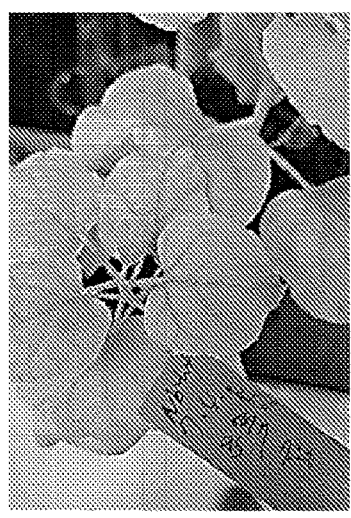

CYm2250LD1Cal7_30as

B (SEQ ID NO: 50)

```
RT-PCR  --------------------------------TGATACCTGTTCAGAATAGGATTGCTCGAGCTTCGTTG
                                        ||||||||||||||||||||||||||||||||||||||
2250LD1: AATAGGGTCATTGGTTTACCGATGATACCTGTTCAGAATAGGATTGCTCGAGCTTCGTTG
         (SEQ ID NO: 53)
```

(SEQ ID NO: 51)

```
RT-PCR  GTTAGGGTAACTCA--------------------GCGATATGGATTCAGGGACTAGTCCCTGCT
        |||||||||||||| ←---(Truncated)--→ ||||||||||||||||||||||||||||||
2250LD1:GTTAGGGTAACTCACATACCTTCTTCCATAgcgatatggattcagggactagtccctgct
```

(SEQ ID NO: 52)

```
RT-PCR  CAGGGGAAACTTTGTGTCCTAAGTCGCAC-------------------CTAACCAGT
        ||||||||||||||||||||||||||||| ←--(truncated)--→  |||||||||
2250LD1:caggggaaactttgtgtcctaagtcgcACTGGAAAAGGTCGTGTGAGCAACCTAACCAGT
```

(SEQ ID NO: 54)

```
RT-PCR  -------------------------GATACCTGTTCAGAATAGGATTGCTCGAGCTTCGTTG
                                 |||||||||||||||||||||||||||||||||||||||
2250LD1: AATAGGGTCATTGGTTTACCGATGATACCTGTTCAGAATAGGATTGCTCGAGCTTCGTTG
         (SEQ ID NO: 57)
```

(SEQ ID NO: 55)

```
RT-PCR  GTTAGGGTAACTCA◄-----------►GCGATATGGATTCAGGGACTTGATGTTGGA
        |||||||||||||| (truncated) ||||||||||||||||||
2250LD1: GTTAGGGTAACTCACATACCTTCTTCCATAgcgatatggattcagggact----------
```

Cal7_30as                 LD1

```
RT-PCR  TCCATCCTATGAGCCTTTTCAGTCCCTGCTCAGGGGAAACTTTGTGTCCTAAGTCGCAC-
                                    |||||||||||||||||||||||||||||||||||||||||
2250LD1: -------------------agtccctgctcaggggaaactttgtgtcctaagtcgACT
         (SEQ ID NO: 58) LD1
```

(SEQ ID NO: 56)

```
RT-PCR  ◄---------------------►CTAACCAGTTAATGTAGGTGTCTTTCCGTATCTAGTCAC
             (Truncated)       |||||||||||||||||||||||||||||||||||||||||
2250LD1: GGAAAAGGTCGTGTGAGCAACCTAACCAGTTAATGTAGGTGTCTTTCCGTATCTAGTCAC
```

E

Cal7_30as: ugauguuggauccauccuaugagccuuuuc (SEQ ID NO: 59)

Fig. 34
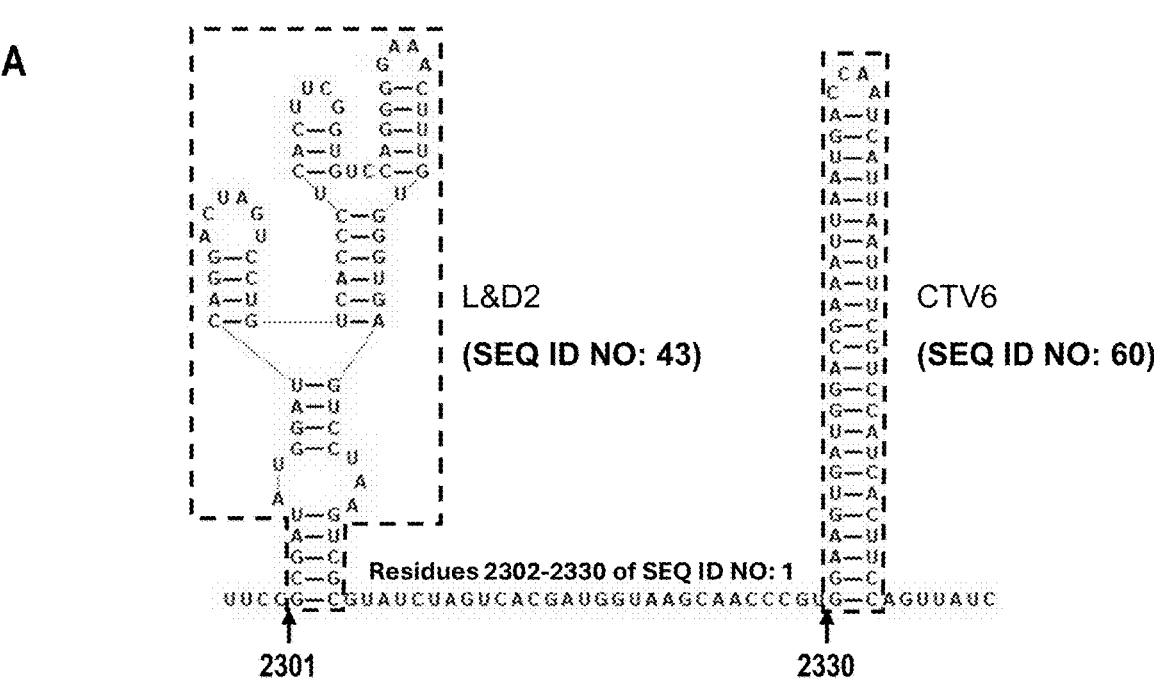
L&D2
(SEQ ID NO: 43)
CTV6
(SEQ ID NO: 60)
Residues 2302-2330 of SEQ ID NO: 1
2301
2330
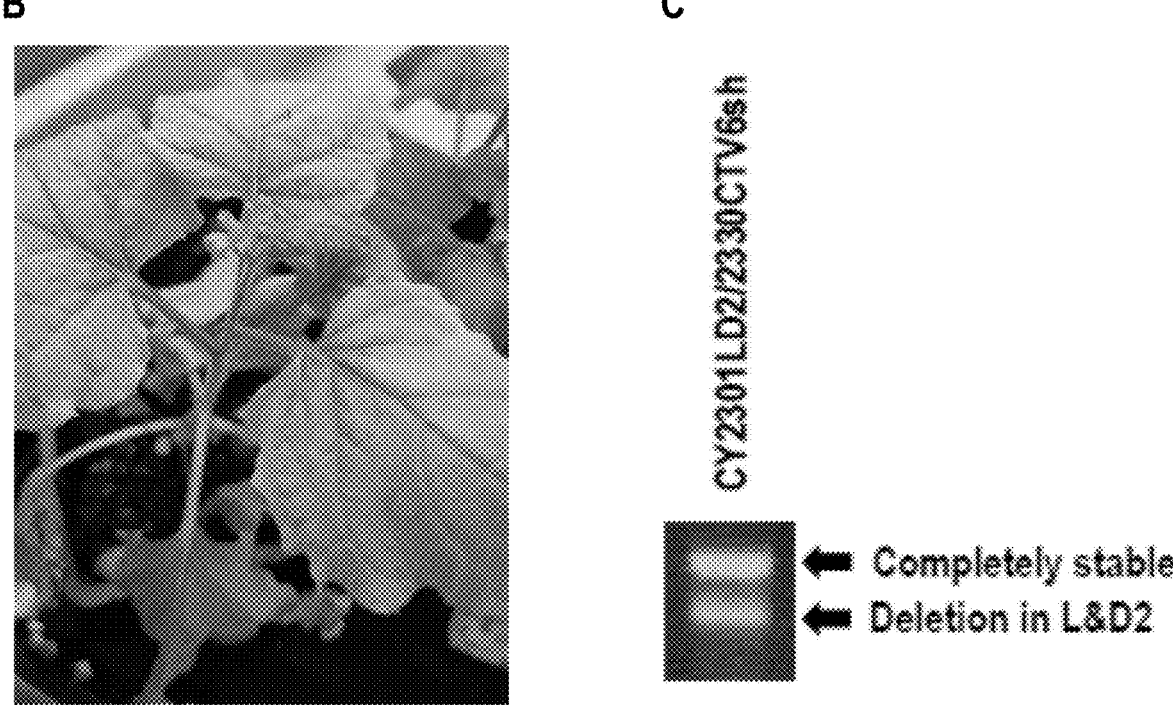

Fig. 35
A
B
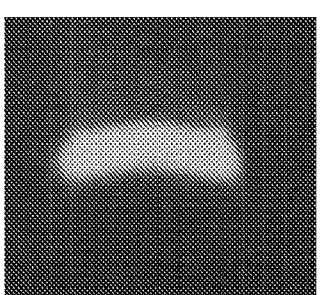
C

Fig. 36
A
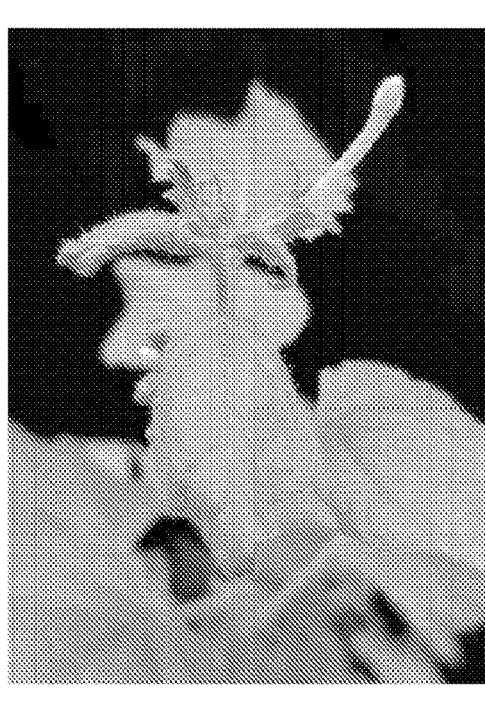
B
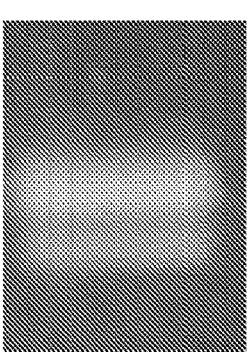
C
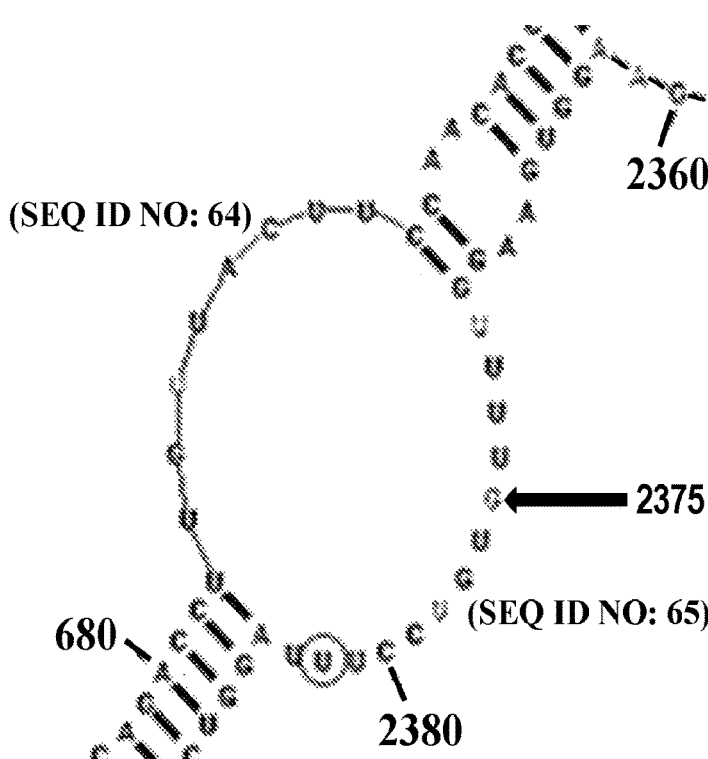
(SEQ ID NO: 64)
2360
2375
(SEQ ID NO: 65)
680
2380

SEQUENCE LISTING

<160> NUMBER OF SEQ ID NOS: 67

<210> SEQ ID NO 1
<211> LENGTH: 2692
<212> TYPE: RNA
<213> ORGANISM: Unknown
<220> FEATURE:
<223> OTHER INFORMATION: Citrus Yellow Vein associated Virus (CYVaV)

<400> SEQUENCE: 1

```
ggguaaauau ggauccuuca ucuuugcccc gugccuguug gcaucaugcc agacaggugu      60
uucgagcauc aacuagcuuc ucaagagagg ugguucgcgc ugcucguaga uggguuacca     120
ugcccaccag ucgccaugca uaugacuuuu caacgagucu aggcauugug auugcugagc     180
cugcagcucg uuuacgacgc cgucugcccu cuguacgaaa gugcgcagag aaguuaguag     240
uccacaagca agucgacacu uugguggacg aauggugcuc uggaauuccc aacccugaua     300
ucguagaagu ugguugggca cuccgucuga gggaccguuu cggucuuccu cccgcuucug     360
agccuacccg gcucaguggu gagagauggg ugcucaaaca acucaauggg guagauccug     420
agucauggaa ugcugaucuu gguaggucag uucauaucca aggagacuac gccccaggga     480
ggaaugccca uaucgcucag gucgcggcga ccuugugguu aacuaggacc uugcaugaca     540
aggccuuggc ucgccaccag gguuuucgcg auuugcagug auuggggucg acgggcuaga     600
ggcaaaagca gugccucuag cuucuggacu ccgacugcuu ccgguuccgc gacccggaca     660
aagucgacga cugucucaga ccuuguuacu uccaacaccu cgugcucaau ucgugaauca     720
cgcgugcucg gcuaacaacc uuggacgugu gaugaccaca cguguguugc aguacaaggg     780
ccgagauccg auccuucccu cuucgaagc ccuucaccga cuuaaccuuc ggauagcuga     840
gcuauauagg ucuagaccuu cuaccgucua uccauuaagu uaugaagggu uucucaauug     900
cuaugaaggc cgacagcgua cucguuacgc ccaagccguc gagcaguuga ugcgguccac     960
ucuugagccg aaagaugcgc gaguugaaac guucauuaag aacgagaaau uugacugggc    1020
guugaaaggg gaggaggcug auccucgagc aauccaacca aggaagccga aauauuuggc    1080
ugagguugga cggugguuca aaccuuugga gcgaaucauc uacaaggauc ucaguaaaag    1140
guuguauggu gagggugcug agccguguau cgccaaaggc cuaaaugcau uagaaucugg    1200
agcgacuuug aggcgcaaau gggagaaguu uucuucucca guuugcguuu cucucgacgc    1260
uuccagguuc gaccugcaug uaagcguugg caugcuaaag uucacacaca agcuauauga    1320
cuauuacugu aagucuccca cucuccagcg cuaucucaaa uggacacucc gcaaccaugg    1380
cgucgccucc ugcaaagaau ugucauauga guaugagguu guuggccgga gaaugagugg    1440
ugacauggac acugcauugg gcaacugcgu cauuaugucg auacuuacau gguuuaugcu    1500
uagugaacuu ggcauuaagc augaauuauu cgauaauggu gacgauuguu uguucauuug    1560
cgagucucac gacgucccca gccccgaggu aauuacaaac ugguuuucgg acuuuggguu    1620 uguggguuagg uuggaaggcg ucacguccgu guuugagcgu auugaguuuu gccaaacuuc    1680
cccaguaugg acugagaggg guuggcugau guguaggaau auuaagucau ugaguaaaga    1740
```

-continued

```
ccuuacgaau guuaauucgu gcacgggcuc cacgauugaa uauacccacu gguugaaagc      1800 aguggggaaag ugcgggucaa uacucaaugc uggguguaccu auauuucagu ccuuucacaa     1860
caugcuggaa aggcuuggca cuaacucucg uauugaucga ggggguuuucu ucaaaucagg     1920 gcuaguuaau cucauucgug ggauggacag gcagccugac guugacauca cuacuuccgc      1980
ucggcuuucu uucgaagugg cauucgggau aacacccggg augcaauugg cuauugaacg      2040
guacuaugac ucugucaugg gcucgcugag uaaaauagaa acaacuaagu ggccaauuga      2100
acuaagaaag gaauacgaac acggaaguga gugguacgag gacuuaggcg uccuaggaug      2160
aauaggguca uugguuuacc gaugauaccu guucagaaua ggauugcucg agcuucguug      2220
guuaggguaa cucacauacc uucuuccaua acuggaaaag gucgugugag caaccuaacc      2280
aguuaaugua ggugucuuuc cguaucuagu cacgauggua agcaacccgu uuaucuguac      2340
ggcgcucacc cgugggguagg aaggugaagg uuuugugucc uuuaggucuu ggacagucug      2400
cgggcuuggg aacgacgccc cgcuagcaac guacugcucu ccuaccggac ugguagcuua      2460
auugucaucu uggagcgaua gcacgugggg ccucacccuu cgcgcguugg acguguugcg      2520 ugcccccac agauuuguga aacucuaugg agcaguuccg cgagccagaa gggaggaugg       2580
ccgccuggcg uaaccagga gcucggggg gcuuguacuc agaguagcau ucugcuuuag        2640
acuguuaacu uuaugaacca cgcgugucac gugggggagag uuaacagcgc cc             2692
```

<210> SEQ ID NO 2
<211> LENGTH: 225
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(225)
<223> OTHER INFORMATION: 3' End of CYVaV

<400> SEQUENCE: 2

```
ucuuggagcg auagcacugu gggccucacc cuucgcgcgu uggacguguu gcgugccccc      60
cacagauuug ugaaacucua uggagcaguu ccgcgagcca gaagggagga uggccgccug     120
gcguaaucca ggagcucugg ggggcuugua cucagaguag cauucugcuu uagacuguua     180
acuuuaugaa ccacgcgugu cacguggggga gaguuaacag cgccc                    225
```

<210> SEQ ID NO 3
<211> LENGTH: 84
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(84)
<223> OTHER INFORMATION: The 3' Cap Independent Translation Enhancer (3'
      CITE) of CYVaV

<400> SEQUENCE: 3

```
ucuuggagcg auagcacugu gggccucacc cuucgcgcgu uggacguguu gcgugccccc      60
cacagauuug ugaaacucua ugga                                            84
```

<210> SEQ ID NO 4

<400> SEQUENCE: 4

000

<210> SEQ ID NO 5

<400> SEQUENCE: 5

000

<210> SEQ ID NO 6
<211> LENGTH: 570
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(570)
<223> OTHER INFORMATION: Polynucleotide Sequence of CYVaV Encoding
      Protein p21 (bases 9 to 578)

<400> SEQUENCE: 6
auggauccuu caucuuugcc ccgugccugu uggcaucaug ccagacaggu guuucgagca      60
ucaacuagcu ucucaagaga ggugguucgc gcugcucgua gauggguuac caugcccacc     120
agucgccaug cauaugacuu uucaacgagu cuaggcauug ugauugcuga gccugcagcu     180
cguuuacgac gccgucugcc cucuguacga aagugcgcag agaaguuagu aguccacaag     240
caagucgaca cuuuggugga cgaauggugc ucuggaauuc ccaacccuga uaucguagaa     300
guugguuggg cacuccgucu gagggaccgu uucggucuuc cucccgcuuc ugagccuacc     360
cggcucagug gugagagaug ggugcucaaa caacucaaug ggguagaucc ugagucaugg     420
aaugcugauc uugguagguc aguucauauc caaggagacu acgccccagg gaggaaugcc     480
cauaucgcuc aggucgcggc gaccuugugg uuaacuagga ccuugcauga caaggccuug     540
gcucgccacc aggguuuucg cgauuugcag                                      570

<210> SEQ ID NO 7
<211> LENGTH: 190
<212> TYPE: PRT
<213> ORGANISM: Unknown
<220> FEATURE:
<223> OTHER INFORMATION: Citrus Yellow Vein associated Virus (CYVaV)
<220> FEATURE:
<221> NAME/KEY: MISC_FEATURE
<222> LOCATION: (1)..(190)
<223> OTHER INFORMATION: Citrus Yellow Vein associated Virus (CYVaV)
      Protein p21

<400> SEQUENCE: 7

Met Asp Pro Ser Ser Leu Pro Arg Ala Cys Trp His His Ala Arg Gln
1               5                   10                  15

Val Phe Arg Ala Ser Thr Ser Phe Ser Arg Glu Val Val Arg Ala Ala
            20                  25                  30

Arg Arg Trp Val Thr Met Pro Thr Ser Arg His Ala Tyr Asp Phe Ser
        35                  40                  45

Thr Ser Leu Gly Ile Val Ile Ala Glu Pro Ala Ala Arg Leu Arg Arg
    50                  55                  60

Arg Leu Pro Ser Val Arg Lys Cys Ala Glu Lys Leu Val Val His Lys
65                  70                  75                  80

Gln Val Asp Thr Leu Val Asp Glu Trp Cys Ser Gly Ile Pro Asn Pro
                85                  90                  95

Asp Ile Val Glu Val Gly Trp Ala Leu Arg Leu Arg Asp Arg Phe Gly
            100                 105                 110

```
Leu Pro Pro Ala Ser Glu Pro Thr Arg Leu Ser Gly Glu Arg Trp Val
    115                 120                 125

Leu Lys Gln Leu Asn Gly Val Asp Pro Glu Ser Trp Asn Ala Asp Leu
    130                 135                 140

Gly Arg Ser Val His Ile Gln Gly Asp Tyr Ala Pro Gly Arg Asn Ala
145                 150                 155                 160

His Ile Ala Gln Val Ala Ala Thr Leu Trp Leu Thr Arg Thr Leu His
                165                 170                 175

Asp Lys Ala Leu Ala Arg His Gln Gly Phe Arg Asp Leu Gln
            180                 185                 190

<210> SEQ ID NO 8
<211> LENGTH: 1407
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(1407)
<223> OTHER INFORMATION: Polynucleotide Sequence of CYVaV Encoding
      Protein p81 (bases 752 to 2158)

<400> SEQUENCE: 8
augaccacac gugüguugca guacaagggc cgagauccga uccuucccuc uucugaagcc      60
cuucaccgac uuaaccuucg gauagcugag cuauauaggu cuagaccuuc uaccgucuau     120
ccauuaaguu augaaggguu ucucaauugc uaugaaggcc gacagcguac ucguuacgcc     180
caagccgucg agcaguugau gcgguccacu cuugagccga aagaugcgcg aguugaaacg     240
uucauuaaga acgagaaauu ugacugggcg uugaaagggg aggaggcuga uccucgagca     300
auccaaccaa ggaagccgaa auauuuggcu gagguuggac ggugguucaa accuuuggag     360
cgaaucaucu acaaggaucu caguaaaagg uuguauggug aggugcuga gccguguauc     420 gccaaaggcc uaaaugcauu agaaucugga gcgacuuuga ggcgcaaaug ggagaaguuu     480
ucuucuccag uuugcguuuc ucucgacgcu uccagguucg accugcaugu aagcguuggc     540
augcuaaagu ucacacacaa gcuauaugac uauuacugua agucucccac ucuccagcgc     600
uaucucaaau ggacacuccg caaccauggc gucgccuccu gcaaagaauu gucauaugag     660
uaugagguug uuggccggag aaugaguggu gacauggaca cugcauuggg caacugcguc     720
auuaugucga uacuuacaug guuuaugcuu agugaacuug gcauuaagca ugaauuauuc     780
gauaauggug acgauuguuu guucauuugc gagucucacg acguccccag ccccgaggua     840
auuacaaacu gguuuucgga cuuugggüuu gugguuaggu uggaaggcgu cacguccgug     900
uuugagcgua uugaguuuug ccaaacuucc ccaguaugga cugagagggg uuggcugaug     960
uguaggaaua uuaagucauu gaguaaagac cuuacgaaug uuaauucgug cacgggcucc    1020
acgauugaau auacccacug guugaaagca gugggaaagu gcgggucaau acucaaugcu    1080
gguguaccua uauuucaguc cuuucacaac augcuggaaa ggcuuggcac uaacucucgu    1140
auugaucgag ggguuuucuu caaaucaggg cuaguuaauc ucauucgugg gauggacagg    1200
cagccugacg uugacaucac uacuuccgcu cggcuuucuu ucgaaguggc auucgggaua    1260
acacccggga ugcaauuggc uauugaacgg uacuaugacu cugucauggg cucgcugagu    1320
aaaauagaaa caacuaagug gccaauugaa cuaagaaagg aauacgaaca cggaagugag    1380
ugguacgagg acuuaggcgu ccuagga                                        1407
```

```
<210> SEQ ID NO 9
<211> LENGTH: 469
<212> TYPE: PRT
<213> ORGANISM: Unknown
<220> FEATURE:
<223> OTHER INFORMATION: Citrus Yellow Vein associated Virus (CYVaV)

<400> SEQUENCE: 9

Met Thr Thr Arg Val Leu Gln Tyr Lys Gly Arg Asp Pro Ile Leu Pro
1               5                   10                  15

Ser Ser Glu Ala Leu His Arg Leu Asn Leu Arg Ile Ala Glu Leu Tyr
            20                  25                  30

Arg Ser Arg Pro Ser Thr Val Tyr Pro Leu Ser Tyr Glu Gly Phe Leu
        35                  40                  45

Asn Cys Tyr Glu Gly Arg Gln Arg Thr Arg Tyr Ala Gln Ala Val Glu
    50                  55                  60

Gln Leu Met Arg Ser Thr Leu Glu Pro Lys Asp Ala Arg Val Glu Thr
65                  70                  75                  80

Phe Ile Lys Asn Glu Lys Phe Asp Trp Ala Leu Lys Gly Glu Glu Ala
                85                  90                  95

Asp Pro Arg Ala Ile Gln Pro Arg Lys Pro Lys Tyr Leu Ala Glu Val
            100                 105                 110

Gly Arg Trp Phe Lys Pro Leu Glu Arg Ile Ile Tyr Lys Asp Leu Ser
        115                 120                 125

Lys Arg Leu Tyr Gly Glu Gly Ala Glu Pro Cys Ile Ala Lys Gly Leu
    130                 135                 140

Asn Ala Leu Glu Ser Gly Ala Thr Leu Arg Arg Lys Trp Glu Lys Phe
145                 150                 155                 160

Ser Ser Pro Val Cys Val Ser Leu Asp Ala Ser Arg Phe Asp Leu His
                165                 170                 175

Val Ser Val Gly Met Leu Lys Phe Thr His Lys Leu Tyr Asp Tyr Tyr
            180                 185                 190

Cys Lys Ser Pro Thr Leu Gln Arg Tyr Leu Lys Trp Thr Leu Arg Asn
        195                 200                 205

His Gly Val Ala Ser Cys Lys Glu Leu Ser Tyr Glu Tyr Glu Val Val
    210                 215                 220

Gly Arg Arg Met Ser Gly Asp Met Asp Thr Ala Leu Gly Asn Cys Val
225                 230                 235                 240

Ile Met Ser Ile Leu Thr Trp Phe Met Leu Ser Glu Leu Gly Ile Lys
                245                 250                 255

His Glu Leu Phe Asp Asn Gly Asp Asp Cys Leu Phe Ile Cys Glu Ser
            260                 265                 270

His Asp Val Pro Ser Pro Glu Val Ile Thr Asn Trp Phe Ser Asp Phe
        275                 280                 285

Gly Phe Val Val Arg Leu Glu Gly Val Thr Ser Val Phe Glu Arg Ile
    290                 295                 300

Glu Phe Cys Gln Thr Ser Pro Val Trp Thr Glu Arg Gly Trp Leu Met
305                 310                 315                 320

Cys Arg Asn Ile Lys Ser Leu Ser Lys Asp Leu Thr Asn Val Asn Ser
                325                 330                 335

Cys Thr Gly Ser Thr Ile Glu Tyr Thr His Trp Leu Lys Ala Val Gly
            340                 345                 350

Lys Cys Gly Ser Ile Leu Asn Ala Gly Val Pro Ile Phe Gln Ser Phe
        355                 360                 365

His Asn Met Leu Glu Arg Leu Gly Thr Asn Ser Arg Ile Asp Arg Gly
```

-continued

```
        370             375             380

Val Phe Phe Lys Ser Gly Leu Val Asn Leu Ile Arg Gly Met Asp Arg
385             390             395             400

Gln Pro Asp Val Asp Ile Thr Thr Ser Ala Arg Leu Ser Phe Glu Val
            405             410             415

Ala Phe Gly Ile Thr Pro Gly Met Gln Leu Ala Ile Glu Arg Tyr Tyr
            420             425             430

Asp Ser Val Met Gly Ser Leu Ser Lys Ile Glu Thr Thr Lys Trp Pro
            435             440             445

Ile Glu Leu Arg Lys Glu Tyr Glu His Gly Ser Glu Trp Tyr Glu Asp
        450             455             460

Leu Gly Val Leu Gly
465
```

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 166
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(166)

<223> OTHER INFORMATION: Polynucleotide Sequence of Recoding Frameshift
     Sites of CYVaV

<400> SEQUENCE: 17
ucgcucaggu cgcggcgacc uuguggguuaa cuaggaccuu gcaugacaag gccuuggcuc        60
gccaccaggg uuuucgcgau uugcagugau uggggucgac gggcuagagg caaaagcagu       120
gccucuagcu ucuggacucc gacugcuucc gguuccgcga cccgga                      166

<210> SEQ ID NO 18
<211> LENGTH: 25
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(25)
<223> OTHER INFORMATION: Polynucleotide Sequence of Recoding Frameshift
     Sites of CYVaV

<400> SEQUENCE: 18
caaagucgac gacugucuca gaccu                                              25

<210> SEQ ID NO 19
<211> LENGTH: 34
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(34)
<223> OTHER INFORMATION: Polynucleotide Sequence of Recoding Frameshift
     Sites of CYVaV

<400> SEQUENCE: 19
aggucuugga cagucugcgg gcuugggaac gacg                                    34

<210> SEQ ID NO 20
<211> LENGTH: 3132
<212> TYPE: RNA
<213> ORGANISM: Ficus carica
<220> FEATURE:
<221> NAME/KEY: misc_feature
<223> OTHER INFORMATION: Polynucleotide Sequence of Fig Tree iRNA ("iRNA
     relative 1" or "iRNA r1")

<400> SEQUENCE: 20
aaauauggau ucgauaucaa ugcccgucgc cugcugguca aaagccaggc aggucuugcg        60
uacaccagcu aacuuuucca aaggggguagu gaaggcugcg uaccggugggu ucaacaugcc      120 cagagccaaa uaugucagag augucuccac gagucuuggc auaguugucg cugagccugu       180
ugcugccgug cgccguuaga ugccuucgau aagcagccuu gcggaggagu ugguaacacg       240
ccagagcguc gacacucugg uggacgauug gugucucgga cuuuccaacc cugacaacaa       300
cguggagguu gguugggcac uucgucugag ggaccgcuuu ggucuuccuc ccgccucuga       360
gcccacaagg cucaguggug agagaugggu gcuuaaacaa cucaauggggu uagacccgga      420 gucguggaau guugaucugc aaagcguuuu cgaagacgcu caggaugacu uccaucggga       480
cuacgcccca aggaggaaug cccaaaucgc ucaaauugcg gcaacccuau ggcuuacaaa       540
gaccuuaguc gauaaggcuu uagcacgcca ucaggauuuu cgcaguuugc agugauuggg       600
gucgacgggc uagaggcuaa agcagugccu cuggcugcug gacuccgacu gcuuccgguu       660

-continued

```
ccgcggcccg gacaaagccg acggcugucu caaaccuugc uacucccuac uccccgugcu      720
caauuuguca aucacgcuaa cucagguaau aauuuggggc guguuuugac cacacgggug      780
augcaauaca aaggccgaga cccgauacua cccucccagg aagcccugcg caaacuuaac      840
cuucggauag gacaguugua uaagucuaga ccaccacug ucuaucccu gaguuaugau       900 ggguuucuua auuguuauga uggccgacag cguacucgcu acgcucaugc cgucgagcaa      960
uugaugggug ccgcucugac cccaaaagau gcgcgaguug agacguucau uaagaacgag     1020
aaguuugauu gguuguugaa gggagacgag gcugauccuc gugcaaucca accuaggaag     1080
ccgaaauauu uggccgaggu uggucgaugg uucaaaccgu uggagcgaau caucuacaag     1140
gaucucaguu ugcguuugua cggugauaac gcugaaccuu gcauugccaa aggcuuaaau     1200
gcauuggaau caggggcuac guugagacgu aaaugggaaa aguucgcuaa uccuguuugu     1260
guuucauugg augcuucucg uuucgaccug cacguaagug uuggcuuguu aaaguucacg     1320
cauaaauugu acaacuauua cugcaagucu cccacucuuc aacgauaucu caaauggaca     1380
cuccgcaacu ccgguaucgc cuccuguaag gaaaaaucau augcguauga gguugaaggc     1440
cguagaauga guggcgacau ggacaccgca uuaggcaacu guaucaucau gagauuauua     1500
acuugguuua ugcuuagcga acuuggcgug cggcaugagc uuuucgauaa uggugaugac     1560
uguuuuguua uuuguggaaa agaagacguu ccuagugcug agguaaucac gaacugguuu     1620
acggauuuug gguuguuggu uaagcuagaa ggcgucacgu ccguguuuga gcgcauugag     1680
uucugucaga ccucaccagu auggacugcg aggggauggc ugauguguag aaacaucaag     1740
ucauugagua aagauuuaac gaauguuaau ucgugcacug guucugccgu ugaauacacu     1800
cauugguuga aggcggtuggg caagugugga ucuauacuca augcuggugu gcccauauuu     1860
caguccuuuc acaacauguu ggucagguug ggcacgaauu cgcguauaga ucgcggggua     1920
uucuuuaggu guggacuugu uaaucucauu cugggaugga cagacaaccu gaaaguugag     1980
aucacuacuu ccgcucgucu uucuuuugaa guggcauucg ggaucacucc cggcaugcaa     2040
uuggcuauug agcaauuuua ugacucaguc gugggcccuc ugggcuaaaau aaaaucugua    2100 aaauggccaa uagaucuaag aaaggaauac gauuacggaa gcgcguggu cgaagaccaa      2160 ggcguccuag ggugaacaag gaacucggau uaccgaugac accguucaa acuagaaugg      2220 uucggucaac guugaccaag gagaccaaca uaccuucuac ugcaaauagc ggucgggagg     2280
cuguuugggc uuguuggcca aucaacuuua gugucuuucc gcaacuagcc ucacucguga     2340
auaaaccguu auacuggcgu gugucccagug ugcaaguugc aauggagccg gcgaugucua    2400 cuuccacccca acauuguggga guuggucuca guucuucugg ggccuucacu aacggugaug    2460
gguucgguaa cgcucuuuaag cucuugcguu cuuguaacua uacgcggcgc ucccccgugg    2520
gaggaaacgu gauggucaaa uggcccaucu gcaugcccuu cauucuuaac gaugaugcgc     2580
acaagaacac aggauuaacc gccuguguga ucauugcagu caccaauacu ggugugcuaa     2640
cuggucaauc uuggacggag auucuuuuga auguggagua uguaguggu gcauagacag      2700 ucugcgggcu uggaacgac gccccgcuag caacguacug cucuccuacc ggacugguag      2760
ccguuuaguu aucuuggagc gauagcacug ugagccucac ucaacgcgcg auggacugg     2820 cgagugcccc ucagagauuu gugaaacucu auagagcuau uucgcgagcc agaagggagg     2880
auggccaccu gguguaagcc agguauccccc gggggcuug uacucggggu cgcauuacug     2940
cuuagaccac aagguagggu ucgcaucuug gaacugaccc uaugaccuug ugggugcccu     3000
aaccggacug guagccguuu aauaucuugg agcgauuagc acgugugagc ccucacucaa     3060
```

-continued

```
cggcgcgauu ggacguggcg agugcccucc agaguaaucu gcagagcucc ggcagucgug    3120
ggaggcaagg ca                                                       3132
```

<210> SEQ ID NO 21
<211> LENGTH: 3275
<212> TYPE: RNA
<213> ORGANISM: Ficus carica
<220> FEATURE:
<221> NAME/KEY: misc_feature
<222> LOCATION: (1)..(3275)
<223> OTHER INFORMATION: Polynucleotide Sequence of Fig Tree iRNA ("iRNA
      relative 2" or "iRNA r2")

<400> SEQUENCE: 21

```
cucccacgac ugccggagcu cugcagaauu ccaccggggg uaccuggcuu acaccaggug     60
gccauccucc cuucuggcuc gcggaauagc ucuauagagu uucacaaauc ucugaggggc    120
acucgccacg uccaucgcgc guugagugag gcucacagug cuaucgcucc cagaauucgg    180
gauaaauaug gaagaaacuu cuuugcccaa agccugcugg aucaaaagcc aggcaggucu    240
ugcguacacc agcuaacuuu uccaaagggg uagugaaggc ugcguaccgg ugggucaaca    300
ugcccagagc caaauauguc agagaugucu ccacagaucu uggcauaguu gucgcugagc    360
cguuugcugc cgugcgccgu cagaugccuu cgauaagcag ccuugcggag gaguugguaa    420
cacgccagag cgucgacacu cugguggacg auuggugucu cggacuuucc aacccugaca    480
acaacgugga gguugguugg gcacuucguc ugagggaccg cuuuggucuc ccucccgccu    540
cugagcccac aaggcucagu ggugagagau gggugcuuaa acaacucaau ggaguagacc    600
cggaaucuug gaaugacgac uaugcguucg aagacgcuca ggaggauuuu caacgggaau    660
acgucccggg aaggaaugcc cauauugcug caacugcggc aacucuaugg cugacaaaga    720
ccuuguauga caaggcuuua guucgccauc aggguuuucg caguuugcag ugauuggggu    780
cgacgggcug gaggcuaaag cagugccucc agcugcugga cuccgacugc uuccgguucc    840
gcggcccgga caaagccgac ggcugucuca gaccuuacua cuuccuacuc cccgugcuac    900
uuuugucaau caugcaaauu caggcaauaa ucuugagcgu guuuugacca cacgggugau    960
gcaauacaaa ggccgagacc cgauacuacc cucccaggaa gcccugcgca aacuuaaccu    1020
ucggauagga caguuguaua agucuagacc auccacuguc uauccccuga guuaugaugg    1080
guuucuuaau uguuaugaug gccgacagcg uacucgcuac gcucaugccg ucgagcaauu    1140
gaugggugcc gcucugaccc caaaagaugc gcgaguugag acguucauua agaacgagaa    1200
guuugauugg uuguugaagg gagacgaggc ugauccucgu gcaauccaac cuaggaagcc    1260
gaaauauuug gccgagguug gucgaugguu caaaccguug gagcgaauca ucuacaagga    1320
ucucaguuug cguuuguacg gugauaacgc ugaaccuugc auugccaaag gcuuaaaugc    1380
auuggaauca ggggcuacgu ugagacguaa augggaaaag uucgcuaauc cuguuugugu    1440
uucauuggau gcuucucguu ucgaccugca cguaagugu  ggcuuguuaa aguucacgca    1500
uaaauuguac gacuauuacu gcaagucucc cacucuucaa cgauaucuca aauggacacu    1560
ccgcaacucc gguaucgccu ccuguaagga aaaaucauau gcguaugagg uugaaggccg    1620
uagaaugagu ggcgacaugg acaccgcauu aggcaacugu aucaucauga cgauauuaac    1680
uugguuuuag cuuagcgaac uuggcgugcg gcaugagcuu uucgauaaug gugaugauug    1740 uuuuguucauu ugcgaagaaa aagacguacc uagccccgag acgaucauga acugguuugc    1800
ggauuuuggg uuuguggguua gguuagaagg cgucgugucc guguuugagc gcauugaguu    1860
```

```
cugccaaaca ucgccuauau ggacugaucg agguuggcug auguguagaa acaucaaguc      1920
uuugaguaag gaucuuacga acguuaauuc gugcacuggc uccacuguug aauacaccca      1980
uugguugaaa gcaguuggaa aguguggauc ggugcucaau gcgggugugc cuauauuuca      2040
gucauuucac aacauguuga ugcgauuggg uacgaauucg cguauagauc gcgggguauu      2100
cuuuaggugu ggacuuguua aucucauucg ugggauggac agacaaccug aaguugagau      2160
cacuacuucc gcucgucuuu cuuuugaagu ggcauucggg aucacucccg gcaugcaauu      2220
ggcuauugag caauuuuaug acucagucgu gggcccucug gguaaaauaa aaucuguaaa      2280
auggccaaua gaucuaagaa aggaauacga uuacggaagc gcgugguucg aagaccaagg      2340
cguccuaggg ugaacaagga acucggauua ccgaugacac cuguucaaac uagaaugguu      2400
cggucaacgu ugaccaagga gaccaacaua ccuucuacug caaauagcgg ucgggaggcu      2460
guuugggcuu guuggccaau caacuuuagu gucuuuccgc aacuagccuc acucgugaau      2520
aaaccguuau acuggcgugu guccagugug caaguugcaa uggagccugc aaugucuucu      2580
uccacccaac auuguggugu uggucucagu ucuucugggg ccuucacaua acggugaugg      2640
guucgguaac gucuuuaagc ucuugcguuc uuguaacuau acgcggcgcu cucccguggg      2700
aggaaacgug auggucaaau ggccuaucug caugcccuuc auucuuaacg augaugcgca      2760
caagaacaca ggauuaaccg ccugugugau cauugcaguc accaauacug ugugcuaac       2820 uggucaaucu uggacggaga uucuguugaa uguggaguau acgccccgcu agcaucguac      2880
ugcucuccua ccggacuggu agccguuuag uuaucuugga gugauagcac uguggggcca      2940
cauuugacgc gcauggacg cagacaaugu cccuccacag auuugugaau cucuauggag       3000
cguuaaccuc ggcucucua uagcuugucc gaacaggaaa uggacauaaa auaauugcug       3060
uuccaacacg uuguguuggu aaagaaguua uagauguggu gcgccagaca aguggauggc      3120
aaccuggagu aauccaggcg cucuggggggg cuuauacucg gagugcauua cugcuuuaga     3180
ccguuaaucu caagaaccau gugugucgca ugggggaggau uaacggcgcc caauucccuu     3240
guuaguuuag guacgccuug gucuucgaac cacgc                                 3275
```

<210> SEQ ID NO 22
<211> LENGTH: 2985
<212> TYPE: RNA
<213> ORGANISM: Ficus carica
<220> FEATURE:
<221> NAME/KEY: misc_feature
<222> LOCATION: (1)..(2985)
<223> OTHER INFORMATION: Polynucleotide Sequence of Fig Tree iRNA ("iRNA relative 3" or "iRNA r3")

<400> SEQUENCE: 22

```
gggguaaaua uggagaacca gcacacccau guuugcccac ggucguuccu gcgaaccugc        60
agggcgaucc ucgcggcucc agccaacuac ggucgugaug uggucaaaau cgccuacaaa       120
ugggcaucac gaaaccccgc caccgccccc cgaagugucc gagaauccau cggggucguu       180
gucggaagcg cuguggacuu cuugagcgcu ccucgcaagc guuuagaaga ccgcgcagag       240
caguuggugc aagacgaccg ggucgaccgg auccuccgcg aguggggagcu aggaaccgcu       300 gacucccgaa uuccggaagu ugagugggca uaccgucugc gcgaccgcuu cggcgucgug       360
uccgccagcg agccugcuag gcaaacuggu gagagguggg ugcucaagca acuagaggga       420
uuggaggggg gggaguuccg cugcauaccc auuugagccau ucuuugguga ugcaccggcc      480
cccguccaua gcccugggag caacagcgug auuugcugcua uugcggcgac ccuuuggaug      540
```

-continued

```
acgccuacccc gccuugaccg ggcguugaga cgucaccagg guuuucgcaa cuagcgguga      600
ucggagucga cggagugucu gcuuuagcgg ugcaggcauc uucugaacuc cgaccgcuac      660
ggguugggcg accccgucaa agucgacguc guucgugguc ucgacuaug ccagcacccca     720 aguccuguuu cgugaaccac gcuaacucug accacaaucu caaaacgguc auggaaaaca      780
gggugcucaa guacaaaggc caagaacccg caaagccccg gguagaagcc uauaagcagc      840
ucuaugaaag gauacgaccg cgauaucguu cucuaccuga cacgggcuau ccucuaucau     900
augauggcuu ccucaagugc uacuccggac guaggcgaac acgauacgaa caggccguccc     960 aggaguugag aaacgcgcca cucacacccg aagaugcugu cguuccacg uucaucaaga     1020 acgagaaauu cgauuggcuc caaaagaaag aacuugcgga ucccagagcu auccaaccuc     1080
ggaaaccgaa auaccuggcc gaaguuggga ggugguucaa gccucuggag cacauaaugu     1140
auaaagacuu ggcaaaacgg uuguacgguc aggaugcguu gccuugcaua gcgaaagggc     1200
ugaacgcuag agaaacggcu gaagugcucc gagccaaaug ggacaaguuc gcuucucccg     1260
uuugcgucuc gcuggaugcc agucgguucg aucugcaugu aagccugac gcauugcggu      1320 uuacgcaccg ccuguaccac aaguauugcc aaagucggca acuccgcaag uaccuagaau     1380
ggacgcugag aaacgcuggc gucgccucau guccugaaag cgcuuaucag uaugagguug     1440
aggggagacg caugagugg gacauggaca ccgcacucgg caacugcgua cuuaugcucu     1500
gcuugacaug gaacuuccuc gaucaacaua acaucaagca ugagauaaug gacaacggag     1560
augacugcuu guucaucugu gaagcugccg augugccaac cgacaagcaa aucauggacu     1620
acuaccucga cuuugggguc guggnucggu uggaaggaaa ggugucugug uucgagcgaa     1680 uagaguucg ucaaaccagu ccggguguuga cugcuaaugg auggcguaug guuagaaauu      1740
ugaaguccau ugcgaaggac cucugcaaug ugaacauggc gacuggguca cucagugaau     1800
acacugcgug gcuuaaagcc gugggaaucu gugguagaau ccugaacgau ggggguuccaa    1860 ucuucuccgc cuuccacaac augcuggugc gacauggaac gaacucacga auagauagag     1920
cgguguucug ggaaugugga cugacaaacu ugaucaaagg caugaguuuc gagcaacugg      1980
aaaucacugu cgcugcgcgc gaguccuuuu aucuggcaua cgguaucaca ccggcgagac     2040
aacucgcgau ugaagaguau uacgacucac uccagggccc ggugggguaaa auacaacuuc     2100 augaauggcc acuacaacuc aaagaggaau acgcgugcgg cgccgagugg uucgaaggag     2160
acggcgagcg ggcuugaggc ccgcuggcuu gcccuucgug cccggcagcu cucgcacggu     2220
ucggacugcg cucgucccg agaaccacuu gccgaugucc ucggcacagu ugggucaaga      2280
ggccguugcg uauucuaucc cgugcaaugu ucgaaacaug ccuacgaucc ugacucucgc     2340
caccaucccc cucuauuggc guacaccgc caucacuguc gcgauggagc cugcaaaguc      2400
cacaucgacc caaauugccg gugugggggaa ugcugauuca uuucagucug ccaccuacaa     2460
cgguuuuggg aacguguuua agaaaaugcg cgcuuugaau uucgagac gcucggcgcc       2520 cggaggcaau cuucagguac gcuggccuau caauauggac uggaucuccg cauccgacac     2580
ggacaaggau agcacaaaag ugcccucgcu auucuuugcc gugaccaacc caggugugau     2640
cgaaaccaaa caaggggaca gugaggccug guuggaaugg gaguuggagc uggaguacau     2700
aguuggaggc uaggaacgac ugcccgcuug agaucgacuc ucccgugggu agguaccacc     2760
cacucagcug ugucagccgg uuggagaaac ucuggcgcga uagcacuguu ggccccugcc     2820 uagcguguc uguggggaaag ccccaacaga uuugugaaac acuggaguug ucgacccgcg     2880
```

-continued

```
agacgugcgg cucgaguugu cgcuuccccg ugagggggggc ugccggggg uagagaaaua    2940 uucccgguau uuauccgcua agaccuacgc gcgacgaaac uggcg               2985

<210> SEQ ID NO 23
<211> LENGTH: 4252
<212> TYPE: RNA
<213> ORGANISM: Unknown
<220> FEATURE:
<223> OTHER INFORMATION: Pea Enation Mosaic Virus 2 (PEMV2)

<400> SEQUENCE: 23
ggguauuuau agagaucagu augaacugug ucgcuaggau caagcggugg uucacaccug       60
acuucacccc uggcgagggc gugaagucua gagcucaacu ggaaagagag cuggauccca      120
ccugggcgcu ucucgugugc caagaacgag cgcgucguga ugcugacagu auugcuaaug      180
agugguacga gggcagcaug gagugcaacc uccuuauccc ucggcccaca accgaggaug      240
uauuuggccc cuccaucgcc ccugagccug uggcucuagu ggaggaaacu acccguuccc      300
gcgcgccgug cguggauguc ccugccgagg aguccuguaa gucagcggag auugauccg       360 uugaucucgc caaguucgac ucccuccauc gucgccuguu ggcugaagcc aacccuugca      420
gggaaauggu ucugugggug ccuccuggcc uaccagcaga gcgcgacguc cugcccaggg      480 cacgugggu gauaaugauc cccgaagucc cugccucugc acauaccuug uccgugaagg       540
uuauggaggc ugugcgguug gcacaggaag ucuuggcauc ccuugccaag agggccuuag      600
agaaaagguc uacaccaacc cuuaccgccc aggcccagcc agaggcuacc cugucggggu      660
gcgacuaccc guaucaggag acuggagcag cagccgcgug gauaacgccu ggcugcauug      720
ccauggagcu cagagccaaa uuuggcgucu gcaaacgcac ccccgcaaac uuagagaugg      780
ggagucgcgu cgcccgcgag cuccugcggg auaacugugu cacuugcagg agaccacgu       840 gguacaccag ugccauugcu guggaccugu gguugacccc gaccgucguc gaccuggccu      900
guggccggcg agcggcggau uuuugguagg ggcugugcug ccucggcugg gggaagacac      960
cagugugcgg uuugacaacc ugcacccccag caucgaggua aucaaggcgg cuaggccccg     1020
cccaacccag aggaugucgu uccaaaucga cguugugcgu ccucuuggag auuuuggugu     1080
gcacaacaac ucccuuguua accuagccag gggaauuaau gaaagggugu ucuacacgga     1140
caaugcuagg acagaacccc uccagccuaa gguucccuuc cccucaucac gggagcuaaa     1200
aaccuucaga gucacccuu ggaccaugga uaggguugug gagaguuaca caggguccca      1260
gcgcacucgc uaugcuaacg cgcgggacag cauauuuaucc aacccucuga gucccaaaga     1320 ugcgcgggc aagacguuug ucaaagcuga aaagauaaau uucacagcca aaccugaccc      1380
cgccccucgu gugauacagc cuagggaucc acgauucaac auuguccugg cuaaauacau     1440
caagccuuug gagccaaugu uguacaaagc acuggggaaa cuuuacaagu accccgcagu     1500
ugcuaagggg uuuaacgcgg uugagacggg ggagaucauc gccggcaagu ggcggugcuu     1560
caaagauccu gucgucgugg gauuagacgc uucccgauuu gaucagcaug uaucugucga     1620
ggcguugcag uucacccacg cgguguacag aggguucauc aagucacggg aguuuaacaa     1680
ccuccuacag augauguaca ccaaccgugg ccuaggguucc gcuaaggacg gauucguccg     1740
uuacaagguu aaagguagac gcaugagcgg ugacauggac accuccuugg gcaacugugu     1800
gcucauggug uugcucacca ggaaccuuug caagguucua ggcaucccgc acgagcucuu     1860
caacaauggu gaugauugca ucgucuuuuu cgaucguugc cacuuggaga aguucaacaa     1920
ugcugucaag acuuauuuug cggaccuagg guuuaagaug aagguggaac cgccgguuga    1980
```

-continued

```
cguguuggag aaaauagagu ucugccaaac gcagccuauc uaugacgggg agaaguggcg      2040
caccgugcgu ugcaucucga guaucggaaa agauugcuca uccguuauua guugggacca      2100
auuggagggg ugguggaaug ccaucgccca gaguggucug gcugugugug gcggaaugcc      2160
gauauacacg ucguucuacc gguggcuagc acgggccggu aagaguggga ccaaguguca      2220
gucacacccc uuguggaaaa acgaggggguu gaauugguac aggaugggga uggaccuuuc      2280
ucaugagguu aauguuaccc cucaggcgcg ccugucuuuc uucgcggguu uugguauuuc      2340 cccccccgaug caggucgcca uugaggcgcu guaugacaag cugccuccac cgucccccca      2400
ccaugguccu ccgguuaagg cguuaacaca gcgaguguuc accaauuauu ucacgccgga      2460
aagcgccugu guuagcauga gcacgaauga agacaacaaa ucugacuuug cuguuuacgg      2520
cccugugccu acagugaugu cucuuugugc ucaguguuag gcucuuaaau uuuagcgaug      2580
gcgugacacg guuacacccu gaauugacag gguacagauc aagggaagcc ggggagucac      2640
caacccaccc ugaaucgaca gggcaaaaag ggaagccggg caccgcccac guggaaucga      2700
ccacgucacc uuuucgcguc gacuaugccg ucaacacccu uucggcccgc cagccuagga      2760
caauggcggu agggaaauau augacgauaa ucauuaaugu caauaacgac gagcgcaagc      2820
aaccagaagg agcuacuggc agcucuguac ggcgaggga caauaaaaga acucgaggaa       2880
acaaaccucg gagucaucac cccgguucgc gcgaacgaaa agguuacaau caccccucuc      2940
cuacccccaa aaacucaaag cagggucagc uccguacuga agcgguucag gagcacccga      3000
aacacggggg gacugcuuuc cguagagaaa gugguggua guucacccc ucacaucccc        3060 gacgacgugc uaggagaggu ggagauaugg cuccacgaca gcauccuccc ccaccucggg      3120
agcgucggac caagacugaa acucaagcug agcgaagggc ccaagcucuu agcguucuac      3180
ccacccuacu cgauugcauu gggggacucg aucucgggcc agccgagguc cuucuccauu      3240
gucaccgagc uguucgaagg caacuucgca ccggggugca gcccauucag ccuguuccuc      3300
auguggaguc cacgcaucga agcagugacc cacaacuacu ugagucgucc accacgugcu      3360
cugccaauuu gcagaacgau ggugcggac gcguuaucgg agguggcauc ccaacagcaa       3420
uaccugaagg gagcgauguc gaacagguau gccaugccuc ucacuacggg ugauggccag      3480
cauagagcca ugaaggggg ucccagugcc cuuccaccaa cggggugug uacccaggcu        3540 ucuaagugag gcuucgcuuc ccgccggaag accgcggcgg uucuguuccu cccacaggag      3600
uacggcaaca acccaccuug ggaaaguggg gaccccagca cuaacuccuu uaacuaggcg      3660
ggcguguugg uuacaguagg aggggacagu gcgcaucgaa acugagcccc accacaacuc      3720
ucauccacgg ggugguuggg acgcaggugu cggagggauc gccagcccuc aggauaguga      3780
gcucccgcag agggauaagc uaucucccug cgacguagug guagaacacg ugggauaggg      3840
gaugaccuug ucgaccgguu aucggucccc ugcuccuucg agcuggcaag gcgcucacag      3900
guucuacacu gcuacuaaag uugguggugg augucucgcc caaaaagauc acaaacgcgc       3960
gggacaaggu cccuuccacc uucgccgggu aaggcuagag ucagcgcugc augacuauaa      4020
cuugcggccg auccaguugc acgacuggug uccccuca gugucucggu ugucugccga        4080
gugggcggug ucggauucc accacacccu gccacgaggu gcguggagac uuggccaguc       4140
uaggcucguc guaauuaguu gcagcgacgu uaaucaaccc guccgggcau auaauaggac      4200
cgguugugcu ucuccuccc uucuuagcca ggugguuacc ucccuggcgc cc             4252
```

<210> SEQ ID NO 24

```
<211> LENGTH: 313
<212> TYPE: RNA
<213> ORGANISM: Unknown
<220> FEATURE:
<223> OTHER INFORMATION: Pea Enation Mosaic Virus 2 (PEMV2)
<220> FEATURE:
<221> NAME/KEY: misc_feature
<222> LOCATION: (1)..(313)
<223> OTHER INFORMATION: Intergenic Plus Region of PEMV2

<400> SEQUENCE: 24
guuagcauga gcacgaauga agacaacaaa ucugacuuug cuguuuacgg cccugugccu        60
acagugaugu cucuuugugc ucaguguuag gcucuuaaau uuuagcgaug gcgugacacg       120
guuacacccu gaauugacag gguacagauc aagggaagcc ggggagucac caacccaccc       180
ugaaucgaca gggcaaaaag ggaagccggg caccgcccac guggaaucga ccacgucacc       240
uuuucgcguc gacuaugccg ucaacacccu uucggcccgc cagccuagga caauggcggu       300
agggaaauau aug                                                         313

<210> SEQ ID NO 25
<211> LENGTH: 139
<212> TYPE: RNA
<213> ORGANISM: Unknown
<220> FEATURE:
<223> OTHER INFORMATION: Pea Enation Mosaic Virus 2 (PEMV2)
<220> FEATURE:
<221> NAME/KEY: misc_feature
<222> LOCATION: (1)..(139)
<223> OTHER INFORMATION: Polynucleotide Sequence of Recoding Frameshift
      Sites of PEMV2

<400> SEQUENCE: 25
gaccgucguc gaccuggccu guggccggcg agcggcggau uuuugguagg ggcugugcug        60
ccucggcugg gggaagacac cagugugcgg uuugacaacc ugcaccccag caucgaggua       120
aucaaggcgg cuaggcccc                                                   139

<210> SEQ ID NO 26
<211> LENGTH: 65
<212> TYPE: DNA
<213> ORGANISM: Arabidopsis thaliana
<220> FEATURE:
<221> NAME/KEY: misc_feature
<222> LOCATION: (1)..(65)
<223> OTHER INFORMATION: Sequence of Insertion Region

<400> SEQUENCE: 26
taggcctcga cacgggaagg tagctgtccc ggcactgggt tgcacatatt ccgtgccgac        60
gccac                                                                   65

<210> SEQ ID NO 27
<211> LENGTH: 43
<212> TYPE: DNA
<213> ORGANISM: Arabidopsis thaliana
<220> FEATURE:
<221> NAME/KEY: misc_feature
<222> LOCATION: (1)..(43)
<223> OTHER INFORMATION: Insertion Sequence Region

<400> SEQUENCE: 27
ccggcctcga cacgggaagg tagctattcc gtgccgacgc cgt                          43

<210> SEQ ID NO 28

<400> SEQUENCE: 28
```

```
000

<210> SEQ ID NO 29

<400> SEQUENCE: 29

000

<210> SEQ ID NO 30
<211> LENGTH: 10
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(10)
<223> OTHER INFORMATION: Lock and Dock Sequence

<400> SEQUENCE: 30
guccuaaguc                                                          10

<210> SEQ ID NO 31
<211> LENGTH: 14
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(14)
<223> OTHER INFORMATION: Lock and Dock Sequence

<400> SEQUENCE: 31 cagggggaaac uuug                                                    14

<210> SEQ ID NO 32
<211> LENGTH: 31
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(31)
<223> OTHER INFORMATION: Scaffold Comprising Docked Tetraloop

<400> SEQUENCE: 32
cauuagcuaa ggaugaaagu cuaugcuaau g                                  31

<210> SEQ ID NO 33
<211> LENGTH: 57
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(57)
<223> OTHER INFORMATION: Lock and Dock Structure

<400> SEQUENCE: 33
gcaccuaagg cgucaggguc uagacccugc ucaggggaaa cuuugucgcu auggugc      57

<210> SEQ ID NO 34
<211> LENGTH: 47
<212> TYPE: RNA
<213> ORGANISM: Unknown
```

```
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(47)
<223> OTHER INFORMATION: Sequence of Insertion into CYVaV

<400> SEQUENCE: 34
ggcuaguuaa ucucauucgu gggauggaca ggcagccuga cguugac                   47

<210> SEQ ID NO 35
<211> LENGTH: 30
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(30)
<223> OTHER INFORMATION: Sequence of CYVaV Insertion (Unmodified; U at
      Positions 3, 6, 8, 14, 17 and 29)

<400> SEQUENCE: 35
guuaauguag gugucuuucc guaucuaguc                                       30

<210> SEQ ID NO 36
<211> LENGTH: 30
<212> TYPE: RNA
<213> ORGANISM: Unknown
<220> FEATURE:
<223> OTHER INFORMATION: Citrus Yellow Vein associated Virus (CYVaV)
<220> FEATURE:
<221> NAME/KEY: misc_feature
<222> LOCATION: (1)..(30)
<223> OTHER INFORMATION: Sequence of CYVaV Insertion (Modified; G at
      Positions 3, 6, 8, 14, 17 and 29)

<400> SEQUENCE: 36
gucaacgcag gugccugucc guaucuagcc                                       30

<210> SEQ ID NO 37
<211> LENGTH: 66
<212> TYPE: RNA
<213> ORGANISM: Artificial Sequence
<220> FEATURE:
<223> OTHER INFORMATION: Polynucleotide Sequence targeting GFP

<400> SEQUENCE: 37
ugaagcggca cgacuucuuc aagagcgcca gaauucuggc gcucuugaag aagucgugcc      60
gcuuca                                                                 66

<210> SEQ ID NO 38
<211> LENGTH: 48
<212> TYPE: RNA
<213> ORGANISM: Artificial Sequence
<220> FEATURE:
<223> OTHER INFORMATION: Polynucleotide Sequence targeting conserved CTV
      sequence

<400> SEQUENCE: 38
uccguggacg ucauguguaa ggguacccuu acacaugacg uccacgga                   48

<210> SEQ ID NO 39
<211> LENGTH: 21
<212> TYPE: RNA
<213> ORGANISM: Artificial Sequence
<220> FEATURE:
<223> OTHER INFORMATION: Polynucleotide Sequence complementary to CTV18
```

-continued

```
       sequence

<400> SEQUENCE: 39
cuuacacaug acguccacgg a                                         21

<210> SEQ ID NO 40
<211> LENGTH: 54
<212> TYPE: RNA
<213> ORGANISM: Artificial Sequence
<220> FEATURE:
<223> OTHER INFORMATION: Polynucleotide Sequence of Hairpin targeting
      CTV

<400> SEQUENCE: 40
ggaagugaug gacgaaauua augaccaauc auuaauuucg uccaucacuu ccag          54

<210> SEQ ID NO 41
<211> LENGTH: 24
<212> TYPE: RNA
<213> ORGANISM: Artificial Sequence
<220> FEATURE:
<223> OTHER INFORMATION: Polynucleotide Sequence complementary to CTV6
      and variants

<400> SEQUENCE: 41
ucauuaauuu cguccaucac uucc                                      24

<210> SEQ ID NO 42
<211> LENGTH: 57
<212> TYPE: RNA
<213> ORGANISM: Artificial Sequence
<220> FEATURE:
<223> OTHER INFORMATION: Polynucleotide Sequence of Lock and Dock 1
      (L&D1)

<400> SEQUENCE: 42
gcgauaugga uucagggacu agucccugcu caggggaaac uuuguguccu aagucgc       57

<210> SEQ ID NO 43
<211> LENGTH: 77
<212> TYPE: RNA
<213> ORGANISM: Artificial Sequence
<220> FEATURE:
<223> OTHER INFORMATION: Polynucleotide Sequence of Lock and Dock 2
      (L&D2)

<400> SEQUENCE: 43
gcgauaugga ucaggacuag uccugucacc cucacuucgg uguccagggg aaacuuugug     60
ggugaguccu aagucgc                                              77

<210> SEQ ID NO 44
<211> LENGTH: 60
<212> TYPE: DNA
<213> ORGANISM: Artificial Sequence
<220> FEATURE:
<223> OTHER INFORMATION: Polynucleotide Sequence of cDNA portion

<400> SEQUENCE: 44
agttaatgta ggtgtctttc ctgaagcggc acgacttctt caagagcgcc agtatctagt    60

<210> SEQ ID NO 45
<211> LENGTH: 30
<212> TYPE: DNA
<213> ORGANISM: Artificial Sequence
<220> FEATURE:
<223> OTHER INFORMATION: Polynucleotide Sequence of cDNA portion
```

```
<400> SEQUENCE: 45
agttaatgta ggtgtctttc ctgaagcggc                                    30

<210> SEQ ID NO 46
<211> LENGTH: 11
<212> TYPE: DNA
<213> ORGANISM: Artificial Sequence
<220> FEATURE:
<223> OTHER INFORMATION: Polynucleotide Sequence of cDNA portion

<400> SEQUENCE: 46
cagtatctag t                                                        11

<210> SEQ ID NO 47
<211> LENGTH: 120
<212> TYPE: DNA
<213> ORGANISM: Artificial Sequence
<220> FEATURE:
<223> OTHER INFORMATION: Polynucleotide Sequence of cDNA portion

<400> SEQUENCE: 47
agttaatgta ggtgtctttc cgcgatatgg attcagggac ttgaagcggc acgacttctt    60
caagagcgcc aagtccctgc tcagggggaaa ctttgtgtcc taagtcgcgt atctagtcac   120

<210> SEQ ID NO 48
<211> LENGTH: 120
<212> TYPE: DNA
<213> ORGANISM: Artificial Sequence
<220> FEATURE:
<223> OTHER INFORMATION: Sequence of cDNA portion with L&D1 and hairpin
      insert

<400> SEQUENCE: 48
agttaatgta ggtgtctttc cgcgatatgg attcagggac ttgaagcggc acgacttctt    60
caagagcgcc aagtccctgc tcagggggaaa ctttgtgtcc taagtcgcgt atctagtcac   120

<210> SEQ ID NO 49
<211> LENGTH: 30
<212> TYPE: RNA
<213> ORGANISM: Artificial Sequence
<220> FEATURE:
<223> OTHER INFORMATION: Polynucleotide Sequence of Hairpin targeting
      GFP

<400> SEQUENCE: 49
ugaagcggca cgacuucuuc aagagcgcca                                    30

<210> SEQ ID NO 50
<211> LENGTH: 52
<212> TYPE: DNA
<213> ORGANISM: Artificial Sequence
<220> FEATURE:
<223> OTHER INFORMATION: Polynucleotide Sequence of cDNA portion

<400> SEQUENCE: 50
tgatacctgt tcagaatagg attgctcgag cttcgttggt tagggtaact ca            52

<210> SEQ ID NO 51
<211> LENGTH: 59
<212> TYPE: DNA
<213> ORGANISM: Artificial Sequence
<220> FEATURE:
<223> OTHER INFORMATION: Polynucleotide Sequence of cDNA portion
```

<400> SEQUENCE: 51
gcgatatgga ttcagggact agtccctgct caggggaaac tttgtgtcct aagtcgcac         59

<210> SEQ ID NO 52

<400> SEQUENCE: 52

000

<210> SEQ ID NO 53
<211> LENGTH: 180
<212> TYPE: DNA
<213> ORGANISM: Artificial Sequence
<220> FEATURE:
<223> OTHER INFORMATION: Sequence of cDNA portion with Lock and Dock
      construct

<400> SEQUENCE: 53
aatagggtca ttggtttacc gatgatacct gttcagaata ggattgctcg agcttcgttg         60
gttagggtaa ctcacatacc ttcttccata gcgatatgga ttcagggact agtccctgct        120
caggggaaac tttgtgtcct aagtcgcact ggaaaaggtc gtgtgagcaa cctaaccagt        180

<210> SEQ ID NO 54
<211> LENGTH: 51
<212> TYPE: DNA
<213> ORGANISM: Artificial Sequence
<220> FEATURE:
<223> OTHER INFORMATION: Polynucleotide Sequence of cDNA portion

<400> SEQUENCE: 54
gatacctgtt cagaatagga ttgctcgagc ttcgttggtt agggtaactc a                  51

<210> SEQ ID NO 55
<211> LENGTH: 89
<212> TYPE: DNA
<213> ORGANISM: Artificial Sequence
<220> FEATURE:
<223> OTHER INFORMATION: Polynucleotide Sequence of cDNA portion

<400> SEQUENCE: 55
gcgatatgga ttcagggact tgatgttgga tccatcctat gagccttttc agtccctgct         60
caggggaaac tttgtgtcct aagtcgcac                                           89

<210> SEQ ID NO 56
<211> LENGTH: 39
<212> TYPE: DNA
<213> ORGANISM: Artificial Sequence
<220> FEATURE:
<223> OTHER INFORMATION: Polynucleotide Sequence of cDNA portion

<400> SEQUENCE: 56
ctaaccagtt aatgtaggtg tctttccgta tctagtcac                                39

<210> SEQ ID NO 57
<211> LENGTH: 110
<212> TYPE: DNA
<213> ORGANISM: Artificial Sequence
<220> FEATURE:
<223> OTHER INFORMATION: Polynucleotide Sequence of contruct portion

<400> SEQUENCE: 57
aatagggtca ttggtttacc gatgatacct gttcagaata ggattgctcg agcttcgttg         60
gttagggtaa ctcacatacc ttcttccata gcgatatgga ttcagggact                   110

```
<210> SEQ ID NO 58
<211> LENGTH: 100
<212> TYPE: DNA
<213> ORGANISM: Artificial Sequence
<220> FEATURE:
<223> OTHER INFORMATION: Polynucleotide Sequence of construct portion

<400> SEQUENCE: 58
agtccctgct caggggaaac tttgtgtcct aagtcgcact ggaaaaggtc gtgtgagcaa          60
cctaaccagt taatgtaggt gtctttccgt atctagtcac                             100

<210> SEQ ID NO 59
<211> LENGTH: 30
<212> TYPE: RNA
<213> ORGANISM: Artificial Sequence
<220> FEATURE:
<223> OTHER INFORMATION: Polynucleotide Sequence of Callose Synthase 7
      siRNA that targets Callose Synthase

<400> SEQUENCE: 59
ugauguugga uccauccuau gagccuuuuc                                          30

<210> SEQ ID NO 60
<211> LENGTH: 52
<212> TYPE: RNA
<213> ORGANISM: Artificial Sequence
<220> FEATURE:
<223> OTHER INFORMATION: Polynucleotide Sequence of Hairpin targeting
      CTV6

<400> SEQUENCE: 60
ggaagugaug gacgaaauua augaccaauc auuaauuucg uccaucacuu cc                 52

<210> SEQ ID NO 61
<211> LENGTH: 63
<212> TYPE: RNA
<213> ORGANISM: Artificial Sequence
<220> FEATURE:
<223> OTHER INFORMATION: Polynucleotide Sequence of Lock and Dock 3
      (L&D3)

<400> SEQUENCE: 61
gcggcgauau ggauucaggg acuagucccu gcucagggga aacuuugugu ccuaagucgc         60
cgc                                                                      63

<210> SEQ ID NO 62
<211> LENGTH: 89
<212> TYPE: DNA
<213> ORGANISM: Artificial Sequence
<220> FEATURE:
<223> OTHER INFORMATION: Polynucleotide Sequence of cDNA constuct
      containing L&D1

<400> SEQUENCE: 62
tgtaggtgtc tttccgcgat atggattcag ggactagtcc ctgctcaggg gaaactttgt         60
gtcctaagtc gcgtatctag tcacgatgg                                          89

<210> SEQ ID NO 63
<211> LENGTH: 180
<212> TYPE: DNA
<213> ORGANISM: Artificial Sequence
<220> FEATURE:
<223> OTHER INFORMATION: Polynucleotide Sequence of cDNA construct
      portion with L&D3
```

-continued

<400> SEQUENCE: 63
ttccataact ggaaaaggtc gtgtgagcaa cctaaccagt taatgtaggt gtctttccgc        60
ggcgatatgg attcagggac tagtccctgc tcaggggaaa ctttgtgtcc taagtcgccg       120
cgtatctagt cacgatggta agcaacccgt ttatctgtac ggcgctcacc cgtgggtaga       180

<210> SEQ ID NO 64
<211> LENGTH: 23
<212> TYPE: RNA
<213> ORGANISM: Artificial Sequence
<220> FEATURE:
<223> OTHER INFORMATION: Polynucleotide Sequence of CYVaV portion

<400> SEQUENCE: 64
cagaccuuug uuacuuccaa cac                                                 23

<210> SEQ ID NO 65
<211> LENGTH: 29
<212> TYPE: RNA
<213> ORGANISM: Artificial Sequence
<220> FEATURE:
<223> OTHER INFORMATION: Polynucleotide Sequence of CYVaV portion

<400> SEQUENCE: 65
cuggauuucc uguguuuugg aaguggaag                                           29

<210> SEQ ID NO 66
<211> LENGTH: 21
<212> TYPE: RNA
<213> ORGANISM: Artificial Sequence
<220> FEATURE:
<223> OTHER INFORMATION: Polynucleotide Sequence of CTV portion

<400> SEQUENCE: 66
uccguggacg ucauguguaa g                                                   21

<210> SEQ ID NO 67
<211> LENGTH: 24
<212> TYPE: RNA
<213> ORGANISM: Artificial Sequence
<220> FEATURE:
<223> OTHER INFORMATION: Polynucleotide Sequence of CTV portion

<400> SEQUENCE: 67
ggaagugaug gacgaaauua auga                                                24

PLANT VECTORS, COMPOSITIONS AND USES RELATING THERETO

STATEMENT REGARDING FEDERALLY SPONSORED RESEARCH OR DEVELOPMENT

This invention was made with government support under Grant No. AP17PPQS and T00C118 awarded by the United States Department of Agriculture (USDA), and under Grant No. 1411836 awarded by the National Science Foundation (NSF). The United States government has certain rights in this invention.

CROSS-REFERENCE TO RELATED APPLICATIONS

This application is based on International Application No. PCT/US2019/060945, filed Nov. 12, 2019, which application is incorporated herein by reference in its entirety and to which priority is claimed. This application is also based on U.S. Provisional Application No. 63/023,712, filed May 12, 2020, which application is incorporated herein by reference in its entirety and to which priority, and the benefit of, is claimed.

REFERENCE TO SEQUENCE LISTING

This application includes one or more Sequence Listings pursuant to 37 C.F.R. 1.821 et seq., which are disclosed in computer-readable media (file name: Corrected_2105_0071 PCT2_ST25, created on Sep. 1, 2022, and having a size of 45,806 bytes), which file is herein incorporated by reference in its entirety.

FIELD OF THE INVENTION

The present disclosure relates to an RNA vector suitable for introducing a therapeutic agent, such as a peptide, a protein or a small RNA, into a host. In some examples the host is a plant, wherein movement thereof may be substantially limited to the phloem and targeted to control or manage a plant disease or condition.

BACKGROUND OF THE INVENTION

Both general and highly targeted anti-microbial agents have been developed for animals (e.g., humans) whose circulatory systems provide a delivery system for widespread application throughout the animal. In contrast, much less research has been conducted to develop general or targeted therapeutic agents for non-genetically modified plants since lack of a simplified circulatory system complicates delivery throughout the host plant. This is especially problematic in large, long-lived trees (e.g., citrus), where injection of anti-microbial agents may be rapidly diluted. As a result, few solutions exist for treating systemic plant infections or conditions beyond external application of pesticides, e.g., to control the pathogen's vector during the growing season, foliar applications to strengthen a plant's health in general, or expensive, short-duration injection of agents targeting the pathogen or vector.

Particularly concerning are diseases and conditions affecting the citrus industry. Huanglongbing (HLB), also known as Citrus Greening, is the most serious citrus disease globally. HLB is associated with three species of the bacterium Candidatus liberibacter spp. (asiaticus, africanus, and americanus) and is transmitted by two psyllid species, Asian citrus psyllid (ACP) (Diaphorina citri, Kuwayama) and African citrus psyllid (Trioza erytreae, Del Guercio). HLB is graft-transmissible and spreads naturally when a bacteria-containing psyllid feeds on a citrus tree and deposits the pathogenic bacteria into the phloem where the bacteria reproduce. Once a tree is infected, there is no cure. While the diseased fruit pose no health threat to humans, HLB has devastated millions of acres of citrus groves throughout the world. In the United States alone, ACP and CL asiaticus (CLas) have decimated the Florida citrus industry, causing billions of dollars of crop losses within a very short time span. Moreover, HLB has spread into every citrus producing region in the United States. Most infected trees die within a few years after infection, and fruit develops misshapen and off flavored and thus is unsuitable for consumption. According to the United States Department of Agriculture (USDA), the entire citrus industry is at substantial risk.

Consideration of plant physiology aids in the development and implementation of strategies for managing plant diseases and conditions. The vascular system of plants is the key conduit for sugars and amino acids, as well as signaling molecules such as small ribonucleic acids (RNAs), proteins, peptides and hormones, which are required for a large number of developmental processes and responses to biotic and abiotic stress (FIG. 1) (Lee, J. Y. and Frank, M. (2018), Plasmodesmata in phloem: different gateways for different cargoes, Curr Opin Plant Biol 43:119-124; Tugeon, R. and Wolf, S. (2009), Phloem Transport: Cellular Pathways and Molecular Trafficking, Ann Rev Plant Biol 60:207-221). Messenger RNAs (mRNAs) comprise a portion of these signaling molecules, and thousands of companion cell mRNAs can be isolated from neighboring enucleated sieve elements, where they are transported bidirectionally by osmotically generated hydrostatic pressure from source (sugar generating) tissue to sink (sugar utilizing) tissue such as roots and shoot tips (Folimonova, S. Y. and Tilsner, J. (2018), Hitchhikers, highway tools and roadworks: the interactions of plant viruses with the phloem, Curr Opin Plant Biol 43:82-88; Ham, B. K. and Lucas, W. J. (2017), Phloem-Mobile RNAs as Systemic Signaling Agents, Annual Rev Plant Biol 68:173-195). As much as 50% of the companion cell transcriptome is believed to be engaged in movement (Kim, G. et al. (2014), Genomic-scale exchange of mRNA between a parasitic plant and its hosts, Science 345:808-811; Thieme, C. J. et al. (2015), Endogenous Arabidopsis messenger RNAs transported to distant tissues, Nature Plants 1(4): 15025; Yang, Y. et al. (2015), Messenger RNA exchange between scions and rootstocks in grafted grapevines, BMC Plant Biol 15, 251), which raises various questions with regard to how and why such a substantial subset of mRNAs are moving long-distances. For example, how selective is the process of RNA movement? If there is selection, how is it facilitated? Are transiting RNAs modified (e.g., methylated)? Are transiting RNAs found in any particular subcellular location before exiting into the SE? Are there "zip codes" for transiting RNAs? Are transiting RNAs bound by specific proteins and are there specific interacting sequences? How much of the flow of mRNAs is biologically meaningful and how much is non-selective, since sink cells are presumably capable of transcribing the same mRNAs?

Confusion in the mRNA movement literature is pervasive. Some studies have indicated that the major determinant of RNA mobility is their abundance in companion cells (Kim, G. et al. (2014), Genomic-scale exchange of mRNA between a parasitic plant and its hosts, Science 345:808-811; Thieme, C. J. et al. (2015), Endogenous Arabidopsis messenger RNAs transported to distant tissues, Nature Plants 1(4):15025; Yang, Y. et al. (2015), *Messenger RNA exchange between scions and rootstocks in grafted grapevines*, BMC Plant Biol 15, 251). Mathematical modeling has been used to propose a non-selective, Brownian diffusion model for mRNA movement based mainly on their abundance, with half-life and transcript length also playing roles (Calderwood, A. et al. (2016), *Transcript Abundance Explains mRNA Mobility Data in Arabidopsis thaliana*, Plant Cell 28:610-615). However, other studies reached opposing conclusions, finding that mRNA abundance in companion cells does not correlate with movement (Xia, C. et al. (2018), *Elucidation of the Mechanisms of Long-Distance mRNA Movement in a Nicotiana benthamiana Tomato Heterograft System*, Plant Physiol 177:745-758). In addition, while it is generally assumed that the phloem does not contain RNases that target the transiting RNAs (Morris, R. J. (2018), *On the selectivity, specificity and signaling potential of the long-distance movement of messenger RNA*, Curr Opin Plant Biol 43:1-7), Xia et al. also found that most mobile mRNAs are degraded and never reach the root or upper stem. Other studies found that the presence of a predicted tRNA-like structure is associated with over 11% of mobile mRNAs (Zhang, W. N. et al. (2016), *tRNA-Related Sequences Trigger Systemic mRNA Transport in Plants*, Plant Cell 28: 1237-1249), suggesting that mobile mRNAs might harbor specific "zip-codes". However, other abundant mRNAs containing similar tRNA-like motifs were not mobile (Xia, C. et al. (2018), *Elucidation of the Mechanisms of Long-Distance mRNA Movement in a Nicotiana benthamiana/Tomato Heterograft System*, Plant Physiol 177:745-758). Thus, prior studies have failed to identify and develop a model system consisting of a highly abundant, mobile RNA whose movement is traceable in living tissue under different cellular conditions.

Plant viruses, many of which move through the plant as a ribonucleoprotein complex (vRNP), have evolved to use the same pathway as used by mobile endogenous RNAs. Plant viruses can accumulate in substantial amounts, and most initiate infection in epidermal or mesophyll cells and then move cell-to-cell through highly selective intercellular connectors called plasmodesmata, which allow for continuity between the cytoplasm of neighboring cells (FIG. 1: see also Lee, J. Y. and Frank, M. (2018), *Plasmodesmata in phloem: different gateways for different cargoes, Curr Opin Plant Biol* 43:119-124: Schoelz, J. E. et al. (2011), *Intracellular transport of plant viruses: finding the door out of the cell*, Mol Plant 4:813-831). Long-distance systemic movement (leaf-to-leaf) requires that the virus enters companion cells, where replication takes place, followed by progeny exit into sieve elements by transiting through the specialized, branched plasmodesmata that connect companion cells and sieve elements. Once tubular sieve elements are reached, viruses move passively with the phloem photoassimilate stream and establish systemic infections upon exiting (Folimonova, S. Y. and Tilsner, J. (2018), *Hitchhikers, highway tolls and roadworks: the interactions of plant viruses with the phloem*, Curr Opin Plant Biol 43:82-88).

For viruses that transit through the phloem as vRNPs, movement is similar to that of host mRNAs. All plant viruses encode at least one movement protein necessary for movement, which bind to viral RNA and also dilate plasmodesmata. Thus, host mRNA movement also likely requires similar host-encoded movement proteins. Viral movement proteins are non-specific RNA binding proteins. However, questions remain with regard to how vRNPs load into the phloem and unload in distal tissues, although reprograming companion cell gene expression may be required (Collum, T. D. et al. (2016), *Tobacco mosaic virus-directed reprogramming of auxin/indole acetic acid protein transcriptional responses enhances virus phloem loading*, Proc Natl Acad Sci USA 113:E2740-E2749). If mRNA trafficking is so widespread and non-specific, it has remained unclear why RNA viruses require their own encoded movement proteins. Some researchers have suggested that RNA viruses require movement proteins if they move as preformed replication complexes that include a large RNA-dependent RNA polymerase (Heinlein, M. (2015), *Plant virus replication and movement*, Virology 479:657-671), which is beyond the size-exclusion limit (~70 kDa) of companion cell plasmodesmata. It has also remained unclear why and how some viruses are phloemlimited. For example, phloem-limited closteroviruses have at least 3 movement proteins, and phloem-limitation can be relieved by over-expressing the silencing suppressor and downregulating host defenses (Folimonova, S. Y. and Tilsner, J. (2018), *Hitchhikers, highway tolls and roadworks: the interactions of plant viruses with the phloem*, Curr Opin Plant Biol 43:82-88), suggesting that phloem-limitation is a complex process for some viruses. Phloem-limitation can also be an active process (as opposed to lack of a cell-to-cell movement protein). For example, altering a domain of the Potato leaf role virus movement protein conferred the ability to exit the phloem (Bendix, C., and Lewis, J. D. (2018), *The enemy within: phloem-limited pathogens*, Mol Plant Path 19:238-254).

A direct connection between host movement of mRNAs and vRNP movement was established when the origin of plant virus movement proteins was solved. A pumpkin protein (RPB50) related to the Cucumber mosaic virus movement protein was discovered that was capable of transporting its own mRNA, as well as other mRNAs, into the phloem (Xoconostle-Cazares, B. et al. (1999), *Plant paralog to viral movement protein that potentiates transport of mRNA into the phloem*, Science (New York, NY) 283: 94-98; Ham, B. K. et al. (2009), *A polypyrimidine tract binding protein, pumpkin RBP50, forms the basis of a phloem-mobile ribonucleoprotein complex*, Plant Cell 21:197-215). A complex population of these endogenous movement proteins, known as non-cell-autonomous proteins (NCAPs), have been proposed as being responsible for the long-distance phloem trafficking of mRNAs (Gaupels, F. et al. (2008), *Nitric oxide generation in Vicia faba phloem cells reveals them to be sensitive detectors as well as possible systemic transducers of stress signals*, New Phytol 178:634-646; Gomez, G. et al. (2005), *Identification of translocatable RNA-binding phloem proteins from melon, potential components of the long-distance RNA transport system*, Plant J 41:107-116; Kim, M. et al. (2001), *Developmental changes due to long-distance movement of a homeobox fusion transcript in tomato*. Science (New York, NY) 293:287-289; Pallas, V. and Gomez, G. (2013), *Phloem RNA-binding proteins as potential components of the long-distance RNA transport system*, Front Plant Sci 4:130; Yoo, B. C. et al. (2004), *A systemic small RNA signaling system in plants*, Plant Cell 16:1979-2000).

Since their discovery (Deom, C. M. et al. (1987), *The 30-kilodalton gene product of tobacco mosaic virus potentiates virus movement*, Science (New York, NY) 237:389-394), a number of viral movement proteins have been identified that are responsible for intracellular trafficking of vRNPs to the plasmodesmata, as well as for cell-to-cell and long-distance movement (Tilsner, J. (2014), *Techniques for RNA in vivo imaging in plants*, J Microscopy 258(1): 1-5).

For some viruses (e.g., umbraviruses), cell-to-cell and long-distance movement are associated with multiple movement proteins (Ryabov, E. V. et al. (2001), *Umbravirus-encoded proteins both stabilize heterologous viral RNA* and *mediate its systemic movement in some plant* species, Virology 288:391-400). For example, closteroviruses such as Citrus tristeza virus contain three movement proteins. However, for many viruses, all movement activities are thought to be associated with a single movement protein.

Delivering engineered therapeutic agents into plants for combating diseases, insects or other adverse conditions (e.g., HLB and/or the carrier insects) using virus vectors is an established means of introducing traits such as resistance to pathogens or other desired properties into plants for research purposes. Various methods of providing vectors to plants are known in the art. This is often achieved by delivery of the virus vector into a plant cell's nucleus by Agrobacteria tumefactions-mediated "agroinfiltration," which may result in a modification of that cell's genome, or by delivering the virus vector directly into a cell's cytoplasm, which results in infection without a requirement for genomic modification. In the case of agroinfiltration of RNA viruses, the cDNA of the viral genome is incorporated into the T-DNA, which Agrobacteria delivers into the plants. Such T-DNA includes further regulatory DNA components (e.g., promoter for RNA polymerase), which allow for transcription of the viral genome within plant cells. The incorporated virus, containing therapeutic DNA inserts, is transcribed into RNA within the plant cells, after which the virus behaves like a normal RNA virus (amplification and movement). Thus, to act as an effective vector, a virus should be engineered to accept inserts without disabling its functionality and to ensure that the engineered virus is able to accumulate systemically in the host to a level sufficient to deliver and in some cases express the insert(s). These inserts, whether open reading frames (ORFs) that will be translated into proteins or non-coding RNAs that will be used for a beneficial function, should be delivered into the targeted tissue in a manner that is effective and sufficiently non-toxic to the host or to any downstream consumption of the host or the environment. However, only a limited number of viral vectors exist that meet the above criteria and are available for only certain plants (e.g., Tobacco rattle virus for tobacco). Unfortunately, there is either no known suitable viral vector, or only suboptimal viral vectors, for most plants, particularly for long lived trees and vines.

Thus, the ability to implement RNA or DNA therapies on a broad basis is substantially limited with existing technologies. Over 1,000 plant viruses have been identified with many plants subject to infection by multiple viruses. For example, citrus trees are subject to Citrus leaf blotch virus, Citrus leaf rugose virus, Citrus leprosis virus C, Citrus psorosis virus, Citrus sudden death-associated virus, Citrus tristeza virus (CTV), Citrus variegation virus, Citrus vein enation virus and Citrus yellow mosaic virus, among others. However, CTV, the causal agent of catastrophic citrus diseases such as quick decline and stem pitting, is currently the only virus that has been developed as a vector for delivering agents into citrus phloem.

CTV is a member of the genus Closterovirus. It has a flexuous rod-shaped virion composed of two capsid proteins with dimensions of 2000 nm long and 12 nm in diameter. With a genome of over 19 kb, CTV (and other Closteroviruses) are the largest known RNA viruses that infect plants. It is a virulent pathogen that is responsible for killing or rendering useless millions of citrus trees worldwide, although the engineered vector form is derived from a less virulent strain, at least for Florida citrus trees (still highly virulent in California trees). Prior studies have purportedly demonstrated that CTV-based vectors can express engineered inserts in plant cells (U.S. Pat. No. 8,389,804: US 20100017911 A1). However, it has not been commercialized due to its inconsistent ability to accumulate in plants and achieve its targeted beneficial outcome. It is thought that CTV's inability to replicate to sufficiently high levels and heat sensitivity limits its ability to generate a sufficient quantity of RNA for treatment.

Thus, CTV-based vectors have a very limited ability to deliver an effective beneficial payload where needed. Moreover, CTV is difficult to work with due to its large size. CTV is also subject to superinfection exclusion, wherein a CTV-based vector is unable to infect a tree already infected with CTV. CTV is also highly transmissible from plant to plant via several aphid species, a property disliked by regulators concerned with uncontrolled escape into the environment where it might mutate or interact with other hosts in undesirable ways. In addition, strains suitable for one region (e.g., Florida) are unsuitable for varieties of trees in another region (e.g., California). Despite such problems, CTV is the only viral vector platform available for citrus trees.

Accordingly, there is a need for an infectious agent that solves some or all of the above-noted problems, and which is capable of introducing a desirable property and/or delivering a therapeutic agent(s) into a plant, particularly a long-lived plant such as a tree or vine.

SUMMARY

The present disclosure relates to a novel infectious agent(s) capable of delivering an exogenous insert(s) into a plant, compositions comprising a plant infected by the disclosed agent(s), and methods and uses relating thereto. The disclosed agents are sometimes referred to herein as "independently mobile RNAs" or "iRNAs." Despite being infectious single-stranded RNAs, iRNAs are not viruses given they do not code for any movement protein(s) or RNA silencing suppressors, which are key characteristics of plant viruses. In addition, unlike virtually all plant RNA viruses, with the exception of umbraviruses, iRNAs also do not encode a coat protein for encapsidating the RNA into virions, which is a requirement for vectored movement of viruses from plant to plant. Despite the lack of movement protein expression, iRNAs are able to move systemically within the phloem in a host plant. As compared to viruses, iRNAs have additional advantageous properties, such as: the ability to accumulate to levels exceeding those of most known plant viruses; relatively small size, e.g., being only about two-thirds the size of the smallest plant RNA virus and thus much easier to work with compared to such conventional plant RNA viruses; and the inability to spread on their own to other plants (given their inability to encode for any coat protein).

In accordance with disclosed embodiments, an infectious agent comprises an RNA-based vector, e.g. an iRNA, which may contain one or more engineered insert(s), sometimes referred to herein as a heterologous segment(s), which, for example, triggers in a plant expression of a targeted peptide, protein(s) and/or produces targeted small interfering or other non-coding RNA that are cleaved from the vector for beneficial application, and/or delivers a therapeutic agent into the plant, and/or otherwise effectuates or promotes via such targeting or delivery a beneficial or desired result. Aspects of the present disclosure include: an iRNA-based vector for delivery of targeted anti-pathogenic agents; an anti-bacterial enzy biotic targeted at bacteria infecting a plant or bacteria required by the insect vector; an enzy biotic that is generated from the TEV IRES; incorporation of siRNAs into the iRNA genome; incorporation of inserts into a lock and dock structure to stabilize the base of a scaffold that supports the inserts; incorporation of siRNAs into an iRNA genome that has been modified to enhance the stability of the local region to counter the destabilizing effects of the inserts; incorporation of an siRNA that disrupts or kills a targeted insect vector; incorporation of an siRNA that mitigates the negative impacts of a tree's callose production; incorporation of an siRNA that mitigates the plant's recognition of the pathogen; incorporation of an siRNA or other agent that targets bacterial, viral or fungal pathogens; and incorporation of an insert that triggers a particular plant trait (e.g., dwarfism). Thus, the infectious agents and compositions disclosed herein possess superior and advantageous properties as compared to conventional technologies.

The iRNA-based vectors of the present disclosure are suitable for use as a general platform for expression of various proteins and/or delivery of small RNAs into the phloem of citrus and other host plants. In some implementations, a Citrus yellow vein associated virus (CYVaV)-based vector is provided, which accumulates to massive levels in companion cells and phloem parenchyma cells. The vectors of the present disclosure may be utilized to examine the effects of silencing specific gene expression, e.g., in the phloem (and beyond) of trees. In addition. CYVaV may be developed into a model system for examining long-distance movement of mRNAs through sieve elements. Since CYVaV is capable of infecting virtually all varieties of citrus, with few if any symptoms generated in the infected plants, movement of RNAs within woody plants may be readily examined.

In accordance with disclosed embodiments, the present disclosure is directed to a plus-sense single stranded ribonucleic acid (RNA) vector comprising a replication element(s) and a heterologous segment(s), wherein the RNA vector lacks a functional coat protein(s) open reading frames (ORFs) and a functional movement protein ORFs. The RNA vector is capable of movement in a host plant, for example systemic movement, movement through the phloem, long-distance movement and/or movement from one leaf to another leaf. In some implementations, the RNA vector also lacks any silencing suppressor ORF(s). In some implementations, the RNA vector comprises a 3' Cap Independent Translation Enhancer (3' CITE) comprising the nucleic acid sequence(s) of SEQ ID NO: 4 and/or SEQ ID NO: 5. In some embodiments, the 3' CITE comprises the nucleic acid sequence of SEQ ID NO: 3.

In some embodiments, the replication element(s) of the RNA vector comprises one or more conserved polynucleotide sequence(s) having the nucleic acid sequence of: SEQ ID NO: 10, SEQ ID NO: 11, SEQ ID NO: 12, SEQ ID NO: 13, and/or SEQ ID NO: 14. In some implementations, the replication element(s) additionally or alternatively comprises one of more conserved polynucleotide sequence(s) having the nucleic acid sequence of: SEQ ID NO: 15 and/or SEQ ID NO: 16.

In some embodiments, the RNA vector is derived from citrus yellow vein associated virus (SEQ ID NO:1) or an iRNA relative thereof. The RNA vectors of the present disclosure are capable of systemic and phloem-limited movement and replication within a host plant. The RNA vectors of the present disclosure are functionally stable for replication, movement and/or translation within the host plant for at least one month after infection thereof.

In some embodiments, the heterologous segment(s) of the RNA vector of the present disclosure comprises a polynucleotide that encodes at least one polypeptide selected from the group consisting of a reporter molecule, a peptide, and a protein or is an interfering RNA. In some implementations, the polypeptide is an insecticide or an insect control agent, an antibacterial, an antiviral, or an antifungal. In some implementations, the antibacterial is an enzybiotic. In some implementations, the antibacterial targets a bacterium *Candidatus liberibacter* species, e.g. *Candidatus liberibacter asiaticus* (CLas).

In some embodiments, the heterologous segment(s) of the RNA vector of the present disclosure comprises a small non-coding RNA molecule and/or an RNA interfering molecule. In some implementations, the small non-coding RNA molecule and/or the RNA interfering molecule targets an insect, a bacterium, a virus, or a fungus. In some implementations, the small non-coding RNA molecule and/or the RNA interfering molecule targets a nucleic acid of the insect, the bacterium, the virus, or said fungus. In some implementations, the small non-coding RNA molecule and/or the RNA interfering molecule targets a virus, for example a virus selected from the group consisting of Citrus vein enation virus (CVEV) and Citrus tristeza virus (CTV). In some implementations, a targeted bacteria is *Candidus liberibacter asiaticus* (CLas). In some implementations, the iRNA comprises an siRNA hairpin that targets and renders the targeted bacteria non-pathogenic.

It should be understood that the RNA vector may include multiple heterologous segments, each providing for the same or different functionality. In some embodiments, the heterologous segment(s) is a first heterologous segment, wherein the RNA vector further comprising a second heterologous segment(s), wherein the replication element(s) is intermediate the first and second heterologous segments.

In some embodiments, the heterologous segment(s) of the RNA vector of the present disclosure comprises a polynucleotide that encodes for a protein or peptide that alters a phenotypic trait. In some implementations, the phenotypic trait is selected from the group consisting of pesticide tolerance, herbicide tolerance, insect resistance, reduced callose production, increased growth rate, and dwarfism.

The present disclosure is also directed to a host plant comprising the RNA vector of the present disclosure. The host plant may be a whole plant, a plant organ, a plant tissue, or a plant cell. In some implementations, the host plant is in a genus selected from the group consisting of *Citrus, Vitis, Ficus* and *Olea*. In some implementations, the host plant is a citrus tree or a citrus tree graft.

The present disclosure also relates to a composition comprising a plant, a plant organ, a plant tissue, or a plant cell infected with the RNA vector of the present disclosure. In some implementations, the plant is in a genus selected from the group consisting of *Citrus, Vitis, Ficus* and *Olea*. In some implementations, the plant is a citrus tree or a citrus tree graft.

The present disclosure also relates to a method for introducing a heterologous segment(s) into a host plant comprising introducing into the host plant the RNA vector of the present disclosure. In some embodiments, the step of introducing the heterologous segment(s) into the host plant comprises grafting a plant organ or plant tissue of a plant that comprises the RNA vector of the present disclosure to a plant organ or plant tissue of another plant that does not comprise the RNA vector prior to said introduction. The RNA vectors of the present disclosure are capable of systemically infecting the host plant.

The present disclosure is also directed to a process of producing in a plant, a plant organ, a plant tissue, or a plant cell a heterologous segment(s), comprising introducing into said plant, said plant organ, said plant tissue or said plant cell the RNA vector of the present disclosure. In some embodiments, the plant is in a genus selected from the group consisting of *Citrus, Vitis, Ficus* and *Olea*.

The present disclosure also relates to a kit comprising the RNA vector of the present disclosure.

The present disclosure is also directed to use of the RNA vector(s) of the present disclosure for introducing the heterologous segment(s) into a plant, a plant organ, a plant tissue, or a plant cell. The present disclosure is also directed to use of the host plant(s) of the present disclosure, or use of the composition(s) of the present disclosure, for introducing the RNA vector(s) into a plant organ or plant tissue that does not, prior to said introducing, comprise the RNA vector. In some implementations, the step of introducing the RNA vector comprises grafting a plant organ or plant tissue of a plant that comprises the RNA vector to a plant organ or plant tissue of another plant that does not comprise the RNA vector.

The present disclosure is also directed to a method of making a vector for use with a plant comprising the steps of inserting one or more heterologous segment(s) into an RNA, wherein the RNA is selected from the group consisting of: CYVaV: a relative of CYVaV; other RNA vectors having least 50% or at least 70% RdRp identity with CYVaV; and another iRNA. The present disclosure also relates to a vector produced by the disclosed method(s).

The present disclosure also relates to the use of an RNA molecule as a vector, wherein the RNA is selected from the group consisting of: CYVaV: a relative of CYVaV; other RNA vectors having at least 50% or at least 70% RdRp identity with CYVaV; and, another iRNA. In some implementations, the RNA is used in the treatment of a plant, for example the treatment of a viral or bacterial infection of a plant, for example the treatment of CTV infection or Citrus Greening in a Citrus plant, or in the control of insects that are vectors and/or feed on the plant. The RNA is modified with one or more inserted heterologous segment(s), for example an enzy biotic or an siRNA.

The present disclosure is also directed to the use of an RNA molecule characterized by being in the manufacture of a medicament to treat a disease or condition of a plant, wherein the RNA is selected from the group consisting of: CYVaV; a relative of CYVaV; other RNA vectors having at least 50% or at least 70% RdRp identity with CYVaV; and, another iRNA. In some implementations, the disease or condition is a viral or bacterial infection of a plant, for example CTV or Citrus Greening in a Citrus plant.

The present disclosure is also directed to an RNA molecule for use as a medicament or in the treatment of a disease or condition of a plant, wherein the RNA is selected from the group consisting of: CYVaV; a relative of CYVaV; other RNA vectors having at least 50% or at least 70% RdRp identity with CYVaV; and, another iRNA.

The present disclosure is also related to a ribonucleic acid (RNA) vector, for example a plus-sense single stranded ribonucleic acid (RNA) vector, comprising one or more heterologous segment(s), wherein said heterologous element(s) is attached to the main structure of the RNA vector through a lock and dock structure, optionally a branched structure comprising an insert site for the heterologous element and a relatively stable and/or locking structure that does not participate in folding of the heterologous element or the main structure of the RNA vector. In some implementations, the RNA vector is an iRNA-based vector or a virus-based vector. In some implementations, a lock portion of the lock and dock structure comprises a scaffold normally used for crystallography. In some implementations, the lock and dock structure comprises a branched element, wherein a stem and a branch of the branched element are located within a relatively stable structure forming the lock, such as a tetraloop-tetraloop dock, e.g., a GNRA tetraloop docked into its docking sequence, and another branch of the branched element comprises an insert site for the heterologous element. In some implementations, the heterologous element is a hairpin or an unstructured sequence.

The present disclosure is also related to an iRNA-based vector having one or more heterologous segment(s) having an siRNA effective against a plant pathogenic bacteria. In some implementations, the siRNA targets a *Candidatus liberibacter* species such as *Candidatus liberibacter asiaticus* (CLas).

The present disclosure is also related to an iRNA-based vector having a heterologous element comprising a hairpin having a sequence on one side complementary to a sequence within Citrus tristeza virus (CTV) or an unstructured sequence complementary to the plus or minus strand of CTV. In some implementations, the sequence within CTV is conserved in multiple CTV strains. In some implementations, the sequence one on side of the hairpin is complementary with a sequence in multiple CTV strains, or all known CTV strains, despite differences in CTV sequences. The present disclosure is also related to a plant having a sour orange rootstock and an iRNA-based vector having a heterologous element that targets Citrus tristeza virus.

The present disclosure is also related to a method for introducing a heterologous segment(s) into a host plant comprising introducing into said host plant an iRNA-based vector after a) encapsidating the iRNA vector in a capsid protein other than the capsid protein of CVEV, or b) by agroinfiltration after inoculating an agroinfiltration site with *Xanthomonas citri* subsp. *citri* (Xcc), or c) by coating the iRNA with phloem protein 2 (PP2) from sap extracted from cucumber, citrus or other plant.

The present disclosure is also related to an iRNA-based vector comprising one or more inserts at one or more of positions 2250, 2301, 2319, 2330, 2331, 2336, 2375 and 2083 of a CYVaV based RNA. In some implementations, the iRNA-based vector is stabilized, for example by converting G: U pairs to G:C pairs in the 3'UTR structure.

The present disclosure is also related to a method of making a ribonucleic acid (RNA) vector comprising stabilizing the 3' UTR structure of a parental construct and inserting one or more destabilizing heterologous segment(s) into the stabilized parental construct.

The present disclosure describes many CYVaV-based vectors, but in some implementations analogous vectors are produced using another iRNA or a virus as the starting material or sequence. In these implementations, descriptions relating to CYVaV may be modified accordingly. For example, positions described for CYVaV may be substituted with a corresponding position in another type of iRNA or RNA or virus.

In some implementations, an iRNA-based vector or a virus-based vector is constructed using starting material (i.e., an iRNA or virus) obtained from the wild, or multiplied cloned or otherwise reproduced from starting material obtained from the wild. The starting material is modified, for example to change, delete and/or replace, one or more elements of the wild-type structure and/or to add one or more inserts. In other implementations an iRNA-based vector or virus based vector is synthetic. For example, an iRNA-based vector or virus based vector may be made by creating a synthetic replica of the wild type RNA and then modifying the synthetic replica, or directly creating a synthetic replica of a modified RNA.

The present disclosure is also related to a method of making a ribonucleic acid (RNA) vector comprising truncating a hairpin in a parental construct and inserting one or more heterologous segment(s) into the truncated parental construct.

The present disclosure is also related to compositions and methods comprised of combinations or sub-combinations of one or more other compositions or methods described herein, to compositions produced by methods described herein, to methods of making compositions described herein, and to methods of treating plants using compositions described herein.

BRIEF DESCRIPTION OF THE DRAWINGS

FIG. 4 illustrates schematically the genome organization of additional iRNAs and close relatives of CYVaV identified in Opuntia, Fig trees, and Ethiopian corn. The iRNA relatives all have inserts in the 3'UTR and other nucleotide changes that result in the generation of an ORF that encodes for a protein (p21.2) of unknown function.

FIG. 7 shows yellowing symptoms of CYVaV (Panel A) and CYVaV+CVEV (Panel B), which are limited to citron (pictured), lemon, and lime.

FIG. 13 demonstrates that CYVaV does not encode a silencing suppressor. Referring to Panels A and B, *N. benthamiana* 16C plants were agroinfiltrated with a construct expressing GFP (which is silenced in these plants) and either constructs expressing CYVaV p21 or p81, or constructs expressing known silencing suppressors p19 (from TBSV) or p38 (from TCV). Only p19 and p38 suppress the silencing of GFP, allowing the green fluorescence to be expressed (infiltrated regions identified by circled dashed line in Panel B). Referring to Panel C, northern blot probed with GFP oligonucleotide showed that GFP RNA is still silenced in the presence of p21 or p81.

FIG. 28 illustrates the infection of cucumber (Panel A) and cucumber (Panel B) plants with CYVaV. Panel A, left most image, shows an uninfected cucumber cotyledon (mock) and a cucumber cotyledon agroinfiltrated with CYVaV: the image was taken about 2 months after infection, with both plants grown under similar conditions. Panel A, upper and lower images on the right, shows enlarged views of the boxed areas in the left image. Panel B shows an uninfected tomato plant (mock) and a tomato plant infected with CYVaV: the image was taken about 50 days after infection, with both plants grown under similar conditions.

FIG. 29 illustrates structure and sequences of lock and dock structures 1 and 2 (L&D1 and L&D2, respectively) in accordance with the present disclosure (Panel A). A gel image of RT-PCR result is shown in Panel B: First/left lane: RT-PCR from systemically infected plant containing CYVaV and Lock and Dock1: Second/right lane: PCR using the plasmid construct as a template. Sequencing the band showed high stability of the L&D1 and L&D2 scaffold structures. Sequencing confirmed no evidence of any change in the RNA after one month in plants.

FIG. 32 illustrates *N. benthamiana* 16C plant infected with CYVaV with GFP 30 nt hairpin insert at position 2301, and *N. benthamiana* 16C plant infected with CYVaV with L&D1+GFP 30 nt hairpin insert at position 2301. *N. benthamiana* 16C plant infected by only CY2301GFP30s (without lock and dock structure) is shown in Panel A. Virus-induced gene silencing (VIGS) effect was not detected. Sequencing alignment between input CYVaV (CY2301GFP30) and the CYVaV accumulating in systemic tissue is shown in Panel B. The later CYVaV contains a 19 nt deletion acquired during infection showing the construct was not stable. N. Benthamiana 16C plant infected with CY2301 LDIGPF30s where the 30 nt sequence was inserted into L&D1 at position 2301 is shown in Panel C. Obvious GFP silencing (plant fluorescing red; shown as darker gray in Panel C) by the VIGS vector was observed. Sequence alignment between CY2301LD1GFP30s infected plant and the original construct (Panel D) showed that L&D1 enhanced the stability of the 30 nt insertion. The 30 nt hairpin GFP sequence (plus-sense orientation) is shown in Panel E.

FIG. 33 illustrates the stability of lock and dock 1 (L&D1) (CYm2250LD1) and of L&D1+a 30 nt unstructured sequence targeting Callose Synthase (CYm2250LD1Cal_30 as) and inserted into CYVaV with a truncated hairpin at a position designated as position 2250 before the truncation. N. benthamiana plant infected by CYm2250LD1 is shown in FIG. 33, Panel A, which contains L&D1 at the end of a truncated hairpin. The addition of this insert at the end of the complete hairpin present in the wild-type molecule was not found to be stable. Sequencing alignment (FIG. 33, Panel B) between CYm2250LD1 in infected tissue (RT-PCR) and the original construct shows complete stability. N. Benthamiana 16C plant infected by CYm2250LD1asCal7_30 as (CYVaV containing L&D1 with the 30 nt siRNA insert targeting Callose Synthase 7 mRNA expression) is shown in FIG. 33, Panel C. Sequence alignment (FIG. 33, Panel D) between CYm2250LD1Cal730as accumulating in the infected plant (RT-PCR) and the original construct showing that the 30 nt insert was stable within L&D1. The 30 nt Callose synthase 7 siRNA sequence (antisense orientation) that targets the Callose Synthase that is active in phloem is shown in FIG. 33, Panel E.

FIG. 34 illustrates the secondary structure of a construct including two insertions (CY2301LD2/2330CTV6sh). One insert is a hairpin targeting CTV6 and the other is an empty L&D2 in 2301 (Panel A). N. benthamiana infected with CY2301LD2/2330CTV6sh is shown in Panel B. RT-PCR result from CY 2301LD2/2330CTV6sh-infected plant is shown in Panel C. The top band had both inserts and was the same as the original infiltrated construct. The lower band has a deletion in L&D2. The data showed that the two inserts were tolerated.

FIG. 35 illustrates another lock and dock structure with enhanced stability and plant infected therewith. Extending base-pairing at the base of the disclosed lock and dock structures improved stability of larger unstructured inserts. Base-pairing was extended in L&D1 (Panel C) thereby resulting in a third lock and dock structure (L&D3). N. benthamiana plant infected with L&D3 at position 2301 (CY2301LD3) is shown in Panel A. RT-PCR from the symptomatic leaf of infected plant showing a single band (no obvious deletions) is shown in Panel B. Sequence alignment of CYVaV with L&D1 in position 2301 with RT-PCR sequencing of CY2301LD3 from infected plant is shown in Panel C. No instability was detected.

FIG. 36 illustrates a stable hairpin insert in CYVaV at position 2375. N. benthamiana plant infected by CY2375LD1 (CYVaV with the L&D1 inserted at position 2375) is shown in Panel A. RT-PCR from the symptomatic leaf of the infected plant is shown in Panel B. The sequencing result of the larger band was identical to the original sequence. However, the sequence of the short band revealed the partial deletion of L&D1. The secondary structure of the new insertion site is shown in Panel C.

DETAILED DESCRIPTION OF EMBODIMENTS

Figure 1:
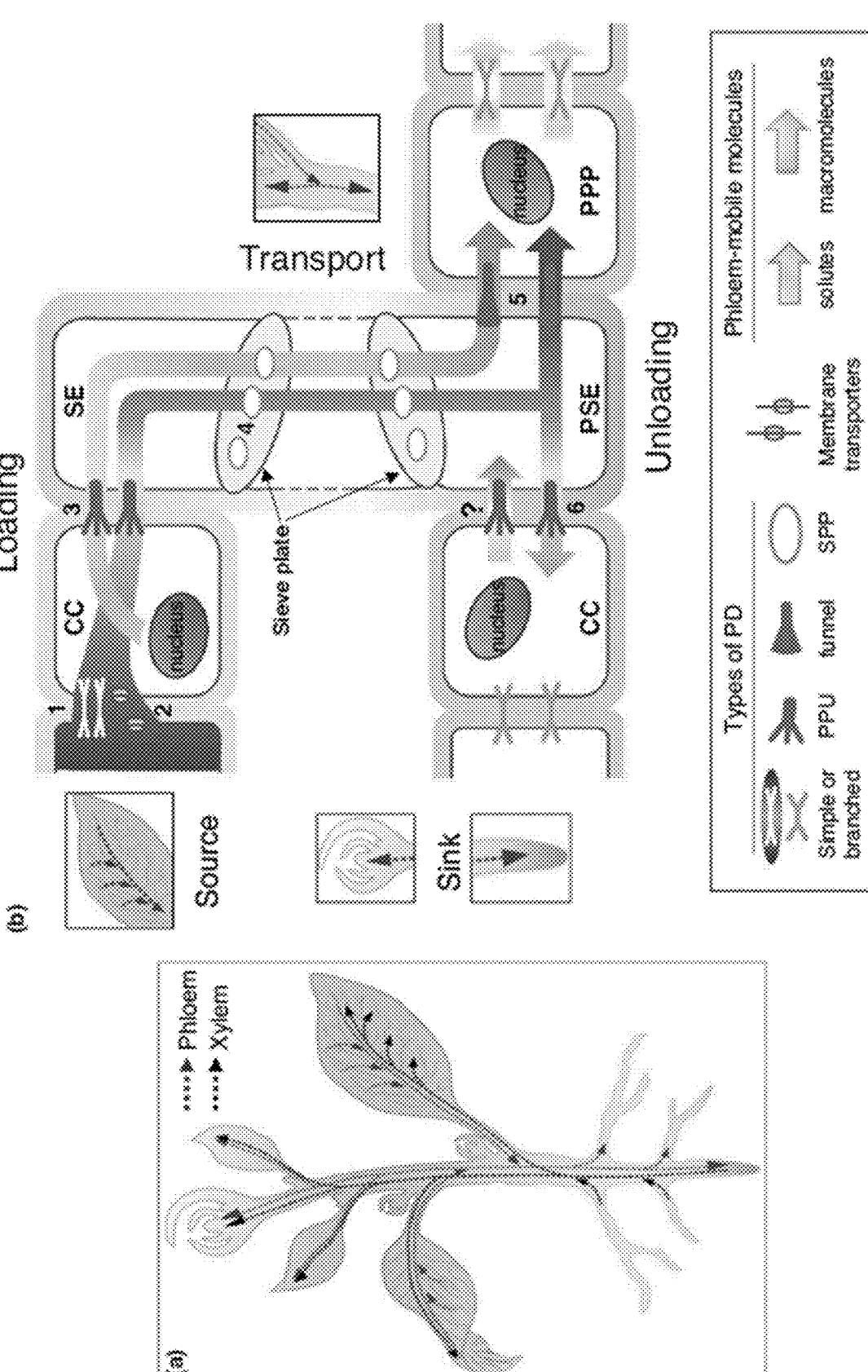
FIG. 1 illustrates schematically the movement pathways through the vascular system of plants (Lee, J. Y. and Frank, M. (2018), *Plasmodesmata in phloem: different gateways for different cargoes*, Curr Opin Plant Biol 43:119-124).

The present disclosure relates to novel infectious agents for use as vectors for plants, compositions comprising a plant infected by the disclosed agent(s), and uses and methods relating thereto. The infectious agents of the present disclosure are sometimes referred to herein as "independently mobile RNAs" or "iRNAs" and exhibit superior characteristics as compared to conventional viral vectors. In accordance with disclosed embodiments, the iRNAs are RNA molecules capable of infecting plants and encoding for an RNA polymerase to sustain their own replication, but lacking the ability to encode for any movement protein or coat protein. In addition, iRNAs do not code for any RNA silencing suppressors.

As used herein, a "host" refers to a cell, tissue or organism capable of being infected by and capable of replicating a nucleic acid. A host may include a whole plant, a plant organ, plant tissue, a plant protoplast, and a plant cell. A plant organ refers to a distinct and visibly differentiated part of a plant, such as root, stem, leaf, seed, graft or scion. Plant tissue refers to any tissue of a plant in whole or in part. Protoplast refers to an isolated cell without cell walls, having the potency for regeneration into cell culture, tissue or whole plant. Plant cell refers to the structural and physiological unit of plants, consisting of a protoplast and the cell wall.

As used herein, "nucleic acid sequence," "polynucleotide," "nucleotide" and "oligonucleotide" are used interchangeably and refer to a polymeric form of nucleotides of any length. Polynucleotides may have any three-dimensional structure, and may perform any function. A "gene" refers to a polynucleotide containing at least one open reading frame that is capable of encoding a particular polypeptide sequence. "Expression" refers to the process by which a polynucleotide is transcribed into mRNA and/or the process by which the transcribed mRNA is translated into peptides, polypeptides, or proteins.

A vector "derived from" a particular molecule means that the vector contains genetic elements or sequence portions from such molecule. In some embodiments, the vector comprises a replicase open reading frame (ORF) from such molecule (e.g., iRNA). One or more heterologous segment(s) may be added as an additional sequence to the vectors of the present disclosure. In some implementations, said heterologous segment(s) is added such that high level expression (e.g., of a particular protein or small RNA) is achieved. The resulting vector is capable of replicating in plant cells by forming further RNA vector molecules by RNA-dependent RNA polymerization using the RNA vector as a template. An iRNA vector may be constructed from the RNA molecule from which it is derived (e.g., CYVaV).

As used herein, an "infection" or "capable of infecting" includes the ability of a vector to transfer or introduce its nucleic acid into a host, such that the nucleic acid or portion(s) thereof is replicated and/or proteins or other agents are synthesized or delivered in the host. Infection also includes the ability of a selected nucleic acid sequence to integrate into a genome of a target host.

As used herein, a "phenotypic trait" refers to an observable, measurable or detectable characteristic or property resulting from the expression or suppression of a gene or genes. Phenotype includes observable traits as well as biochemical processes.

As used herein, "endogenous" refers to a polypeptide, nucleic acid or gene that is expressed by a host. "Heterologous" refers to a polypeptide, nucleic acid or gene that is not naturally expressed by a host. A "functional heterologous ORF" refers to an open reading frame (ORF) that is not present in the respective unmodified or native molecule and which can be expressed to yield a particular agent such as a peptide, protein or small RNA. For being expressible from the vector in a plant, plant tissue or plant cell, the vector comprising a functional heterologous ORF comprises one or more subgenomic promoters or other sequence(s) required for expression.

Various assays are known in the art for determining expression of a particular product, including but not limited to: hybridization assays (e.g. Northern blot analysis), amplification procedures (e.g. RT-PCR), and array-based technologies. Expression may also be determined using techniques known in the art for examining the protein product, including but not limited to: radioimmunoassay, ELISA (enzyme linked immunoradiometric assays), sandwich immunoassays, immunoradiometric assays, in situ immunoassays, western blot analysis, immunoprecipitation assays, immunofluorescent assays, GC-Mass Spec, and SDS-PAGE.

An "exogenous RNA segment" refers to a segment of RNA inserted into a native molecule, whereby the source of the exogenous RNA segment is different from the native molecule. The source may be another virus, a living organism such as a plant, animal, bacteria, virus or fungus, a chemically synthesized material, or a combination thereof. The exogenous RNA segment may provide any function appropriate for a particular application, including but not limited to: a non-coding function RNA, a coding function in which the RNA acts as a messenger RNA encoding a sequence which, translated by the host cell, results in synthesis of a peptide (e.g., a molecule comprising between about 2 and 50 amino acids) or a protein (e.g. a molecule comprising 50 or more amino acid) having useful or desired properties.

As used herein, "movement protein" refers to a protein(s) required for cell-to-cell and/or long distance movement. "Coat protein" refers to protein(s) comprising or building the virus coat.

Similar to umbraviruses, iRNAs do not possess a functional coat protein(s) ORF and/or otherwise encode for any coat protein. In addition, the RNA polymerase of iRNAs is similar to that of umbraviruses. However, unlike umbraviruses, iRNAs do not possess a functional movement protein(s) ORF and/or otherwise encode for any cell-to-cell movement protein(s) or any long-distance movement protein(s) that serves as a stabilization protein for countering nonsense mediated decay.

Conventional viruses lacking coat proteins are generally less stable inside a plant cell given their genomes are vulnerable to the host RNA silencing defense system. However, iRNAs are surprisingly stable in the intracellular environment, which is an important characteristic for an effective vector. iRNAs are also restricted to the inoculated host plant in the absence of a specific helper virus, since without associated virions they are not transmissible by an insect vector. It is believed that iRNAs are encapsidated into virions only when in the presence of a specific helper virus, e.g., such as an enamovirus, including Citrus vein enation virus (CVEV), which is a rarely seen virus in the United States.

In disclosed embodiments, a recombinant plus-sense single stranded RNA vector is provided that comprises a replication element(s) (e.g., a portion(s) of the vector molecule responsible for replication) and a heterologous segment(s). The RNA vectors of the present disclosure are capable of accumulating to high levels in phloem, and are capable of delivering a therapeutic agent(s) such as a protein, a peptide, an antibacterial and/or an insecticide (e.g., siRNAs) directly into the plant tissue. In certain implementations, the RNA vector is derived from an iRNA molecule, which lacks the ability to encode for any coat protein(s) or movement protein(s). For example, the vector is derived from and/or includes structural elements of the iRNA molecule known as Citrus yellow vein associated virus (CYVaV), an unclassified molecule associated with yellow-vein disease of citrus.

Thus, disclosed embodiments provide for an iRNA-based vector built on or derived from a plus-sense single-stranded RNA molecule using genetic components from an iRNA molecule, e.g., CYVaV. In addition, the present disclosure is directed to kits and/or mixtures comprising an iRNA-based (e.g. a CYVaV-based) vector(s). Such mixtures may be in a solid form, such as a dried or freeze-dried solid, or in a liquid, e.g. as aqueous solution, suspension or dispersion, or as gels. Such mixtures can be used to infect a plant, plant tissue or plant cell. Such kits and mixtures may be used for successfully infecting a plant(s) or plant cell(s) with the iRNA-based vectors of the present disclosure and/or expression of heterologous proteins or delivery of other therapeutic agents to such plant or plant cell(s).

The present disclosure also relates to a plant, plant tissue, or plant cell comprising said iRNA-based vector as disclosed herein, and/or a plant, plant tissue, or plant cell comprising a therapeutic agent or heterologous polypeptide encoded or delivered by said vector. The present disclosure also provides for methods of isolating such heterologous polypeptide from the plant, plant tissue, or plant cell. Methods for isolating proteins from a plant, plant tissue or plant cell are well known to those of ordinary skill in the art.

CYVaV was found in four limequat trees in the 1950s independent of any helper virus (Weathers, L. (1957), *A vein-yellowing disease of citrus caused by a graft-transmissible virus*, Plant Disease Reporter 41:741-742: Weathers, L. G. (1960), *Yellow-vein disease of citrus and studies of interactions between yellow-vein and other viruses of citrus*, Virology 11:753-764; Weathers, L. G. (1963), *Use of synergy in identification of* strain *of Citrus yellow vein virus*, Nature 200:812-813). Further analysis and sequencing of CYVaV was conducted years later by Georgios Vidalakis (University of California, Davis, CA: GenBank: JX101610). Dr. Vidalakis's lab conducted analysis on samples collected from previously established tree sources (Weathers, L. G. (1963), *Use of synergy in identification of* strain *of Citrus yellow vein virus*, Nature 200:812-813) and maintained in the disease bank of the Citrus Clonal Protection Program (CCPP). Studies by the Vidalakis lab to characterize CYVaV were inconclusive. However, many of the infected samples containing CYVaV also contained the enamovirus citrus vein enation virus (CVEV): it was relatively common in the 1950s through 1980s for CCPP personnel to mix infect plants with yellow-vein and vein enation for symptom enhancement.

CYVaV is a small (~2.7 kb) iRNA molecule composed of a single, positive sense strand of RNA. It replicates to extremely high levels, is very stable, is limited to the phloem, and has no known mechanism of natural spread. As such, CYVaV is ideal as a vector platform for introducing an agent(s) into a plant host, e.g., such as a small RNA (e.g., non-coding RNA molecule of about 50 to about 250 nt in length) and/or proteins for disease and/or pest management. The production of proteins that bolster (or silence) defenses, antimicrobial peptides that target bacterium, and/or small RNAs that target plant gene expression or the insect vectors of disease agents provide an effective management strategy. To be efficacious, the proteins and small RNAs should be produced in sufficient quantities and accumulate to sufficient levels in the phloem, particularly small RNAs designed to be taken up by targeted insects or fungal pathogens.

CYVaV is only transmissible in nature with a helper virus but may be moved from tree to tree by grafting, and has been shown to infect nearly all varieties of citrus with the exception of hearty orange, including but not limited to infecting citron, rough lemon, calamondin, sweet orange, sour orange, grapefruit, Rangpur and West Indian lime, lemon, varieties of mandarin, varieties of tangelo, and kumquat. It produces a yellowing of leaf veins in the indicator citron tree and has no or very mild yellow vein symptoms in sweet orange and other citrus with no reported impact on fruit quality, or otherwise causing harm to trees.

The polynucleotide sequence (bases 1 to 2692) of CYVaV is presented below (SEQ ID NO: 1):

```
ggguaaauau ggauccuuca ucuuugcccc gugccuguug gcaucaugcc    50
agacaggugu uucgagcauc aacuagcuuc ucaagagagg ugguucgcgc   100
ugcucguaga uggguuacca ugcccaccag ucgccaugca uaugacuuuu   150
caacgagucu aggcauugug auugcugagc cugcagcucg uuuacgacgc   200
cgucugcccu cguacgaaa gugcgcagag aaguuaguag uccacaagca    250
agucgacacu uuggugggacg aauggugcuc uggaauuccc aacccugaua   300
ucguagaagu ugguugggca cuccgucuga gggaccguuu cggucuuccu    350
cccgcuucug agccuacccg gcucaguggu gagagauggg ugcucaaaca   400
acucaauggg guagauccug agucauggaa ugcugaucuu gguaggucag   450
uucauaucca aggagacuac gccccaggga ggaaugccca uaucgcucag   500
gucgcggcga ccuugugguu aacuaggacc uugcaugaca aggccuuggc   550
ucgccaccag gguuuucgcg auuugcagug auuggggucg acgggcuaga   600
ggcaaaagca gugccucuag cuucuggacu ccgacugcuu ccgguuccgc   650 gaccccggaca aagucgacga cugucucaga ccuuguuacu uccaacaccu    700
cgugcucaau ucgugaauca cgcgugcucg gcuaacaacc uuggacgugu   750
gaugaccaca cguguguugc aguacaaggg ccgagauccg auccuuccccu   800 cuucugaagc ccuucaccga cuuaaccuuc ggauagcuga gcuauauagg   850
ucuagaccuu cuaccgucua uccauuaagu uaugaagggu uucucaauug   900
cuaugaaggc cgacagcgua cucguuacgc ccaagccguc gagcaguuga   950
ugcgguccac ucuugagccg aaagaugcgc gaguugaaac guucauuaag 1000
aacgagaaau uugacugggc guugaaaggg gaggaggcug auccucgagc   1050
aauccaacca aggaagccga aauauuuggc ugagguugga cggugguuca 1100 aaccuugga gcgaaucauc uacaaggauc ucaguaaaag guuguauggu   1150 gaggugcug agccguguau cgccaaaggc cuaaaugcau uagaaucugg   1200
agcgacuuug aggcgcaaau gggagaaguu uucuucucca guuugcguuu   1250
cucucgacgc uuccagguuc gaccugcaug uaagcguugg caugcuaaag   1300
uucacacaca agcuauauga cuauuacugu aagucuccca cucuccagcg   1350
cuaucucaaa uggacacucc gcaaccaugg cgucgccucc ugcaaagaau   1400
ugucauauga guaugagguu guuggccgga gaaugagugg ugacauggac   1450
acugcauugg gcaacugcgu cauuaugucg auacuuacau gguuuaugcu   1500
uagugaacuu ggcauuaagc augaauuauu cgauaauggu gacgauuguu   1550
uguucauuug cgagucucac gacgucccca gccccgaggu aauuacaaac   1600
ugguuuucgg acuuuggguu ugugguuagg uuggaaggcg ucacguccgu   1650
guuugagcgu auugaguuuu gccaaacuuc cccaguaugg acugagaggg   1700
```

-continued

```
guuggcugau guguaggaau auuaagucau ugaguaaaga ccuuacgaau 1750
guuaauucgu gcacgggcuc cacgauugaa uauacccacu gguugaaagc 1800 aguggggaaag ugcgggucaa uacucaaugc ugguguaccu auauuucagu 1850
ccuuucacaa caugcuggaa aggcuuggca cuaacucucg uauugaucga 1900
gggguuuucu ucaaaucagg gcuaguuaau cucauucgug ggauggacag 1950
gcagccugac guugacauca cuacuuccgc ucggcuuucu uucgaagugg 2000
cauucgggau aacacccggg augcaauugg cuauugaacg guacuaugac 2050
ucugucaugg gcucgcugag uaaaauagaa acaacuaagu ggccaauuga 2100
acuaagaaag gaauacgaac acggaaguga gugguacgag gacuuaggcg 2150
uccuaggaug aauaggguca uugguuuacc gaugauaccu guucagaaua 2200
ggauugcucg agcuucguug guuaggguaa cucacauacc uucuuccaua 2250
acuggaaaag gucgugugag caaccuaacc aguuaaugua ggugucuuuc 2300
cguaucuagu cacgauggua agcaacccgu uuaucuguac ggcgcucacc 2350
cguggguagg aaggugaagg uuuuguguucc uuuaggucuu ggacagucug 2400
cgggcuuggg aacgacgccc cgcuagcaac guacugcucu ccuaccggac 2450
ugguagcuua auugucaucu uggagcgaua gcacguggg ccucacccuu 2500 cgcgcguugg acguguugcg ugcccccac agauuuguga aacucuaugg 2550
agcaguuccg cgagccagaa gggaggaugg ccgccuggcg uaauccagga 2600
gcucgggggg gcuuguacuc agaguagcau ucugcuuuag acuguuaacu 2650
uuaugaacca cgcgugucac gugggggagag uuaacagcgc cc         2692
```

Figure 2:
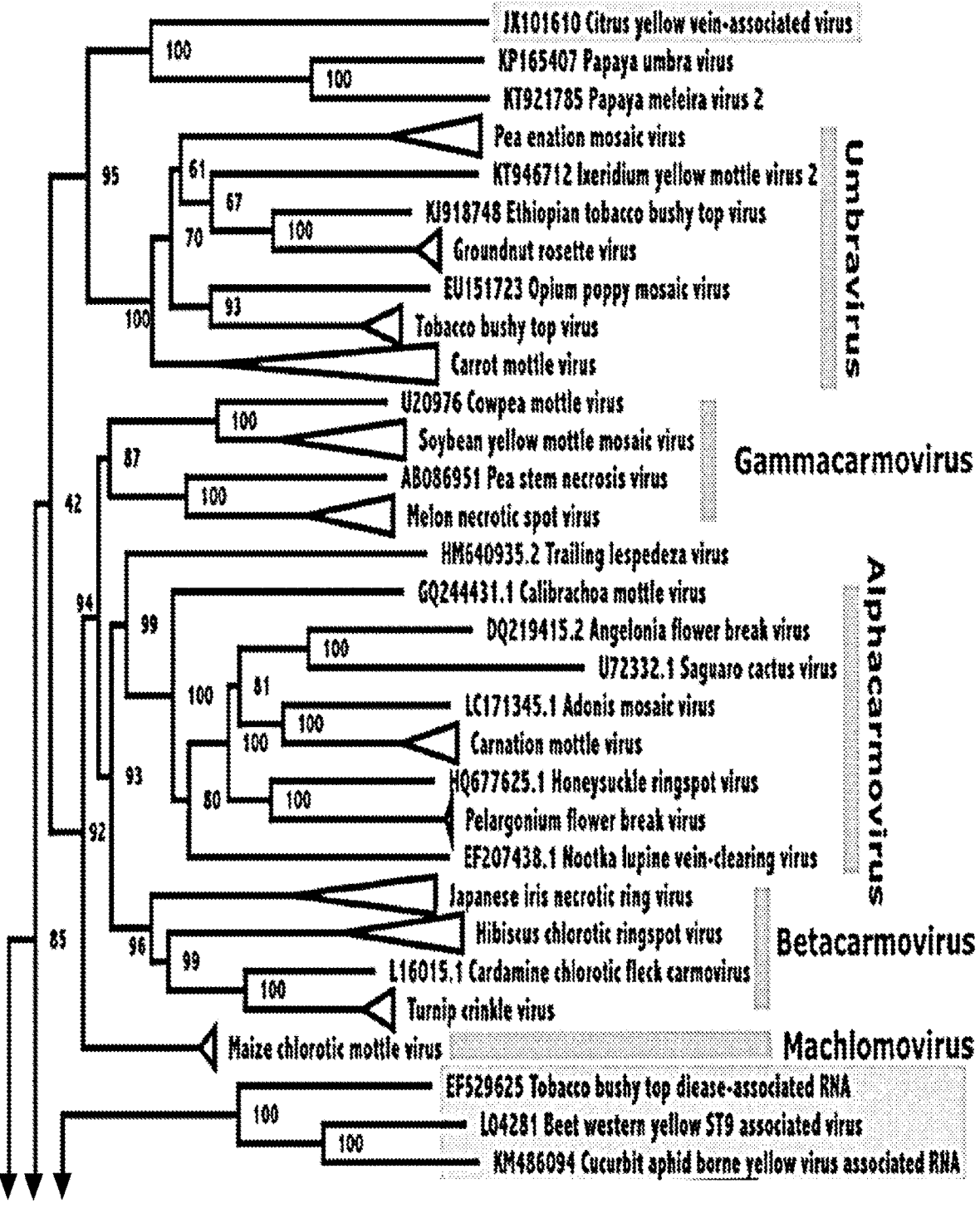
FIG. 2 is a phylogenic tree showing relatedness of the CYVaV with some viruses in the family Tombusviridae.
Figure 2:
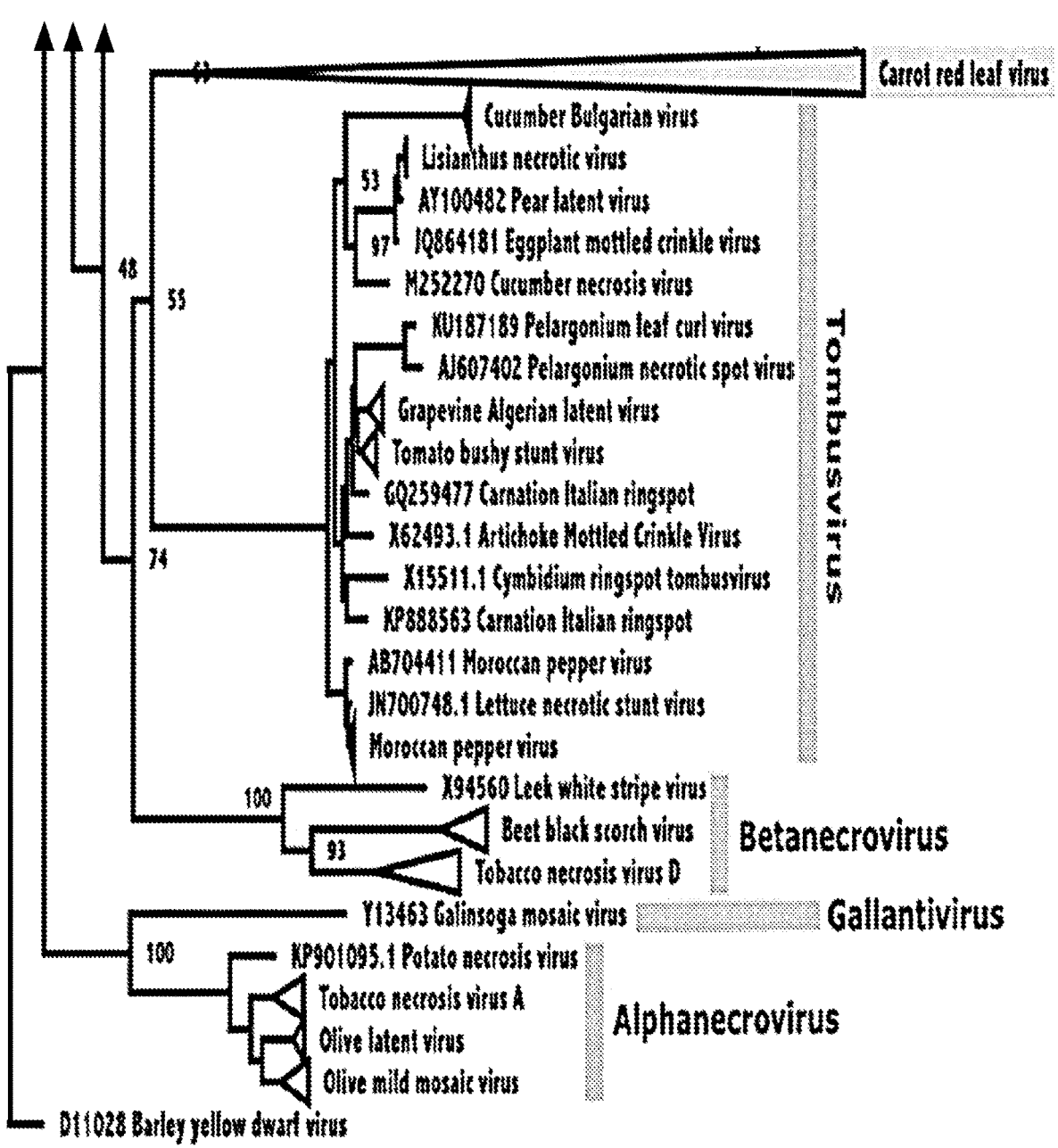
Figure 3:
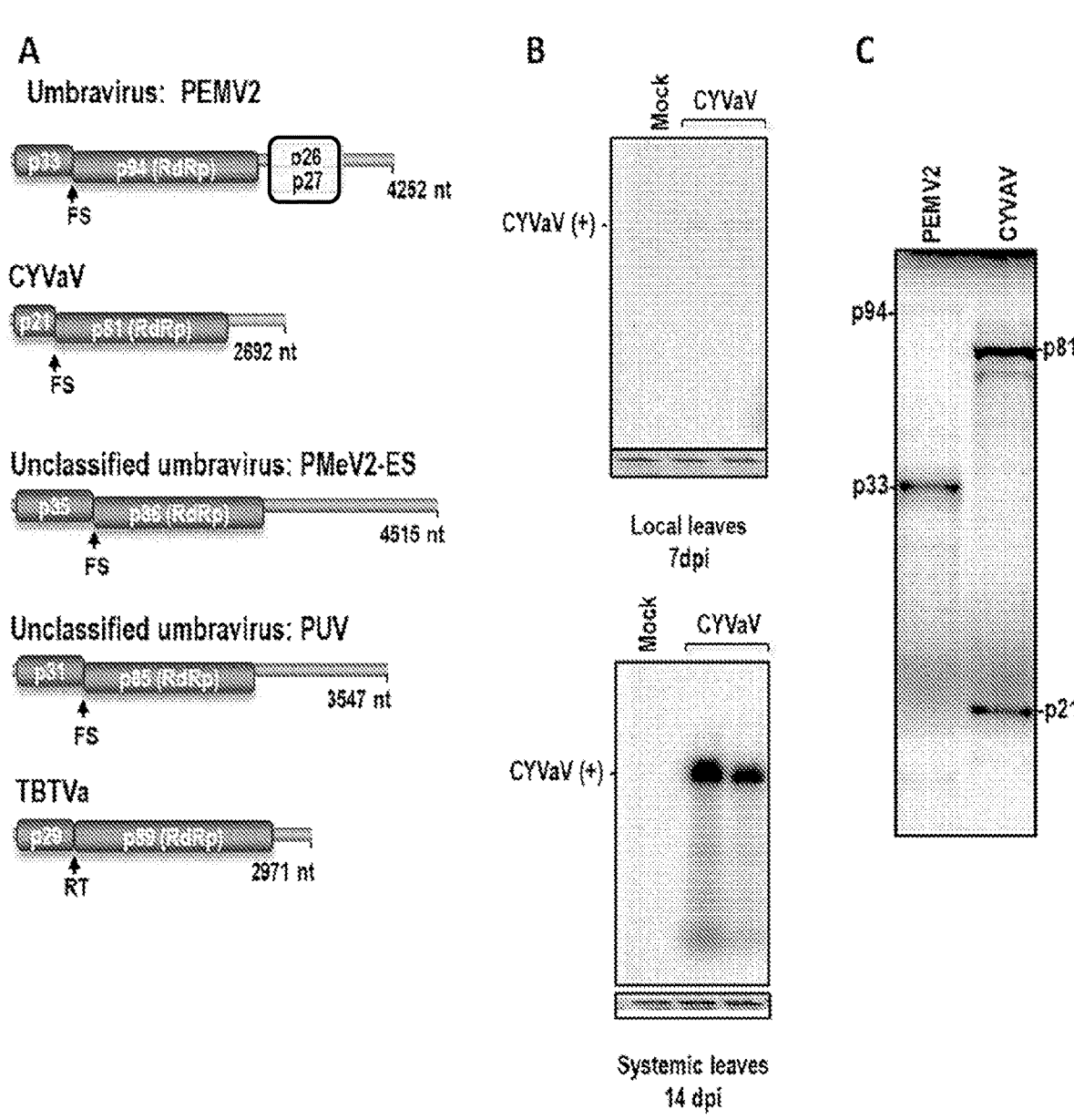
FIG. 3 illustrates schematically the genome organization of CYVaV and similar RNA molecules (Panel A). ORFs encoding for proteins involved in replication are identified in darker grey (p33 and p94 for PEMV2; p21 and p81 for CYVaV; p35 and p86 for PMeV2-ES; p31 and p85 for PUV; p29 and p89 for TBTVa). Umbravirus PEMV2 also possesses ORFs encoding for proteins p26 and p27 involved in movement (identified in light grey boxes). Frameshifting ribosome recording site (FS) and readthrough ribosome recoding site (RT) are also identified. Levels of CYVaV plus (+) strands in infiltrated *N. benthamiana* leaves (Panel B, top) and systemic leaves (Panel B, bottom) are shown. Levels of the RNA-dependent RNA polymerase (RdRp) synthesized by frameshifting in vitro in wheat germ extracts of full-length CYVaV and PEMV2 are shown (Panel C). The difference in levels of p94 from PEMV2 as compared to p81 polymerase produced by CYVaV is significant. The frameshifting site of CYVaV is one of the strongest known in virology and believed to be responsible for its exceptionally high accumulation.

Relatedness of CYVaV with other viruses including Tombusviridae viruses is shown in FIG. 2. Genome organization of CYVaV and similar RNA molecules is illustrated in FIG. 3, Panel A, including PEMV2, PMeV2-ES (GenBank: KT921785), PUV (GenBank: KP165407.1), and TBTVa (GenBank: EF529625.1). The RdRp of CYVaV is most closely related to the umbravirus Pea enation mosaic virus RNA2 (PEMV2). Examination of 5' and 3' sequences of CYVaV revealed considerable similarity to those of umbraviruses, confirming that CYVaV is indeed a complete infectious agent. CYVaV has a plus-sense single stranded RNA genome that only encodes two proteins involved in replication: p21, a replicase-associated protein in related molecules; and p81, the RNA-dependent RNA polymerase (RdRp) that is synthesized by a ribosome recoding (frameshift) event (FIG. 3, Panel A). Levels of the RNA-dependent RNA polymerase (RdRp) synthesized by frameshifting in vitro are shown for PEMV2 and CYVaV. The difference in levels of p94 (RdRp) from PEMV2 as compared to p81 from CYVaV is significant (FIG. 3, Panel C). The frameshifting site of CYVaV is one of the strongest known in virology and believed to be responsible for its exceptionally high accumulation.

The polynucleotide sequence of the 3' end of CYVaV (bases 2468 to 2692) is presented below (SEQ ID NO: 2):

```
ucu uggagcgaua gcacguggg ccucacccuu cgcgcguugg acguguugcg ugcccccac agauuuguga aacucuaugg agcaguuccg cgagccagaa gggaggaugg
```

-continued

```
ccgccuggcg uaauccagga gcucgggggg gcuuguacuc agaguagcau ucugcuuuag acuguuaacu uuaugaacca cgcgugucac gugggggagag uuaacagcgc cc
```

The polynucleotide sequence of the 3' Cap Independent Translation Enhancer (3' CITE) of CYVaV (bases 2468 to 2551) is presented below (SEQ ID NO: 3):

```
ucu uggagcgaua gcacguggg ccucacccuuc cgcgcguugg acguguugcg ugcccccac agauuuguga aacucuaugg a
```

The 3' end (and 3' CITE) of CYVaV comprises the following conserved polynucleotide sequence(s) (bolded and underlined above):

```
                                     (SEQ ID NO: 4)
      auagcacug;

and/or
                                     (SEQ ID NO: 5)
      gauuuguga
```

The polynucleotide sequence of CYVaV that encodes for protein p21 (bases 9 to 578) is presented below (SEQ ID NO: 6):

au ggauccuuca ucuuugcccc gugccuguug gcaucaugcc agacaggugu uucgagcauc aacuagcuuc ucaagagagg ugguucgcgc ugcucguaga uggguuacca ugcccaccag ucgccaugca uaugacuuuu caacgagucu aggcauugug auugcugagc cugcagcucg uuuacgacgc cgucugcccu cguacgaaa gugcgcagag aaguuaguag uccacaagca agucgacacu uuggugggacg aaugggugcuc uggaauuccc aacccugaua ucguagaagu ugguugggca cuccgucuga gggaccguuu cggucuuccu cccgcuucug agccuacccg gcucaguggu gagagauggg ugcucaaaca acucaauggg guagauccug agucauggaa ugcugaucuu gguaggucag uucauaucca aggagacuac gccccaggga ggaaugccca uaucgcucag gucgcggcga ccuugugguu aacuaggacc uugcaugaca aggccuuggc ucgccaccag gguuuucgcg auuugcag The amino acid sequence of protein p21 is presented below (SEQ ID NO:7):

MDPSSLPRACWHHARQVFRASTSFSREVVRAARR

WVTMPTSRHAYDESTSLGIVIAEPAARLRRRLPS

VRKCAEKLVVHKQVDTLVDEWCSGIPNPDIVEVG

WALRLRDRFGLPPASEPTRLSGERWVLKQLNGVD

PESWNADLGRSVHIQGDYAPGRNAHIAQVAATLW

LTRTLHDKALARHOGERDLQ

The polynucleotide sequence of CYVaV that encodes for protein p81 (bases 752 to 2158) is presented below (SEQ ID NO: 8):

augaccaca cguguguugc aguacaaggg ccgagauccg auccuucccu cuucugaagc ccuucaccga cuuaaccuuc ggauagcuga gcuauauagg ucuagaccuu cuaccgucua uccauuaagu uaugaagggu uucucaauug cuaugaaggc cgacagcgua cucguuacgc ccaagccguc gagcaguuga ugcgguccac ucuugagccg aaagaugcgc gaguugaaac guucauuaag aacgagaaau uugacugggc guugaaaggg gaggaggcug auccucgagc aauccaacca aggaagccga aauauuuggc ugagguugga cggugguuca aaccuuugga gcgaaucauc uacaaggauc ucaguaaaag guuguauggu gagggugcug agccguguau cgccaaaggc cuaaaugcau uagaaucugg agcgacuuug aggcgcaaau gggagaaguu uucuucucca guuugcguuu cucucgacgc uuccagguuc gaccugcaug uaagcguugg caugcuaaag uucacacaca agcuauauga cuauuacugu aagucuccca cucuccagcg cuaucucaaa uggacacucc gcaaccaugg cgucgccucc ugcaaagaau ugucauauga guaugagguu guuggccgga gaaugagugg ugacauggac acugcauugg gcaacugcgu cauuaugucg auacuuacau gguuuaugcu uagugaacuu ggcauuaagc augaauuauu cgauaauggu gacgauuguu uguucauuug cgagucucac gacgucccca gccccgaggu aauuacaaac ugguuuucgg acuuuggguu ugugguuagg uuggaaggcg ucacguccgu guuugagcgu auugaguuuu gccaaacuuc cccaguaugg acugagaggg guuggcugau guguaggaau auuaagucau ugaguaaaga ccuuacgaau guuaauucgu gcacgggcuc cacgauugaa uauacccacu gguugaaagc aguggggaaag ugcgggucaa uacucaaugc uggguguaccu auauuucagu ccuuucacaa caugcuggaa aggcuuggca cuaacucucg uauugaucga gggguuuucu ucaaaucagg gcuaguuaau cucauucgug ggauggacag gcagccugac guugacauca cuacuuccgc ucggcuuucu uucgaagugg cauucgggau aacacccggg augcaauugg cuauugaacg guacuaugac ucugucaugg gcucgcugag uaaaauagaa acaacuaagu ggccaauuga acuaagaaag gaauacgaac acggaaguga gugguacgag gacuuaggcg uccuagga The amino acid sequence of protein p81 is presented below (SEQ ID NO:9):

MTTRVLQYKGRDPILPSSEALHRLNLRIAELYRS

RPSTVYPLSYEGFLNCYEGRQRTRYAQAVEQLMR

```
                    -continued
STLEPKDARVETFIKNEKFDWALKGEEADPRAIQ

PRKPKYLAEVGRWFKPLERIIYKDLSKRLYGEGA

EPCIAKGLNALESGATLRRKWEKFSSPVCVSLDA

SRFDLHVSVGMLKFTHKLYDYYCKSPTLQRYLKW

TLRNHGVASCKELSYEYEVVGRRMSGDMDTALGN

CVIMSILTWFMLSELGIKHELFDNGDDCLFICES

HDVPSPEVITNWFSDFGFVVRLEGVTSVFERIEF

CQTSPVWTERGWLMCRNIKSLSKDLTNVNSCTGS

TIEYTHWLKAVGKCGSILNAGVPIFQSFHNMLER

LGTNSRIDRGVFFKSGLVNLIRGMDRQPDVDITT

SARLSFEVAFGITPGMQLAIERYYDSVMGSLSKI

ETTKWPIELRKEYEHGSEWYEDLGVLG
```

The replication element of CYVaV (e.g., that encodes for protein p81) comprises the following conserved polynucleotide sequence(s) (highlighted and underlined above):

```
                                 (SEQ ID NO: 10)
    cguuc;

(SEQ ID NO: 11)
    gaacg;

(SEQ ID NO: 12)
    gguuca;

(SEQ ID NO: 13)
    ggag;
    and/or (SEQ ID NO: 14)
    aaauggga
```

In addition, CYVaV may additionally comprise the following conserved polynucleotide sequence(s) (highlighted and underlined above):

```
                                 (SEQ ID NO: 15)
          ucgacg;
          and/or (SEQ ID NO: 16)
          cuccga
```

Figure 10:
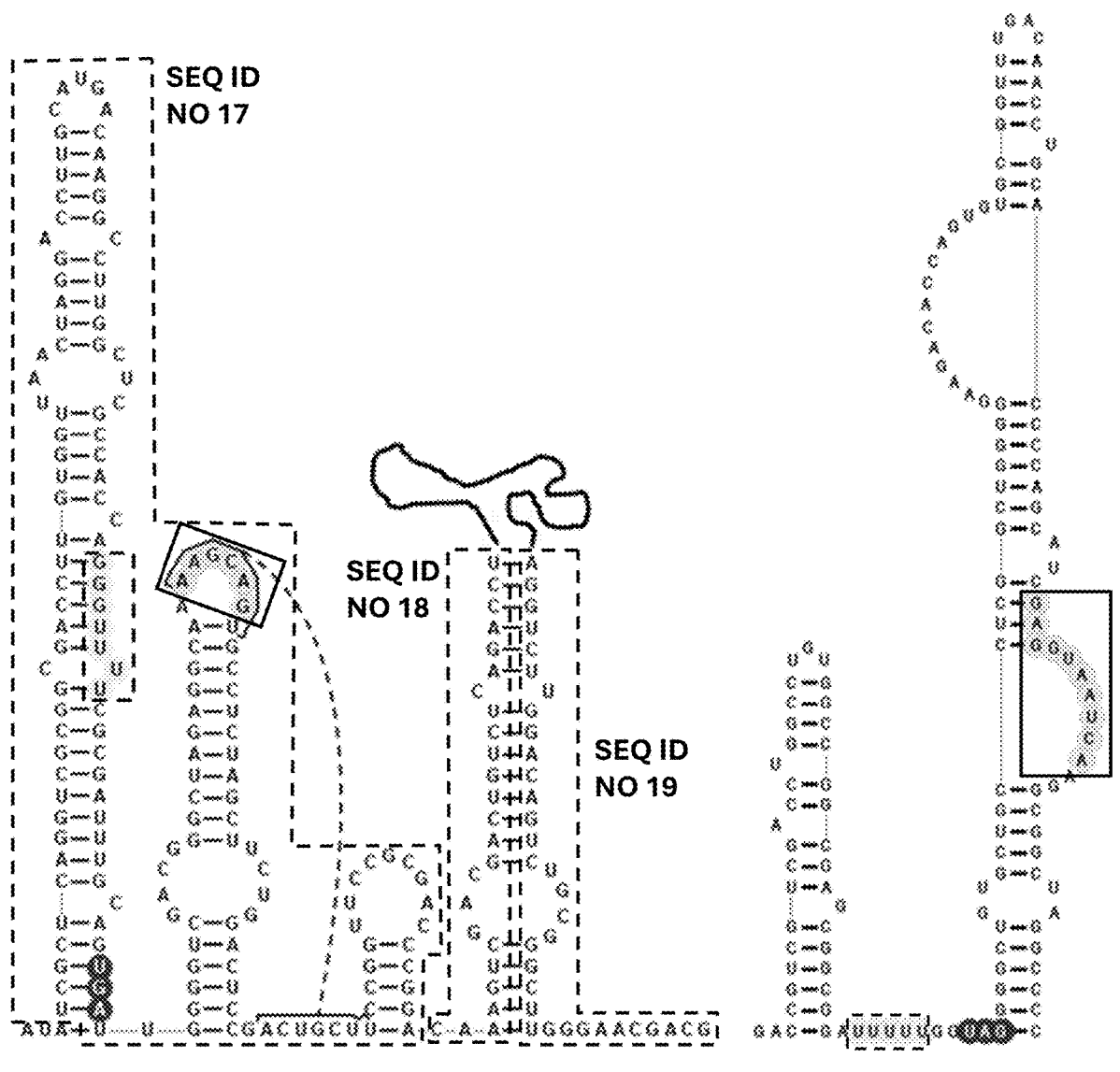
FIG. 10 illustrates schematically the structure of the recoding frameshift sites in CYVaV and PEMV2. CYVaV has multiple conformations of the structures in this region (see FIG. 9) with only one shown. Slippery site is identified by boxed dashed line, and stop codon bases are in black circles. Bases identified by boxed solid line engage in long-distance interaction with the 3' end. Each SEQ ID is shown in the dashed boxes.

The polynucleotide sequences of recoding frameshift sites of CYVaV (see also FIG. 10) is presented below:

```
                                 (SEQ ID NO: 17)
    ucgcucaggucgcggcgaccuugugguuaac uaggaccuugcaugacaaggccuuggcucgc caccagggguuuucgcgauuugcagugauugg ggucgacgggcuagaggcaaaagcagugccu cuagcuucuggacuccgacugcuuccgguuc cgcgacccgga (SEQ ID NO: 18)
    caaagucgacgacugucucagaccu (SEQ ID NO: 19)
    aggucuuggacagucugcgggcuugggaacgacg
```

Highly similar iRNAs have also been found in Opuntia (GenBank: MH579715), fig trees, and Ethiopian corn (FIG. 4), suggesting an unusually large or possibly even unlimited host range for the RNA vectors disclosed herein.

The polynucleotide sequence of a similar iRNA identified in a fig tree (sometimes referred to herein as "iRNA relative 1" or "iRNA r1") is presented below (SEQ ID NO: 20):

```
aaauauggauucgauaucaaugcccgucgccugcugg ucaaaagccaggcaggucuugcguacaccag cuaacuuuuccaaaggggguaguagaaggcugcguaccggugggg ucaacaugcccagagccaaauauguc agagaugucuccacgagucuuggcauaguugucgcugagccuguugcugccgugcgccguuagaugcc uucgauaagcagccuugcggaggaguuggu aacacgccagagcgucgacacucuggugg acgauuggu gucucggacuuuccaacccugacaacaacguggaggu uggu ugggcacuucgucugagggaccgcuuu ggucuuccucccgccucugagcccacaaggcucaguggugag agaugggugcuuaaacaacucaaugg gguagacccggagucguggaauguugaucugcaaagcguuuucgaagacgcucaggaugacuuccauc gggacuacgccccaaggaggaaugcccaaaucgcucaaauugcggcaacccuauggcuuacaaagacc uuagucgauaaggcuuuagcacgccaucaggauuuucgcaguuugcagugauuggggucgacgggcua gaggcuaaagcagugccucucuggcugcuggacuccgacugcuuccgguuccgcggcccggacaaagccg acggcugucucaaaccuugcuacucccuacucccc gugcucaauuugucaaucacgcuaacucaggua auaauuugggg cguguuuugaccacacgggguga ugcaauacaaaggccgagacccgauacuacccucc caggaagcccugcgcaaacuuaaccuucggauaggacaguuguauaagucuagaccauccacugucua uccccugaguuaugaugggguuucuuaauuguuaugaugg ccgacagcguacucgcuacgcucaugccg ucgagcaauugaugggugccgcucugacccccaaaagaugcgcgaguugagacguucauuaagaacgag aaguuugauuggu uguugaaggg gagacgaggcugauccucgugcaaucc aaccuaggaagccgaaaua
```

-continued uuuggccgagguuggucgaugguucaaaccguuggagcgaaucaucuacaaggaucucaguuugcguu uguacggugauaacgcugaaccuugcauugccaaaggcuuaaaugcauuggaaucagggcuacguug agacguaaaugggaaaaguucgcuaauccuguuuguguuucauuggaugcuucucguuucgaccugca cguaagyguuggcuuguuaaaguucacgcauaaauuguacaacuauuacugcaagucucccacucuuc aacgauaucucaaauggacacuccgcaacuccgguaucgccuccguaaggaaaaaucauaugcguau gagguugaaggccguagaaugaguggcgacauggacaccgcauuaggcaacuguaucaucaugagauu auuaacuugguuuaugcuuagcgaacuuggcgugcggcaugagcuuuucgauaaugggugaugacuguu uguuuauuugugaaaaagaagacguuccuagugcugagguaaucacgaacugguuuacggauuuuggg uuuguggguuaagcuagaaggcgucacguccgguguuugagcgcauugaguucugucagaccucaccagu auggacugcgaggggaauggcugauguguagaaacaucaagucauugaguaaagauuuaacgaauguua auucgugcacugguucugccguugaauacacucauugguugaaggcgguggcaagugugggaucuaua cucaaugcugguugucgcccauauuucagucuuuucacaacauguuggucagguugggcacgaauucgcg uauagaucgcggggguauucuuuaggugguggacuuguuaaucucauucgggauggacagacaaccga aaguugagaucacuacuuccgcucgucuuucuuuugaaguggcauucgggaucacucccggcaugcaa uuggcuauugagcaauuuuaugacucagucgugggcccucuggguaaaauaaaaaucuguaaaauggcc aauagaucuaagaaaggaauacgauuacggaagcgcgugguucgaagaccaaggcguccuagggugaa caaggaacucgauuaccgaugacaccuguucaaacuagaaugguucggucaacguugaccaaggaga ccaacauaccuucuacugcaaauagcggucgggggaggcuguuugggcuuguuggccaaucaacuuuagu gucuuuccgcaacuagccucacucgugaauaaaccguuauacuggcgugugccagugugcaaguugc aauggagccggcgaugucuacuuccacccaacauuguggaguuggucucaguucuucuggggccuuca cuaacggugauggguucgguaacgucuuuaagcucuugcguucuuguaacuauacgcggcgcucuccc gugggaggaaacgugauggucaaauggcccaucugcaugcccuucauucuuaacgaugaugcgcacaa gaacacaggauuaaccgccugugugaucauugcagucaccaauacuggugugcuaacguggucaaucuu ggacggagauucuuuugaauguggaguauguagugggugcauagacagucugcgggcuugggaacgac gccccgcuagcaacguacugcucuccuaccggacugguagccguuuaguuaucuuggagcgauagcac ugugagccucacucaacgcgcgauggacguggcgagugcccucagagauuugugaaacucuauagag cuauuucgcgagccagaagggaggauggccaccugguguaagccagguauccccggggggcuuguacu cggggucgcauuacugcuuagaccacaagguaggguucgcaucuuggaacugacccuaugaccuugug ggugcccuaaccggacugguagccguuuaauauacuuggagcgauuagcacgugugagcccucacucaa cggcgcgauuggacguggcgagugccccucagaguaaucugcagagcuccggcagucgugggaggcaa ggca The polynucleotide sequence of an iRNA identified in another fig tree (sometimes referred to herein as "iRNA relative 2" or "IRNA r2") is presented below (SEQ ID NO: 21):

cucccacgacugccggagcucugcagaauuccaccggggguaccuggcuuacaccagguggccauccu cccuucuggcucgcggaauagcucuauagaguuucacaaaucucugaggggcacucgccacguccauc gcgcguugagugaggcucacagugcuaucgcucccagaauucgggauaaauauggaagaaacuucuuu gcccaaagccugcuggaucaaaagccaggcaggucuugcguacaccagcuaacuuuuccaaaggggua gugaaggcugcguaccgguggggucaacaugcccagagccaaauaugucagagaugucuccacgagucu uggcauaguugucgcugagccuguugcugccgugcgccgucagaugccuucgauaagcagccuugcgg -continued aggaguugguaacacgccagagcgucgacacucugguggacgauuggugucucggacuuuccaacccu gacaacaacguggagguugguugggcacuucgucugagggaccgcuuuggucucccucccgccucuga gcccacaaggcucaguggugagagaugggugcuuaaacaacucaauggaguagacccggaaucuugga augacgacuaugcguucgaagacgcucaggaggauuuucaacgggaauacgucccgggaaggaaugcc cauauugcugcaacugcggcaacucuauggcugacaaagaccuuguaugacaaggcuuuaguucgcca ucaggguuuucgcaguuugcagugauuggggucgacgggcuggaggcuaaagcagugccuccagcugc uggacuccgacugcuuccgguuccgcggcccggacaaagccgacggcugucucagaccuuacuacuuc cuacuccccgugcuacuuuugucaaucaugcaaauucaggcaauaaucuugagcguguuuugaccaca cgggugaugcaauacaaaggccgagacccgauacuacccucccaggaagcccugcgcaaacuuaaccu ucggauaggacaguuguauaagucuagaccauccacugucuauccccgaguuaugaugggguuucuua auuguuaugauggccgacagcguacucgcuacgcucaugccgucgagcaauugaugggugccgcucug accccaaaagaugcgcgaguugagacguucauuaagaacgagaaguuugauuggguuguugaagggaga cgaggcugauccucgugcaauccaaccuaggaagccgaaauauuuggccgagguuggucgaugguuca aaccguuggagcgaaucaucuacaaggaucucaguuugcguuuguacggugauaacgcugaaccuugc auugccaaaggcuuaaaugcauuggaaucaggggcuacguugagacguaaaugggaaaaguucgcuaa cgcauaaauuguacgacuauuacugcaagucucccacucuucaacgauaucucaaauggacacuccgc aacuccgguaucgccuccguaaggaaaaaucauaugcguaugagguugaaggccguagaaugagugg cgacauggacaccgcauuaggcaacuguaucaucaugacgauauuaacuugguuuaugcuuagcgaac uuggcgugcggcaugagcuuuucgauaauggugaugauuguuuguucauuugcgaagaaaaagacgua ccuagccccgagacgaucaugaacugguuugcggauuuugggguuugugguuagguuagaaggcgucgu guccguguuugagcgcauugaguucugccaaacaucgccauauggacugaucgagguuggcugaugu guagaaacaucaagucuuugaguaaggaucuuacgaacguuaauucgugcacuggcuccacuguugaa uacacccauugguugaaagcaguuggaaagugugggaucggugcucaaugcgggugugccuauauuuca gucauuucacaacauguugaugcgauugggguacgaauucgcguauagaucgcggggguauucuuuaggu guggacuuguuaaucucauucguggggauggacagacaaccugaaguugagaucacuacuuccgcucgu cuuucuuuugaaguggcauucgggaucacucccggcaugcaauuggcuauugagcaauuuuaugacuc agucgugggcccucugggguaaauaaaaaucuguaaaauggccaauagaucuaagaaaggaauacgauu acggaagcgcgugguucgaagaccaaggcguccuagggugaacaaggaacucggauuaccgaugacac cuguucaaacuagaaugguucggucaacguugaccaaggagaccaacauaccuucuacugcaaauagc ggucgggaggcuguuugggcuuguuggccaaucaacuuuagugucuuuccgcaacuagccucacucgu gaauaaaccguuauacuggcgugugucccagugugcaaguugcaauggagccugcaaugucuucuuucca cccaacauugugg.guguuggucucaguucuucgggggccuucacauaacggugauggguucgguaacgu cuuuaagcucuugcguucuuguaacuauacgcggcgcucucccgugggaggaaacgugaugg ucaaau ggccuaucugcaugcccuucauucuuaacgaugaugcgcacaagaacacaggauuaaccgccugugug aucauugcagucaccaauacuggugugcuaacugguucaaucuuggacggagauucuguugaaugugga guauacgccccgcuagcaucguacugcucuccuaccggacugguagccguuuaguuuaucuuggaguga uagcacuguggggccacauuugacgcgcauuggacgcagacaaugucccuccacagauuugugaaucu cuauggagcuguaaccucggucucucuauagcuuguccgaacaggaaauggacauaaaauaauugcug uuccaacacguuguguugguaaagaaguuauagaugugguguggcgccagacaaguggauggcaaccugga guauccaggcgcucuggggggcuuauacucggagugcauuacugcuuuagaccguuaaucucaagaa -continued ccaugugugucgcauggggaggauuaacggcgcccaauucccuuguuaguuuagguacgccuuggucu ucgaaccacgc

5

The polynucleotide sequence of an iRNA identified in maize (sometimes referred to herein as "iRNA relative 3" or "iRNA r3") is presented below (SEQ ID NO: 22):

gggguaaauauggagaaccagcacacccauguuugcccacggucguuccugcgaaccugcagggcgau ccucgcggcuccagccaacuacggucgugauguggucaaaaucgccuacaaaugggcaucacgaaacc ccgccaccgcccccgaaguguccgagaauccaucggggucguugucggaagcgcuguggacuucuug agcgcuccucgcaagcguuuagaagaccgcgcagagcaguuggugcaagacgaccgggucgaccggau cguccgcgagugggagcuaggaaccgcugacucccgaauuccggaaguugagugggcauaccgucugc gcgaccgcuucggcgucguguccgccagcgagccugcuaggcaaacggugagagguguggugcucaag caacuagagggauuggaggaggggggaguuccgcugcauacccauugagccauuuuuggugaugcacc ggccccgugccauagcccugggagcaacagcgugauugcugcuauugcggcgacccuuuggaugacgc cuacccgccuugaccgggcguugagacgucaccagggguuuucgcaacuagcggugaucggagucgacg gagugucugcuuuagcggugcaggcaucuucugaacuccgaccgcuacggguugggcgaccccgucaa agucgacgucguucguggucucugacuaugccagcacccaaguccuguuucgugaaccacgcuaacuc ugaccacaaucucaaaacggucauggaaaacagggugcucaaguacaaaggccaagaacccgcaaagc cccggguagaagccauaaagcagcucuaugaaaggauacgaccgcgauaucguucucuaccugacacg gucuauccucuaucauaugauggcuuccucaagugcuacuccggacguaggcgaacacgauacgaaca ggccguccaggaguugagaaacgcgccacucacacccgaagaugcugucguuuccacguucaucaaga acgagaaauucgauuggcuccaaaagaaagaacuugcggaucccagagcuauccaaccucggaaaccg aaauaccuggccgaaguugggaggugguucaagccucuggagcacauaauguauaaagacuuggcaaa acgguuguacggucaggaugcguugccuugcauagcgaaagggcugaacgcuagagaaacggcugaag ugcuccgagccaaaugggacaaguucgcuucucccguuugcgucucgcuggaugccagucgguucgau cugcauguaaguccugacgcauugcgguuuacgcaccgccuguaccacaaguauugccaaagucggca acuccgcaaguaccuagaauggacgcugagaaacgcuggcgucgccucauguccugaaagcgcuuauc aguaugagguugaggggagacgcaugaguggcgacauggacaccgcacucggcaacugcguacuuaug cucugcuugacauggaacuuccucgaucaacauaacaucaagcaugagauaauggacaacggagauga cugcuuguucaucugugaagcugccgaugugccaaccgacaagcaaaucauggacuacuaccucgacu uuggguucgugguucguuggaaggaaaggugucuguguucgagcgaauagaguucgucaaaccagu ccgguguugacugcuaauggauggcguaugguuagaaauuugaaguccauugcgaaggaccucugcaa ugugaacauggcgacugggucacucagugaauacacgcguggcuuaaagccgugggaaucguguggua gaauccugaacgaugggguuccaaucuucuccgccuuccacaacaugcuggugcgacauggaacgaac ucacgaauagauagagcgguguucugggaauguggacugacaaacuugaucaaaggcaugaguuucga gcaacuggaaaucacugucgcugcgcgcgaguccuuuuaucuggcauacgguaucacaccggcgagac aacucgcgauugaagaguauuacgacucacuccagggcccgguggguaaaauacaacuucaugaaugg ccacuacaacucaaagaggaauacgcgugcggcgccgagugguucgaaggagacggcgagcgggcuug aggcccgcuggcuugcccuucgugcccggcagcucucgcacgguucggacugcgcucguccucgagaa ccacuugccgauguccucggcacaguugggucaagaggccguugcguauucuaucccgugcaauguuc gaaacaugccuacgauccugacucucgccaccacuccgcucuauuggcguaucaccgccaucacuguc -continued gcgauggagccugcaaaguccacaucgacccaaauugccggugugggaaugcugauucauuucaguc ugccaccuacaacgguuuugggaacguguuuaagaaaaugcgcgcuuugaauuucgugagacgcucgg cgcccggaggcaaucuucagguacgcuggccuaucaauauggacuggaucuccgcauccgacacggac aaggauagcacaaaagugcccucgcuauucuuugccgugaccaacccaggugugaucgaaaccaaaca aggggacagugaggccugguuggaaugggaguuggagcuggaguacauaguuggaggcuaggaacgac ugcccgcuugagaucgacucuccgguggugagguaccacccacucagcugugucagccgguuggagaa acucuggugcgauagcacuguuggccccugccuagcgugugcuguggggaaagccccaacagauuugug aaacacuggaguugucgacccgcgagacgugcggcucgaguugucgcuucccgugagggggcugcc gggggguagagaaauauuccgguauuuauccgcuaagaccuacgcgcgacgaaacuggcg Note that iRNA relatives (e.g., iRNA r1, iRNA r2, and iRNA r3) may comprise conserved polynucleotide sequence(s) (bolded and underlined above): auagcacug (SEQ ID NO: 4); and/or gauuuguga (SEQ ID NO: 5). For example, the iRNA molecule comprises both of conserved polynucleotide sequence(s): auagcacug (SEQ ID NO: 4); and gauuuguga (SEQ ID NO: 5).

In addition, iRNA relatives (e.g., iRNA r1, iRNA r2, and iRNA r3) may comprise conserved polynucleotide sequence(s) (bolded and underlined above): cguuc (SEQ ID NO: 10); gaacg (SEQ ID NO: 11); gguuca (SEQ ID NO: 12); ggag (SEQ ID NO: 13); and/or aaauggga (SEQ ID NO: 14). For example, the iRNA molecule comprises all of conserved polynucleotide sequence(s): cguuc (SEQ ID NO: 10); gaacg (SEQ ID NO: 11); gguuca (SEQ ID NO: 12); ggag (SEQ ID NO: 13); and aaauggga (SEQ ID NO: 14).

Further, iRNA relatives (e.g., iRNA r1, iRNA r2, and iRNA r3) may comprise conserved polynucleotide sequence(s) (bolded and underlined above): ucgacg (SEQ ID NO: 15); and/or cuccga (SEQ ID NO: 16). The iRNA molecule may comprise both conserved polynucleotide sequence(s): ucgacg (SEQ ID NO: 15); and cuccga (SEQ ID NO: 16). In some embodiments, the iRNA molecule are highly related to CYVaV (or to iRNA r1, iRNA r2, or iRNA r3), and comprise a polynucleotide sequence having 50%, 60%, 70% or more identity for the recoding site for synthesis of RdRp thereof, e.g., 75% or 85% or 90% or 95% or 98% identify of the RdRp of CYVaV (or of iRNA r1, iRNA r2, or iRNA r3).

Thus, in accordance with disclosed embodiments, an RNA vector (e.g., derived from an iRNA molecule) comprises a frameshift ribosome recoding site for synthesis of the RNA-dependent RNA polymerase (RdRp). In addition, the RNA vector may include a 3' end comprising a polynucleotide sequence that terminates with three cytidylates ( . . . CCC). The penultimate 3' end hairpin may also contain three guanylates in the terminal loop ( . . . GGG . . . ). Further, the 3' CITE includes an extended hairpin or portion thereof that binds to Eukaryotic translation initiation factor 4 G (elF4G) and/or Eukaryotic initiation factor 4F (elF4F).

In certain embodiments, an RNA vector comprises a 3'CITE comprising conserved sequences auagcacug (SEQ ID NO: 4) and gauuuguga (SEQ ID NO: 5). The RNA vector may also comprise one or more of the following polynucle-otide sequences (conserved sequences of identified iRNA molecules): cguuc (SEQ ID NO: 10) and gaacg (SEQ ID NO: 11); and/or gguuca (SEQ ID NO: 12) and ggag (SEQ ID NO: 13); and/or aaauggga (SEQ ID NO: 14). Alterna-tively, or in addition, the RNA vector may comprise one or both of the following polynucleotide sequences (conserved sequences of identified iRNA molecules): ucgacg (SEQ ID NO: 15) and cuccga (SEQ ID NO: 16).

Identified iRNA relatives all have inserts in the 3'UTR and other nucleotide changes that result in the generation of an ORF that encodes a protein (p21.2) of unknown function. One differentiating characteristic of iRNAs such as CYVaV from any plant virus (FIG. 2) is that iRNAs do not encode any movement protein(s), which is characteristic of all known plant viruses including umbraviruses. Nor do iRNAs such as CYVaV require any helper virus for systemic movement through plants, including tested citrus and *Nico-tiana benthamiana* (a laboratory model plant).

In contrast, PEMV2, as with all umbraviruses, encodes for two movement proteins: p26 (long-distance movement) and p27 (cell-to-cell movement) (FIG. 3, Panel A). p26 is also a stabilization protein that protects the genome from nonsense mediated decay (NMD), and is required for accu-mulation at detectable levels of PEMV2 in single cell protoplasts (Gao, F. and Simon, A. E. (2017), *Differential use of 3' CITEs by the subgenomic RNA of Pea enation mosaic virus* 2, Virology 510:194-204). Umbraviruses are unusual viruses as they do not encode a coat protein or RNA silencing suppressor, but rather rely on a helper virus for these functions. For PEMV2, the helper virus is the enamo-virus PEMV1.

The polynucleotide sequence of PEMV2 is presented below (SEQ ID NO:23):

ggguauuuau agagaucagu augaacugug ucgcuaggau caagcggugg uucacaccug acuucacccc uggcgagggc gugaagucua gagcucaacu ggaaagagag cuggauccca ccugggcgcu ucucgugugc caagaacgag cgcgucguga ugcugacagu auugcuaaug agugguacga gggcagcaug gagugcaacc uccuuauccc ucggcccaca accgaggaug uauuuggccc cuccaucgcc ccugagccug uggcucuagu ggaggaaacu acccguuccc gcgcgccgug cguggauguc ccugccgagg aguccuguaa gucagcggag auugauccug -continued

```
uugaucucgc caaguucgac ucccuccauc gucgccuguu ggcugaagcc aacccuugca gggaaauggu ucugugggug ccuccuggcc uaccagcaga gcgcgacguc cugcccaggg cacgugggu gauaaugauc cccgaagucc cugccucugc acauaccuug uccgugaagg uuauggaggc ugugcgguug gcacaggaag ucuuggcauc ccuugccaag agggccuuag agaaaaggc uacaccaacc cuuaccgccc aggcccagcc agaggcuacc cugucggggu gcgacaccc guaucaggag acuggagcag cagccgcgug gauaacgccu ggcugcauug ccauggagcu cagagccaaa uuuggcgucu gcaaacgcac ccccgcaaac uuagagaugg ggagucgcgu cgcccgcgag cuccugcggg auaacugugu cacuugcagg gagaccacgu gguacaccag ugccauugcu guggaccugu gguugacccc gaccgucguc gaccuggccu guggccggcg agcggcggau uuuugguagg ggcugugcug ccucggcugg gggaagacac cagugugcgg uuugacaacc ugcaccccag caucgaggua aucaaggcgg cuaggccccg cccaacccag aggaugucgu uccaaaucga cguugugcgu ccucuuggag auuuuggugu gcacaacaac ucccuuguua accuagccag gggaauuaau gaaagggugu ucuacacgga caaugcuagg acagaacccc uccagccuaa gguucccuuc cccucaucac gggagcuaaa aaccuucaga gucacccuu ggaccaugga uaggguugug gagaguuaca cagggcccca gcgcacucgc uaugcuaacg cgcgggacag cauauuaucc aacccucuga gucccaaaga ugcgcgggc aagacguuug ucaaagcuga aaagauaaau uucacagcca aaccugaccc cgccccucgu gugauacagc cuagggaucc acgauucaac auugccugg cuaaauacau caagccuuug gagccaaugu uguacaaagc acuggggaaa cuuuacaagu accccgcagu ugcuaagggg uuuaacgcgg uugagacggg ggagaucauc gccggcaagu ggcggugcuu caaagauccu gucgucgugg gauuagacgc uucccgauuu gaucagcaug uaucugucga ggcguugcag uucacccacg cgguguacag aggguucauc aagucacggg aguuuaacaa ccuccuacag augauguaca ccaaccgugg ccuagggucc gcuaaggacg gauucguccg uuacaagguu aaaggguagac gcaugagcgg ugacauggac accuccuugg gcaacugugu gcucaugug uugcucacca ggaaccuuug caagguucua ggcaucccgc acgagcucuu caacaauggu gaugauugca ucgucuuuuu cgaucguugc cacuuggaga aguucaacaa ugcugucaag acuuauuuug cggaccuagg guuuaagaug aagguggaac cgccgguuga cguguuggag aaaauagagu ucugccaaac gcagccuauc uaugacgggg agaaguggcg caccgugcgu ugcaucucga guaucggaaa agauuugcuca uccguuauua guugggacca auuggagggg ugguggaaug ccaucgccca gagguggcug gcugugugug gcggaaugcc gauauacacg ucguucuacc gguggcuagc acgggccggu aagaguggga ccaaguguca gucacacccc uuguggaaaa acgagggguu gaauuugguac aggaugggga uggaccuuuc ucaugagguu aauguuacc cucaggcgcg ccugucuuc uucgcgggu uugguauuuc cccccgaug caggucgcca uugaggcgcu guaugacaag cugccuccac cguccccca ccaugguccu ccgguuaagg cguuaacaca gcgagguuc accaauuauu ucacgccgga
```

<u>aagcgccugu guuagcauga gcacgaauga agacaacaaa ucugacuuug cuguuuacgg</u>

<u>cccgugccu acagugaugu cucuuugugc ucaguguuag gcucuuaaau uuuagcgaug</u>

<u>gcgugacacg guuacacccu gaauugacag gguacagauc aagggaagcc gggggagucac</u>

<u>caacccacc ugaaucgaca gggcaaaaag ggaagccggg caccgcccac guggaaucga</u>

<u>ccacgucacc uuuucgcguc gacuaugccg ucaacacccu uucggcccgc cagccuagga</u>

<u>caauggcggu agggaaauau aug</u>acgauaa ucauuaaugu caauaacgac gagcgcaagc

-continued

```
aaccagaagg agcuacuggc agcucuguac ggcgagguga caauaaaaga acucgaggaa acaaaccucg gagucaucac cccgguucgc gcgaacgaaa agguuacaau caccccucuc cuacccccaa aaacucaaag cagggucagc uccguacuga agcgguucag gagcacccga aacacggggg gacugcuuuc cguagagaaa guggugguag uguucacccc ucacaucccc gacgacgugc uaggagaggu ggagauaugg cuccacgaca gcauccuccc ccaccucggg agcgucggac caagacugaa acucaagcug agcgaagggc ccaagcucuu agcguucuac ccacccuacu cgauugcauu gggggacucg aucucgggcc agccgagguc cuucuccauu gucaccgagc uguucgaagg caacuucgca ccggggugca gcccauucag ccuguuccuc auuggaguc cacgcaucga agcagugacc cacaacuacu ugagucgucc accacgugcu cugccaauuu gcagaacgau ggugcgggac gcguuaucgg agguggcauc ccaacagcaa uaccugaagg gagcgauguc gaacaggguau gccaugccuc ucacuacggg ugauggccag cauagagcca ugaagggggc ucccagugcc cuuccaccaa cgggggugug uacccaggcu ucuaagugag gcuucgcuuc ccgccggaag accgcggcgg uucuguuccu cccacaggag uacggcaaca acccaccuug ggaaaguggg gaccccagca cuaacuccuu uaacuaggcg ggcguguugg uuacaguagg aggggacagu gcgcaucgaa acugagcccc accacaacuc ucauccacgg ggugguuggg acgcaggugu cggagggauc gccagcccuc aggauaguga gcucccgcag agggauaagc uaucucccug cgacguagug guagaacacg ugggauaggg gaugaccuug ucgaccgguu aucgguccccc ugcuccuucg agcuggcaag gcgcucacag guucuacacu gcuacuaaag uugguggugg augucucgcc caaaaagauc acaaacgcgc gggacaaggu cccuuccacc uucgccgggu aaggcuagag ucagcgcugc augacuauaa cuugcggccg auccaguugc acgacuggug guccccccuca gugucucggu ugucugccga gugggcggug gucggauucc accacacccu gccacgaggu gcguggagac uuggccaguc uaggcucguc guaauuaguu gcagcgacgu uaaucaaccc guccgggcau auaauaggac cgguugugcu ucuuccuccc uucuuagcca ggugguuacc ucccuggcgc cc
```

The polynucleotide sequence of the intergenic plus region of PEMV2 (bolded and underlined above) is presented below (SEQ ID NO:24):

```
guuagcauga gcacgaauga agacaacaaa ucugacuuug cuguuuacgg cccugugccu acagugaugu cucuuugugc ucaguguuag gcucuuaaau uuuagcgaug gcgugacacg guuacacccu gaauugacag gguacagauc aagggaagcc ggggagucac caacccaccc ugaaucgaca gggcaaaaag ggaagccggg caccgcccac guggaaucga ccacgucacc uuuucgcguc gacuaugccg ucaacacccu uucgccccgc cagccuagga caauggcggu agggaaauau aug
```

The polynucleotide sequences of recoding frameshift sites of PEMV2 (bases 881 to 1019; see also FIG. 10) is presented below (SEQ ID NO: 25):

```
gaccgucgucgaccuggccguguggccggcgaggg cggauuuuuggguaggggcugcugugccucggcug ggggaagacaccagugugcgguuugacaaccugc accccagcaucgagguaaucaaggggcuaggccc c
```

Figure 5:
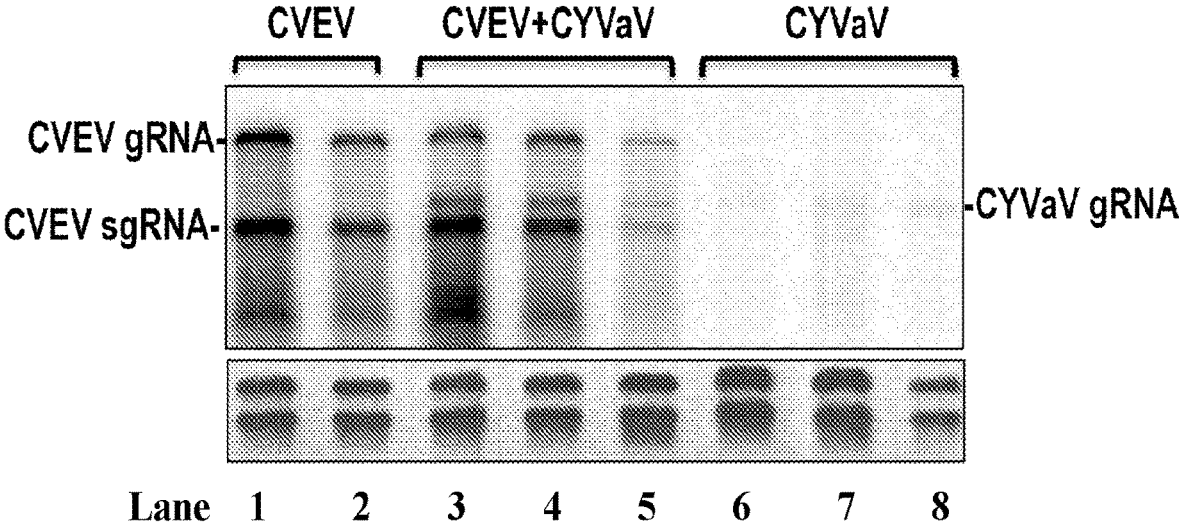
FIG. 5 shows RNA levels from agro-infiltrated leaves of *Nicotiana benthamiana*. CVEV (lanes 1-2), CVEV+CYVaV (lanes 3-5) and CYVaV (lanes 5-8) in leaves of *Nicotiana benthamiana*. Accumulation of CYVaV increased substantially in the presence of putative helper virus CVEV. Plus-strands are shown above. IRNA loading controls are shown below: p14 silencing suppressor was co-infiltrated in all leaves.
Figure 6:
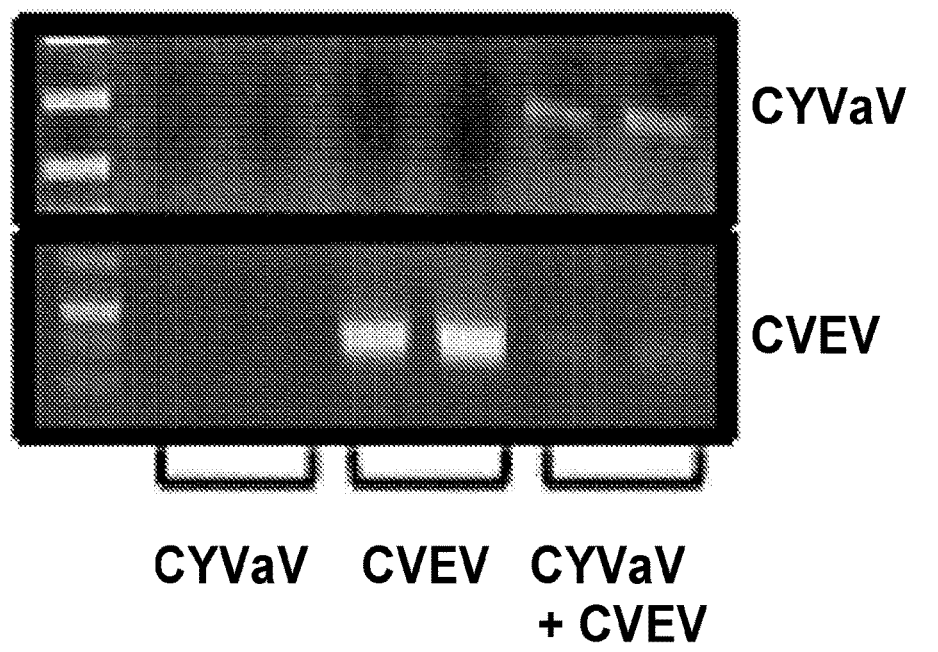
FIG. 6 shows RNA levels from another experiment with agroinfiltrated leaves of *Nicotiana benthamiana*. CYVaV or CVEV or CYVaV+CVEV agroinfiltrated into leaves of *N. benthamiana*. CYVaV was encapsidated in virions of CVEV, and virions were isolated one week later and the encapsidated RNAs subjected to PCR analysis.

CYVaV unexpectedly replicates very efficiently in *Arabidopsis thaliana* protoplasts despite not encoding p26 (or any other movement protein), which is required for accumulation of PEMV2 because of its ability to also counter NMD (see, e.g., May et al. (2020) "*The Multifunctional Long-Distance Movement Protein of Pea Enation Mosaic Virus 2 Protects Viral and Host Transcripts from Nonsense-Mediated Decay*," mBio 11:300204-20. Indeed, CYVaV was unusually stable, much more stable than most traditional viruses. CYVaV also produced an astonishingly high level of p81 in wheat germ extracts, at least 50-fold more than the p94 orthologue from PEMV2 (FIG. 3, Panel C). When CYVaV was agro-infiltrated into leaves of *Nicotiana benthamiana*, it replicated in the infiltrated tissue but accumulation was relatively weak (FIG. 3, Panel B, top; FIG. 5, lanes 6-8). No replication was achieved with manual inoculation. However, when CYVaV was co-infiltrated with the enamovirus Citrus vein enation virus (CVEV), accumulation improved substantially in these cells (FIG. 5, lanes 3-5; see also FIG. 6). In citrus, yellowing symptoms of CYVaV+ CVEV (FIG. 7, Panel B) were more vibrant as compared to symptoms exhibited by CYVaV alone (FIG. 7, Panel A).

CYVaV had no synergistic effect with any other combination of citrus virus tested. Additional studies showed that CVEV may be utilized as a helper virus for CYVaV in order to allow for transmission from tree to tree. CVEV was likely responsible for the presence of CYVaV in the original limequat trees: however, CVEV is known to be very heat sensitive and thus was likely lost from the limequat trees during a hot summer.

CYVaV moved sporadically into upper, uninoculated leaves and accumulated at extremely high levels, sometimes visible by ethidium staining on gels. Symptoms that began in the ninth leaf of the major bolt comprised stunting, leaf curling, and deformation of floral tissue. Leaves in axillary stems also began showing similar symptoms around the same time. This astonishing result demonstrated that CYVaV moves systemically in the absence of any encoded movement protein(s), which is not possible by traditional plant viruses. Experiments showed that CYVaV moves systemically in *N. benthamiana* and is strictly confined to the phloem, replicating only in companion cells and phloem parenchyma cells. In citrus, CYVaV is 100% graft-transmissible, but difficult to transmit in other forms.

Fluorescence in situ hybridization (FISH) of symptomatic leaf tissue and roots confirmed that CYVaV is confined to phloem parenchyma cells, companion cells and sieve elements (FIG. 8, Panels A-G), which is characteristic of a phloem-limited virus. CYVaV levels were extremely high in the petioles of symptomatic tissue and sometimes visible in ethidium-stained gels of total RNA. Although symptoms are more severe in *N. benthamiana*, CYVaV has been found to be virtually symptomless in all varieties of citrus tested. Indeed, the most severe symptom was found on citron, the indicator tree for citrus viruses, and consisted of very minor gold flecking on leaves scattered throughout the tree.

Phloem-limited movement of CYVaV explains why it is readily graft-transmissible, but not easily transmissible by any means. CYVaV lacks any encoded movement protein(s) as noted above. Instead, CYVaV utilizes host plant endogenous movement protein phloem protein 2 (PP2), and the pathway for transiting between companion cells, phloem parenchyma cells, and sieve elements. In addition, since host range is believed to involve compatible interactions between viral movement proteins and host plasmodesmata-associated proteins, it is believed that CYVaV is capable of transiting through the phloem of numerous other woody and non-woody host plants using PP2 as it is a very conserved host endogenous movement protein(s). As such, CYVaV provides an exceptional model system for examining RNA movement (e.g., in *N. benthamiana* and/or citrus) and for use as a vector for numerous applications. Experiments confirmed that CYVaV moves systemically in a host plant and is limited to the phloem, and is readily graft-transmissible but not readily transmissible between plants in other forms.

Systemic infection by CYVaV was also observed in tomato, cucumber and melon. Referring to FIG. 28, Panel A shows an uninfected cucumber plant (mock) and a plant infected by CYVaV by way of agroinfiltration about two months earlier, both grown under the same conditions. The infected plant shows effects of CYVaV infection indicating systemic movement of CYVaV and systemic infection of the cucumber plant. In the infected plant, the stem distance between nodes is drastically reduced such that multiple flowers are located in a cluster. This sign of infection is also observed in *N. benthamiana* and appears to be characteristic of CYVaV infection of some rapidly growing plants. FIG. 28, Panel B, shows an uninfected tomato plant and a tomato plant infected with CYVaV about 53 days earlier, both plants grown under the same conditions. The tomato plant was infected by injecting sap from a CYVaV-infected *N. benthamiana* plant into the vasculature of the tomato plant. The infected plant shows a lack of growth indicating systemic movement of the CYVaV and systemic infection of the tomato plant. The infection of *N. benthamiana*, cucumber, tomato and other plant species mentioned herein, and the natural occurrence of CYVaV and iRNA relatives, indicates that iRNA appear have a wide host range. The ability of CYVaV to bind to phloem protein 2 (PP2), as described herein, also suggests a wide host range since PP2 is found in an extremely large number of plant species and may provide a means for systemic movement of CYVaV and other iRNA through many plant types.

Citrus trees have a complex reproductive biology due to apomixis and sexual incompatibility between varieties. Coupled with a long juvenile period that can exceed six years, genetic improvement by traditional breeding methods is complex and time consuming. The present disclosure overcomes such problems by providing an iRNA-based (e.g., CYVaV-based) vector engineered to include therapeutic siRNA inserts. iRNAs such as CYVaV are unique among infectious agents given they encode a polymerase yet move like a viroid (small circular non-coding RNA that also uses PP2 as a movement protein), and thus are capable of transiting through plants other than citrus. Thus, in addition to citrus, the iRNA-based vectors of the present disclosure may be developed for other woody plants (e.g., trees and legumes), and in particular olive trees and grapevines.

In accordance with disclosed embodiments, CYVaV is utilized in the development of a vector for delivery of small RNAs and proteins into citrus seedlings and *N. benthamiana*. The procedure utilized for CYVaV vector development was similar to that utilized by the present inventors for engineering betacarmovirus TCV to produce small RNAs (see Aguado, L. C. et al. (2017), *RNase III nucleases from diverse kingdoms serve as antiviral effectors*, Nature 547: 114-117). Exemplary and advantageous sites for adding one, two, three, or more small RNA inserts designed to be excised by RNase III-type exonucleases were identified. Exemplary sites include positions 2250, 2301, 2319, 2330, 2336, 2083 and 2375. A small hairpin was expressed directly from the genome that targets GFP expressed in *N. benthamiana* plant 16C, which silenced GFP.

In accordance with disclosed embodiments, iRNA vectors disclosed herein may contain small RNA inserts with various functionality including: small RNAs that target an essential fungal mRNA; small RNAs that target an insect for death, sterility, or other incapacitating function; small RNAs that target gene expression in the host plant; small RNAs that target plant pathogenic bacteria; small RNAs that target CTV; and small RNAs that target CVEV (as this virus together with CYVaV causes enhanced yellow-vein symptoms) or other virus pathogen(s). In addition, the disclosed vectors may include other small RNAs and/or therapeutic agents known in the art. Thus, a phloem-restricted iRNA-based vector may be engineered to produce small RNAs that have anti-bacterial and/or anti-fungal and/or anti-insect and/or or anti-viral properties, which provides for a superior treatment and management strategy compared to current methodologies.

CYVaV vectors may be applied manually to infected or uninfected trees by cutting into the phloem and depositing the vector either as RNA, or by agroinfiltration, or after encapsidation in the coat protein of CVEV or another virus, following citrus inoculation procedures well known to those of skill in the art, e.g. such as procedures developed and used routinely under the Citrus Clonal Protection Program (CCPP). Such procedures are routine for inoculation of CTV and other graft-transmissible pathogens of citrus. Since CYVaV does not encode a capsid protein, no virions are made and thus no natural tree-to-tree transmission of CYVaV is possible. When CYVaV is encapsidated in CVEV or other viral coat protein, no other component of CVEV or other virus is present.

A plant may be infected with an iRNA-based vector by way of agroinfiltration without cutting onto the phloem, for example by agroinfiltration into the leaves of the plant. An iRNA-based vector is not a mere replicon that, once injected into a plant cell, is not expected to leave the plant cell. The goal of agroinfiltration of an iRNA-based vector into, for example, the leaf of a plant is not to install the iRNA-based vector in plants cells near the agroinfiltration site, but rather to have at least some of the iRNA-based vector reach the plant's vasculature and thereafter move systemically through the plant. Typically when agroinfiltrated into the leaf of a plant only a portion of the agroinfiltrated iRNA-based vector will reach the plant vasculature and be effective for infecting the plant. In the case of plants recalcitrant to agroinfiltration, the agroinfiltration may be performed first in a related species more susceptible to agroinfiltration followed by grafting from the more susceptible species to the target species. For example, *Citrus limon* may be more susceptible to agroinfiltration than various species of orange trees. Alternatively or additionally, a species recalcitrant to agroinfiltration may be pretreated to make them more susceptible to agrofiltration. For example, agroinfiltration into Citrus plants may be facilitated by first inoculating the intended agroinfiltration site with an actively growing culture of *Xanthomonas citri* subsp. *citri* (Xcc) suspended in water, as described for example in Jia and Wang (2014). Xcc-facilitated agroinfiltration of citrus leaves: a tool for rapid functional analysis of transgenes in citrus leaves. Plant Cell Rep. 33:1993-2001.

When infecting the vasculature of a plant directly, for example by way of contact with a cut in the phloem, the iRNA-based vector may be stabilized with a capsid protein of another type of virus. In some examples, the iRNA-based vector is encapsidated with the coat protein of CVEV, which is believed to be a helper virus able to encapsidate CYVaV in nature. In some examples, one or more iRNA-based vector molecules are encapsidated in a self-assembling capsid protein not naturally associated with CYVaV. For example, methods of assembling capsid protein from cowpea chlorotic mottle virus with RNA molecules of various sizes are described in Cadena-Nava et al. 2012. Self-assembly of viral capsid protein and RNA molecules of different sizes: requirement for a specific high protein/RNA mass ratio. J. Virol. 86:3318-3326.

Once a first plant has been infected with an iRNA-based vector, another plant may be infected by grafting a part of the first plant to the other plant, or by injecting sap from the first plant into the other plant, or by linking the phloem of two plants through a parasitic dodder plant. Grafting in particular allows for transferring the iRNA-based vector over long distances and with long periods of time (e.g., one day or more) between cutting the graft from the first plant and adding the graft to the second plant. In some examples, an iRNA-based vector is transferred between strains or species by way of sap taken from a plant of one strain or species and injected into the vasculature of another plant of a different strain or species. In some examples, an iRNA-based vector is transferred between strains or species by way of a graft taken from a plant of one strain or species and grafted to another plant of a different strain or species.

A first plant (optionally called in some cases a mother tree) infected with an engineered iRNA-based vector can be used to produce grafts for transmitting the iRNA-based vector to other plants either as a preventative or to treat an infection already present in the other plant. The first plant can also be used to produce seedlings (for example by grafting from the first tree to seedlings of the first plant or another plant) which are used to propogate plants having the iRNA-based vector. Once in a seedling, the iRNA-based vector replicates and moves through the plant as it grows.

As noted above, CYVaV has only two ORFs: a 5' proximal ORF that encodes replication-required protein p21; and a frame-shifting extension of p21, whereby a ribosome recoding element allows ribosomes to continue translation, extending p21 to produce p81, the RNA-dependent RNA polymerase. The organization of these two ORFs is similar to the organization of similar ORFs in viruses in the Tombusviridae and Luteoviridae. However, all viruses in these families, and indeed in all known plant RNA viruses, encode movement proteins or are associated with a secondary virus that encodes a movement protein(s). The ability to encode movement proteins, or associate with a second virus that encodes a movement protein(s), had long been considered a requirement for movement from cell-to-cell and also for transiting through the phloem to establish a systemic infection. As such, the use of iRNAs as vectors had not been proposed, and indeed iRNA molecules were previously considered unsuitable for use as an independent vector due to the lack of any encoded movement protein and belief that they were not independently mobile.

As such, the capacity for independent systemic movement of iRNAs throughout a plant's phloem despite not coding for or depending on any exogenous movement protein(s) is quite surprising. The CYVaV-based vectors of the present disclosure unambiguously and repeatedly demonstrated (via fluorescence in situ hybridization and other techniques) systemic movement without the aid of any helper virus. Young, un-infiltrated (systemic) tissue displayed highly visible symptoms on *N. benthamiana*, including leaf galls and root galls. The disclosed vectors utilize endogenous host movement protein(s) for mobility. In this regard, host phloem protein(s) (25 kDa phloem protein 2 (PP2) and/or 26 kDa *Cucumis sativus* phloem protein 2-like) known to traffic host RNAs into sieve elements (see Balachandran, S. et al. (1997), *Phloem sap proteins from Cucurbita maxima and Ricinus communis have the capacity to traffic cell to cell through plasmodesmata*, PNAS 94(25): 14150-14155; Gómez, G. and Pallás, V. (2004), *A long-distance translocatable phloem protein from cucumber forms a ribonucleoprotein complex in vivo with Hop stunt viroid RNA*, J Virol 78(18): 10104-10110) were likely shown to interact with CYVaV using Northwestern blots in vitro and RNA pull-downs from infected phloem sap in vivo. Thus, since known plant viruses encode (or are dependent on) a movement protein, iRNAs are quite different structurally and functionally from traditional plant viruses.

In addition to CYVaV, other RNAs of similar size and that encode a polymerase may be utilized in the develop of similarly structured iRNA-based vectors (see, e.g., Chin, L. S. et al. (1993). *The beet western yellows virus ST9-asso-*

*ciated RNA shares structural and nucleotide sequence homology with Tombusviruses.* Virology 192(2):473-482; Passmore, B. K. et al. (1993). *Beet western yellows virus-associated RNA: an independently replicating RNA that stimulates virus accumulation.* PNAS 90(31): 10168-10172). As noted above, other iRNA relatives (e.g., iRNA r1, iRNA r2, and iRNA r3, identified in Opuntia, Fig trees, and Ethiopian corn, respectively) and that encode proteins p21 and p81 (FIG. 4) may be utilized for vector development.

Although CYVaV is present in the GenBank database (GenBank: JX101610), iRNAs do not belong to any known classification of virus given they lack cistrons that encode movement proteins. Nor are iRNAs dependent on a helper virus for systemic movement within a host. Moreover, iRNAs lack cistrons that encode coat proteins. iRNAs are also dissimilar to viroids, although both are capable of systemic movement in the absence of encoded movement proteins. Viroids are circular single stranded RNAs that have no coding capacity and replicate in the nucleus or chloroplast using a host DNA-dependent RNA polymerase. The vast majority of the tiny viroid genome, typically including about 300 to 400 nucleotides (nt), is needed for the viroid's unusual existence. In addition, viroids do not code for any proteins, which makes them unsuitable for use as vectors. In contrast, iRNAs code for their own RNA-dependent RNA polymerase (RdRp).

iRNAs may be categorized in two classes: a first class is characterized by a frameshift requirement to generate the RdRp and RNA structures proximal to the 3' end that resemble those of umbraviruses. A second class is characterized by a readthrough requirement to generate the RdRp and 3' RNA structures that resemble those of Tombusviruses. CYVaV is a member of the first class with properties similar to umbraviruses including a frameshifting recoding site and similar structures at the 3' end, and similar sequences at the 5' end. iRNA members of the second class have always been discovered in association with a helper virus.

iRNAs provide a number of benefits as compared to conventional viral vectors. For example, iRNAs are relatively small, making them easier to structurally and functionally map and genetically manipulate. In contrast, viruses such as CTV are 8-fold larger, making them more cumbersome to use as a vector. iRNAs can replicate and accumulate to unexpectedly high levels (e.g., visible by ethidium staining on gels and 4% of reads by RNAseq), which is critical for the vector's ability to deliver a sufficient amount of therapeutic agent(s) into the target plant. In addition, iRNAs are much more stable than many viruses despite not encoding a coat protein or silencing suppressor (FIG. 13), which allows for a long lifespan in the host plant and thus provides benefit over an extended period.

iRNAs are also limited to the host's phloem, which is especially useful for targeting pathogens that either reside in, or whose carriers feed from, or whose symptoms accumulate in, the phloem since the payload will be targeted to where it is most needed. By moving independent of movement proteins (whose interactions with specific host proteins is the primary factor for determining host range), iRNAs are able to transit within a broader range of hosts, thereby increasing the applicability of a single vector platform. Given the lack of coat protein expression and the dispensability of a helper virus for systemic plant infection, iRNAs cannot be vectored from plant-to-plant and instead must be introduced directly into the phloem via grafting. The lack of a coat protein prevents formation of infectious particles and thus unintended reversion to wild type infectious agents into the environment. This is particularly beneficial for streamlining regulatory approval as regulators are often concerned with the possible uncontrolled transmission of introduced biological agents.

iRNAs are also virtually benign in citrus, unlike viruses like CTV whose isolates can be highly pathogenic. Using a common virus as a vector, such as CTV, runs the risk of superinfection exclusion, where trees previously infected and/or exposed to that virus are not able to be additionally infected by the same virus acting as the vector (e.g., most citrus trees in the USA are infected with CTV). Thus, avoiding superinfection exclusion, at a minimum, requires additional steps to the process that makes it more expensive and cumbersome.

The present disclosure also provides for novel therapeutic, prophylactic, or trait enhancing inserts that are engineered into the iRNA vector. A variety of inserts are provided, including inserts that target a particular pathogen, an insect, or a manifestation of the disease(s). Alternatively, or in addition, inserts are provided that strengthen or improve plant health and/or enhance desired characteristics of the plant.

The disclosed infectious agents are capable of accumulation and systemic movement throughout the host plant, and can thus deliver therapies throughout a host over a substantial time period. Characteristics of the disclosed agents are therefore highly beneficial for treating numerous specific diseases. Using an infectious agent composed of either RNA or DNA has an additional advantage of being able to code for therapeutic proteins or peptides that would be expressed within infected cells and/or by engineering the infectious agent to contain a specific sequence or cleavable portion of its genetic material to serve as an RNA-based therapeutic agent.

Products with antimicrobial properties against plant pathogens can take a number of formats and are produced through ribosomal (defensins and small bacteriocins) or non-ribosomal synthesis (peptaibols, cyclopeptides and pseudopeptides). The best known are over 900 cationic antimicrobial peptides (CAPs), such as lactoferrin or defensin, which are generally less than 50 amino acids and whose antimicrobial properties are well known in the art. CAPs are non-specific agents that target cell walls generally, with reported effects against bacteria and fungi. CTV engineered with an insert designed to express defensin has received approval for release by the USDA in Florida, but its widespread efficacy is unknown. Moreover, the isolate of CTV used for the vector makes it unsuitable for trees growing in some regions (e.g., California).

RNA therapies that target viral pathogens are also in widespread development in plants. These therapies use non-coding small interfering RNAs (siRNAs), which are generated from the genome of the plant, and thus include genetic modification of the host. In addition to negative viewpoints of some growers and consumers to genetic modification of citrus trees, the length of time to generate genetically modified trees is measured in decades and may ultimately not have the same attributes (texture/color/taste) as varieties developed over decades, and thus is not a solution to current, time sensitive agricultural diseases, in addition to being very expensive to develop and potentially impacting the quality of the fruit.

siRNAs can be used to target bacteria in plants, for example the *Candidus* Liberibacter *asiaticus* (CLas) bacteria. Plant pathogenic bacteria can be targeted using siRNAs that are produced in plants, taken up by the bacteria, and directly reprogram gene expression in the bacteria as described for example by Singla-Rastogi et al. (2019) Plant small RNA species direct gene silencing in pathogenic bacteria as well as disease protection, a preprint to posted bioRxiv Dec. 3, 2019 . In some implementations, CYVaV or another iRNA based vector is provided that contains siRNA hairpins that target a bacteria such as *Candidus liberibacter asiaticus* and render the bacteria non-pathogenic. For example, an siRNA hairpin provided to a plant by an iRNA based vector may be taken up the CLas or another bacteria in the plant and control gene expression in the bacteria, thereby killing the bacteria and/or inhibiting an increase of the bacterial population. Compared to an enzybiotic which might have, for example, about 500 bases, an siRNA in the form of a hairpin is considerably smaller (<60 bases) and is more likely to be stable in an iRNA based vector.

Recently, highly targeted anti-bacterial enzymes have been developed for use in animals and humans as a replacement for current antibiotics. These enzymes are engineered from bacteriophage lysis proteins and are known as enzybiotics. As with the parental bacteriophage proteins, enzybiotics can lyse bacterial cell walls on contact, but are designed to be used external to both gram positive and gram negative bacteria. Enzybiotics are engineered to lyse only targeted bacterium, leaving other members of the microbiome unaffected. In some implementations, an iRNA vector is provided that includes a non-coding RNA insert that can be translated into an anti-bacterial protein like an enzybiotic.

In some implementations, an iRNA vector is provided that includes an RNA insert that interferes with the functionality of the insect vector at issue. Insects have an RNA silencing system similar to plants; small RNAs ingested by insects are taken up into cells and target critical mRNAs for degradation or blockage of translation within the insect. In some embodiments, a targeted insert is provided that is capable of silencing a critical reproductive function of the insect vector, resulting in sterilization of the insect. Of particular relevance are phloem-feeding insects that transmit phloem-limited pathogens, where a non-coding RNA insert into a phloem-limited vector is readily taken up by feeding insects.

In some implementations, an iRNA vector is provided that includes a non-coding RNA insert that targets a plant response to a pathogen. In some cases, bacteria deposited into a tree by an insect vector does not directly damage the tree. However, the host tree produces excessive callose in their phloem in order to isolate the bacteria, which can ultimately restrict the flow of photoassimilates and kill the tree. Thus, the RNA insert silences and/or depresses such callose production.

In some implementations, an iRNA vector is provided that includes a non-coding RNA insert that targets a virus, for example CTV. In some implementations, an iRNA vector is provided that includes a non-coding RNA insert that is taken up by a pathogenic bacteria or fungus making the non-coding RNA available to silence a critical function within the pathogen that can kill or reduce the virulence of that pathogen to its host.

In some implementations, an iRNA-based vector, e.g., an iRNA vector that includes a non-coding RNA insert, is grafted into rootstocks or seedlings in order to provide protection against a pathogen or in order to make that rootstock or seedling more robust. For example, planting citrus trees on sour orange root stock can be advantageous since trees grown on sour orange rootstock are, among other things, less affected by HLB than trees grown on many other rootstocks. The sour orange rootstock is also tolerant of a wide range of growing conditions. However, sour orange rootstock is also highly susceptible to CTV and many citrus growers abandoned sour orange rootstock after CTV outbreaks. Introducing an iRNA based vector adapted to target CTV into sour orange rootstock thereby produces rootstock that is tolerant to both CTV and HLB. The iRNA-based vector can be introduced into the sour orange rootstock, for example, by grafting a scion containing the iRNA based vector to the rootstock or by grafting a part of plant containing the iRNA-based vector to the rootstock or to a scion grafted to the rootstock. In some examples, seedlings are produce having sour orange rootstock, a scion of sour orange or another citrus species, and the iRNA-based vector containing a heterologous element that targets CTV. In some implementations, the heterologous element is a hairpin or single-stranded sequence, which includes a sequence complimentary to (though not necessarily exactly the same as) a sequence conserved within one or more strains of CTV.

In some implementations, a stable parental structure of an RNA vector (for example an RNA virus) is modified in combination with adding a heterologous element. In some embodiments, the modification may include a structurally stabilizing modification and/or a structurally de-stabilizing modification (e.g., converting G:U pairs to G:C pairs in the parental structure). In some examples, the modification may include truncating a hairpin of the parental structure. In some examples, the modification may include inserting a scaffold into the parental structure. One or more of these examples maybe combined. Without intending to be limited by theory, these modifications produce a structure that is more fit for one or more process in the infection cycle when a heterologous element is added then when the heterologous element is deleted. The RNA vector with intact heterologous element thereby replicates in greater numbers than any copies wherein the heterologous element is deleted. While described herein in relation to iRNA-based vectors used to treat plants, it is expected that these techniques may be applied to other RNA vector and used to treat plants or other organisms such as animals.

Additional characteristics and features of the present disclosure will be further understood through reference to the following additional examples and discussion, which are provided by way of further illustration and are not intended to be limiting of the present disclosure.

Figure 9:
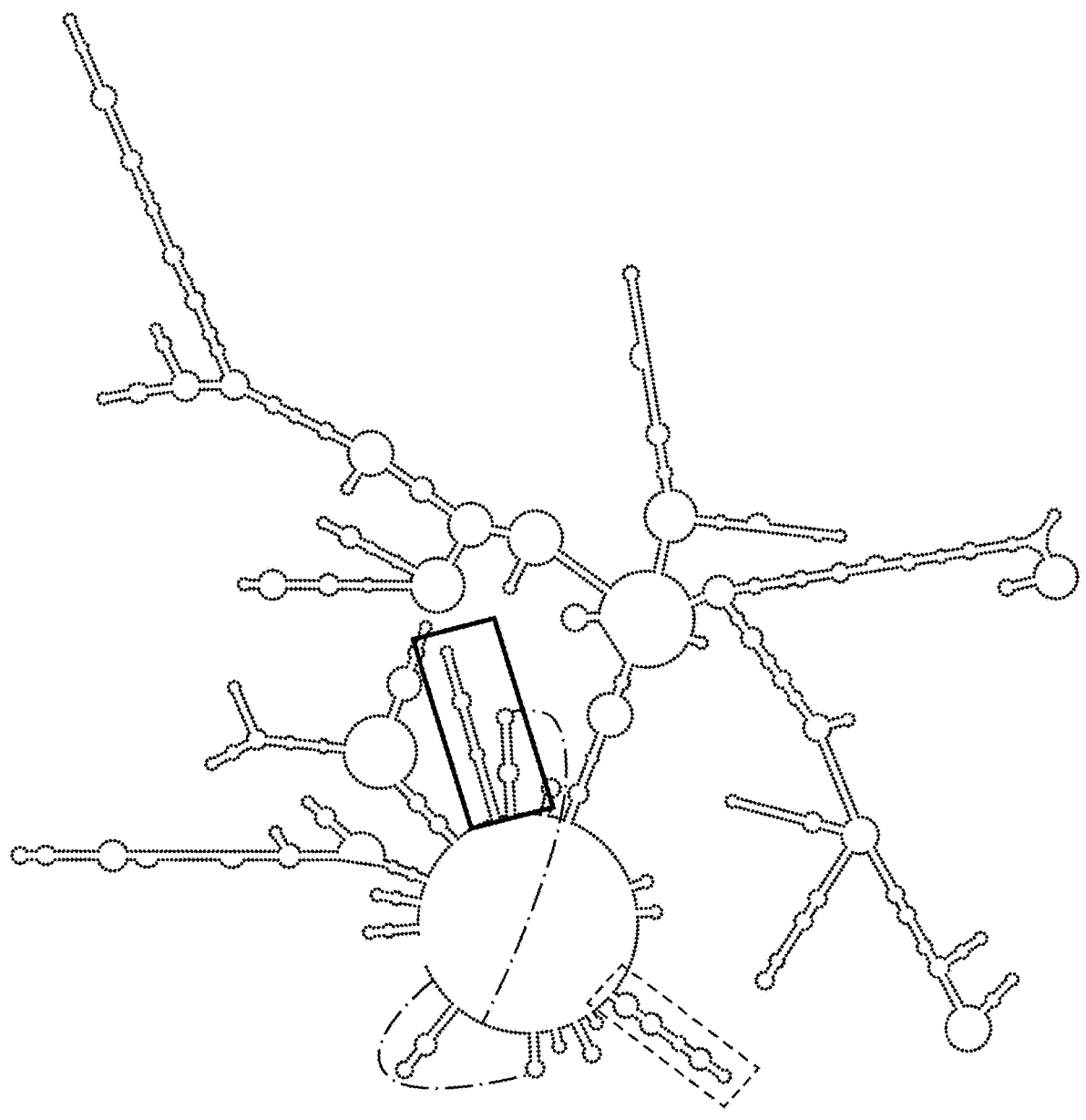
FIG. 9 illustrates schematically the full-length secondary structure of CYVaV as determined by SHAPE structure probing and phylogenetic comparisons with the CYVaV relatives in Opuntia, fig and corn. The recoding frameshift site (see FIG. 10) is identified by boxed single solid line region, and the ISS-like (I-shaped structure) 3'CITE (see FIG. 11) is identified by boxed dashed line region. For example, a region for accommodating inserted hairpin(s) is shown by boxed double line region.
Figures 11, 12:
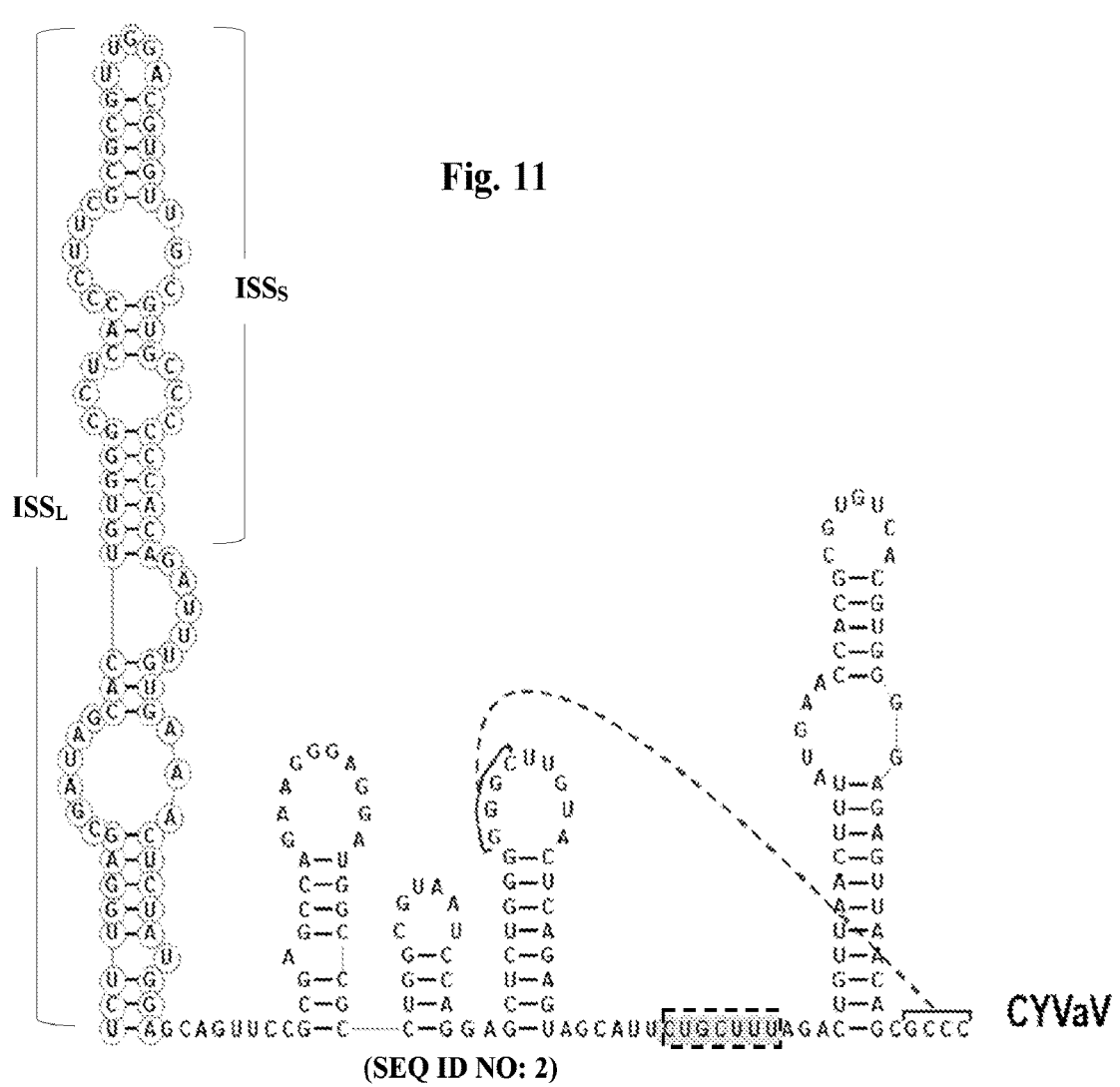
FIG. 11 illustrates schematically the ISS-like 3' Cap Independent Translation Enhancer (3'CITE) of CYVaV. The structure of the 3' end of CYVaV is shown. The 3'CITE is illustrated at the left-most portion shown and with bases circled. Sequence identified by boxed solid line engages in the long-distance RNA:RNA interaction with the recoding site.
FIG. 12 illustrates results from a trans-inhibition assay. Full-length CYVaV was translated in vitro in the presence of 10-fold molar excess of a truncated version of the ISS ($ISS_S$) or full-sized ISS ($ISS_L$).
Figure 14:
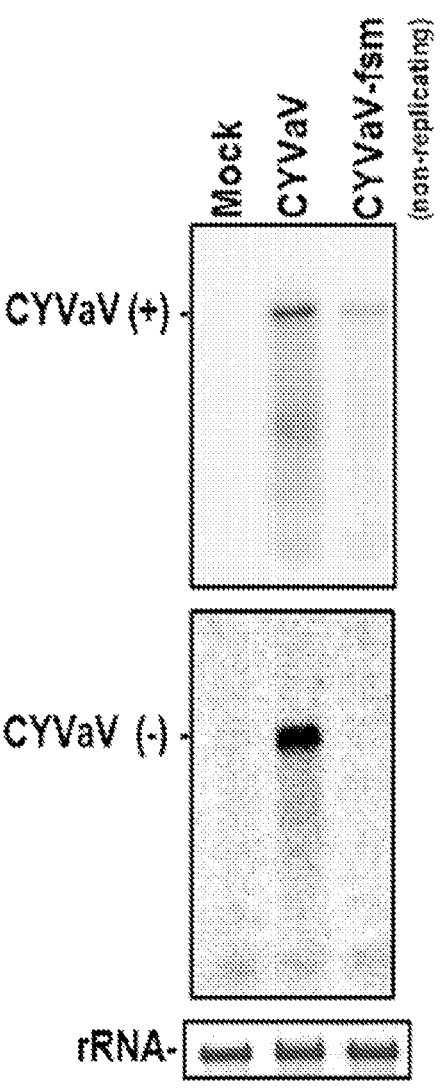
FIG. 14 demonstrates replication of CYVaV in *Arabidopsis* protoplasts. An infectious clone of CYVaV was generated. Wild-type RNA transcripts (CYVaV) or transcripts containing a mutation in the recoding slippery site that eliminates the synthesis of the RdRp (CYVaV-fsm), and thus does not replicate, were inoculated onto *Arabidopsis* protoplasts. RNA was extracted and a Northern blot performed 30 hours later. Note that inoculated transcripts of CYVaV-fsm were still present in the protoplasts at 30 hours (whereas in a traditional virus they would be undetectable after 4 hours). Plus strands are shown in Panel A, and minus strand replication intermediate is shown in Panel B.

CYVaV Structure. Full length structure of CYVaV was determined by SHAPE structure probing and phylogenetic comparisons with the CYVaV relatives in Opuntia, Fig and Corn (FIG. 9). The recoding site (see FIG. 10) and the ISS-like (I-shaped structure) 3 CITE (see FIG. 11) are identified, along with a region for accommodating an insert is, for example, shown by boxed double line region and discussed in further detail with regard to exemplary locations for inserts.

The genome organization of CYVaV exhibits some similarities to other RNA molecules, particular PEMV2 (FIG. 3, Panel A). However, umbravirus PEMV2 also possesses ORFs encoding for proteins p26 and p27 involved in movement. Levels of CYVaV plus (+) strands in infiltrated *N. benthamiana* leaves and systemic leaves are shown in FIG. 3, Panel B. Levels of the RNA-dependent RNA polymerase (RdRp) synthesized by frameshifting in vitro in wheat germ extracts of full-length CYVaV and PEMV2 are also shown (FIG. 3, Panel C). Note the significant difference in levels of p94 from PEMV2 as compared to p81 polymerase produced by CYVaV. The frameshifting site of CYVaV is one of the strongest known in virology and believed to be responsible for its exceptionally high accumulation.

CYVaV is encapsidated in virions of CVEV. CYVaV or CVEV or CYVaV+CVEV were agroinfiltrated into leaves of *N. benthamiana*. CYVaV was encapsidated in virions of CVEV, and virions were isolated one week later and the encapsidated RNAs subjected to PCR analysis (see FIGS. 5 and 6). Accumulation of CYVaV increased substantially in the presence of putative helper virus CVEV. rRNA loading controls are shown below. p14 silencing suppressor was co-infiltrated in all leaves. Yellowing symptoms were slightly more severe in citrus leaves with CYVaV+CVEV (FIG. 7, Panel B).

Figure 8:
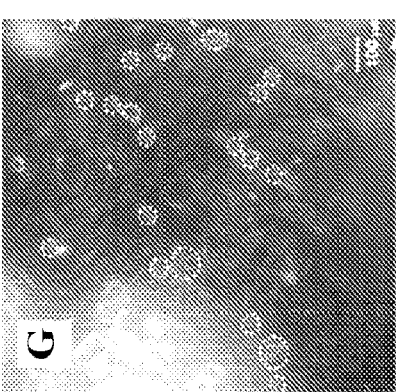
FIG. 8 shows the systemic and phloem-limited movement of CYVaV in *N. benthamiana*, wherein CYVaV is confined to the transport tissues of the plant. Fluorescence in situ hybridization (FISH) imaging detecting plus strands of CYVaV were stained pink (with areas generally shown herein with dashed white lines and circles) are shown in Panels A-G, including longitudinal and cross-sectional views of petioles (Panels A-D) and root tissue (Panels E-G). Tissue was stained with DAPI. Companion cells (CC), phloem parenchyma cells (PPC) and sieve elements (SE), and xylem (XL) are identified. Note that the iRNA is completely restricted to the SE, CC and PPC. Blue (shown herein as dark grey or black areas) is from DAPI staining of endogenous DNA. CYVaV is symptomless in virtually all tested citrus.

CYVaV is phloem-limited. Fluorescence in situ hybridization (FISH) imaging clearly detected plus strands of CYVaV, which was completely restricted to the sieve elements, companion cells and phloem parenchyma cells (FIG. 8).

CYVaV does not encode a silencing suppressor. *N. benthamiana* 16C plants were agroinfiltrated with a construct expressing GFP (which is silenced in these plants) and either constructs expressing CYVaV p21 or p81, or constructs expressing known silencing suppressors p19 (from TBSV) or p38 (from TCV) (FIG. 13, Panel A). Only p19 and p38 suppress the silencing of GFP, allowing the green fluorescence to be expressed (FIG. 13, Panel B). Northern blot probed with GFP oligonucleotide showed that GFP RNA is still silenced in the presence of p21 or p81 (FIG. 13, Panel C).

Replication of CYVaV in *Arabidopsis* protoplasts. An infectious clone of CYVaV was generated. Wild-type RNA transcripts (CYVaV) or transcripts containing a mutation in the recoding slippery site that eliminates the synthesis of the RdRp (CYVaV-fsm), and thus does not replicate, were inoculated onto *Arabidopsis* protoplasts. RNA was extracted and a Northern blot performed 30 hours later. Note that inoculated transcripts of CYVaV-fsm were still present in the protoplasts at 30 hours (whereas in a traditional virus they would be undetectable after 4 hours).

Figure 15:
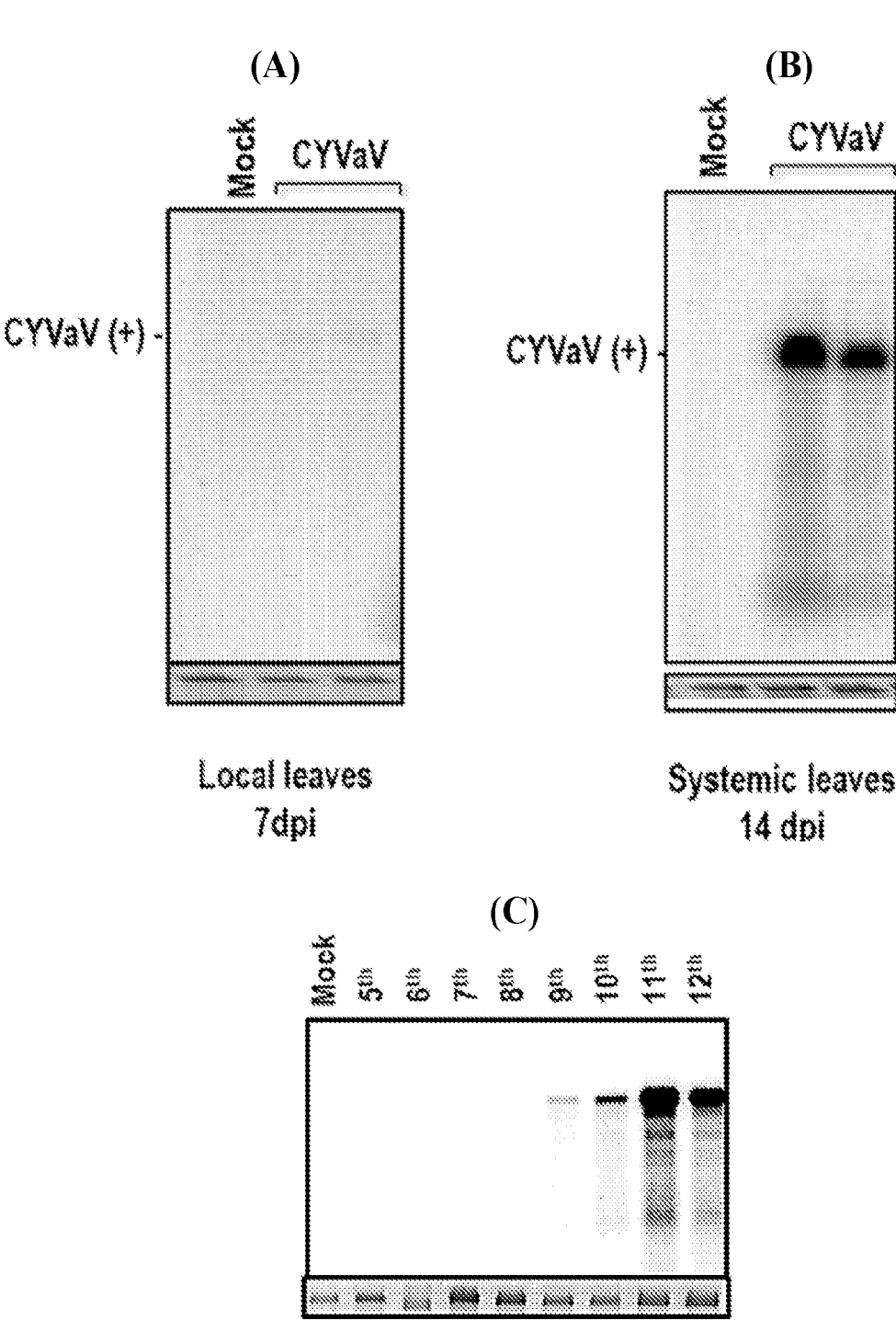
FIG. 15 demonstrates replication of CYVaV in *N. benthaminana*. Referring to Panel A, the level of CYVaV accumulating in the infiltrated leaves of *N. benthamiana* as determined by Northern blot is shown. Referring to Panel B, plants infiltrated with CYVaV sporadically showed systemic symptoms (see FIG. 16). These plants accumulated high levels of CYVaV. Referring to Panel C, the level of CYVaV in individual leaves of a systemically infected plant is shown. Leaves 4 and 5 were agroinfiltrated with CYVaV. Note the substantial accumulation of CYVaV in the youngest leaves.
Figure 16:
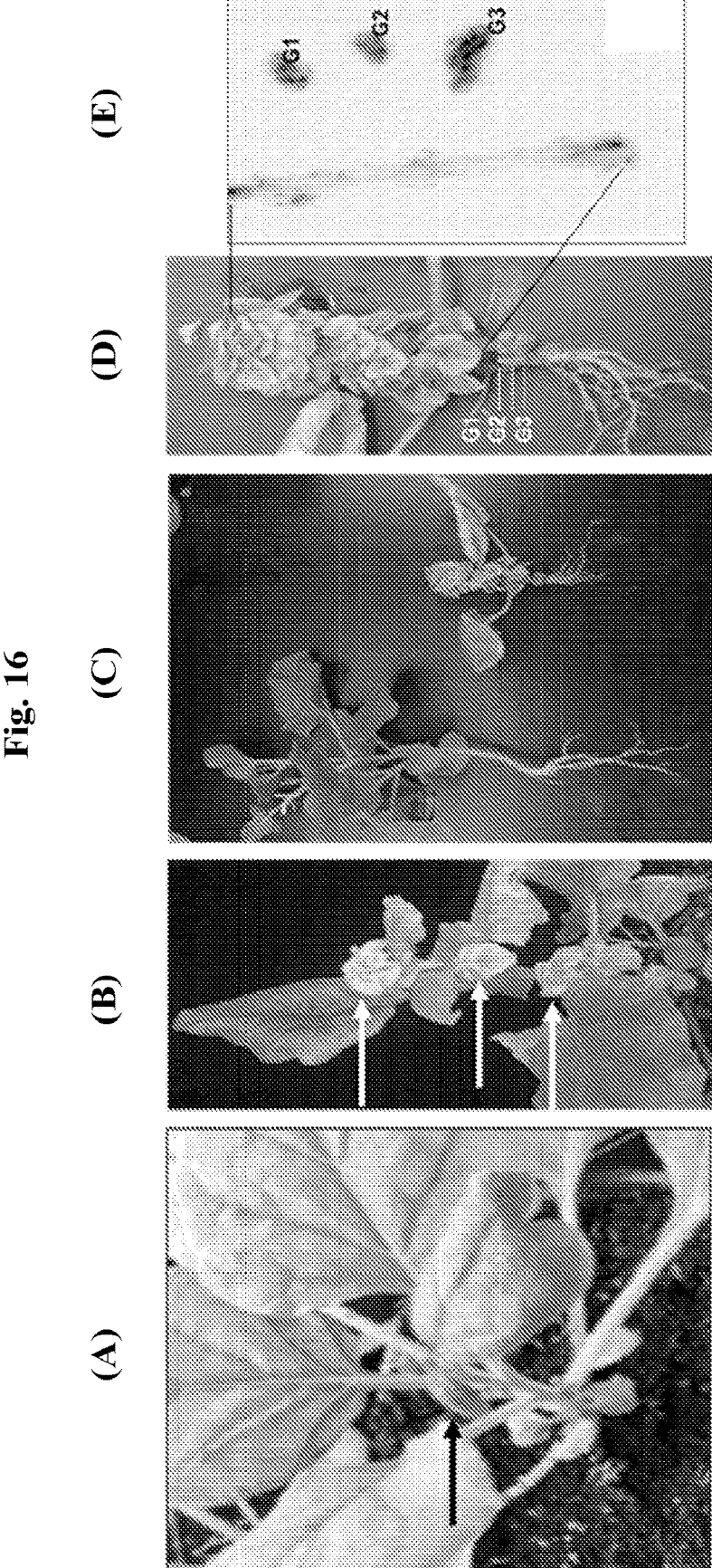
FIG. 16 show symptoms of *N. benthamiana* systemically infected with CYVaV. Leaves 4 and 5 were agroinfiltrated with CYVaV. The first sign of a systemically infected plant is a "cupped" leaf (Panel A), which was nearly always leaf 9. In the following few weeks, leaf galls emerged at the apical meristem and each node of the plant (Panel B). An uninfected plant (Panel C, left) and an infected plant (Panel C, right) of the same age are shown. Systemically infected plants also had root galls (Panel D), containing a substantial amount of CYVaV as evidenced by Northern plant blot (Panel E).

Replication of CYVaV in *N. benthamiana*. Level of CYVaV accumulating in the infiltrated leaves of *N. benthamiana* was determined by Northern blot (FIG. 15, Panel A). Plants infiltrated with CYVaV sporadically showed systemic symptoms (FIG. 15, Panel B: see also FIG. 16). These plants accumulated high levels of CYVaV. Level of CYVaV in individual leaves of a systemically infected plant was determined (FIG. 15, Panel C). Leaves 4 and 5 were agroinfiltrated with CYVaV. Note the substantial accumulation of CYVaV in the youngest leaves.

Symptoms of *N. benthamiana* systemically infected with CYVaV. Leaves 4 and 5 were agroinfiltrated with CYVaV. The first sign of a systemically infected plant is a "cupped" leaf (FIG. 16), which was nearly always leaf 9. In the following few weeks, leaf galls emerged at the apical meristem and each node of the plant. Systemically infected plants also had root galls containing a substantial amount of CYVaV as evidenced by Northern plant blot.

Figure 17:
FIG. 17 is an image of a tomato plant at 53 days post-infection (left) with a plant of the same age (right), and demonstrating the exceptional host range of CYVaV. Sap from a systemically-infected *N. benthamiana* plant was injected into the petiole of a tomato plant. One of four plants showed very strong symptoms and was positive for CYVaV by PCR analysis.

CYVaV demonstrates an exceptional host range. Sap from a systemically-infected *N. benthamiana* plant was injected into the petiole of tomato (FIG. 17). One of four plants showed very strong symptoms and was positive for CYVaV by PCR. Plant shown is at 53 days post-infection with a plant of the same age.

Figure 18:
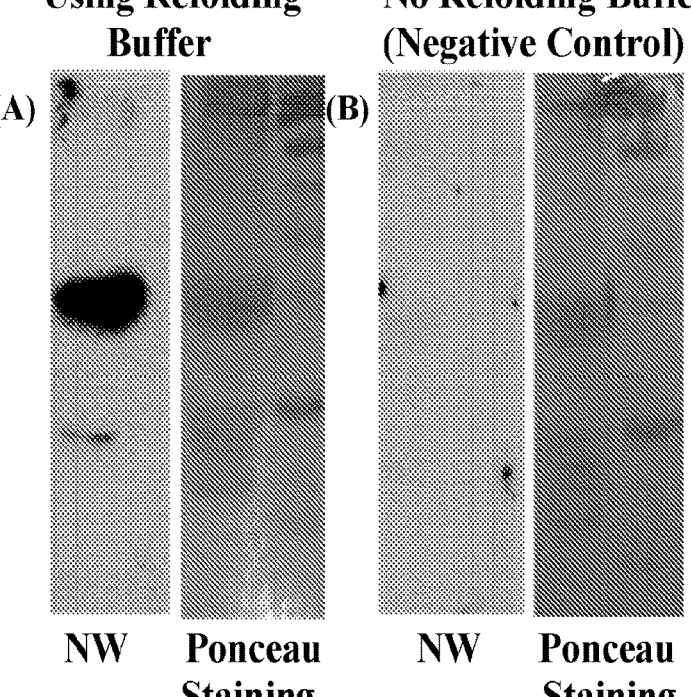
FIG. 18 demonstrates that CYVaV binds to a highly abundant protein extracted from the phloem of cucumber. Referring to Panel A, labeled full-length CYVaV bound to a prominent protein in this northwestern blot. Proteins were renatured after SDS gel electrophoresis. This protein is believed to be a known, highly conserved RNA binding protein containing an RRM motif that is known to chaperone RNAs from companion cells into sieve elements in the phloem of cucumber. Referring to Panel B, no binding was seen when the proteins remained denatured after electrophoresis.

CYVaV binds to a highly abundant protein extracted from the phloem of cucumber. Labelled full-length CYVaV binds to a prominent protein as demonstrated in the Northwestern blot (FIG. 18). Proteins were renatured after SDS gel electrophoresis. This protein is believed to be a known, highly conserved RNA binding protein containing an RRM motif known to chaperone RNAs from companion cells into sieve elements in the phloem of cucumber. No binding was seen when the proteins remained denatured after electrophoresis.

Figure 30:
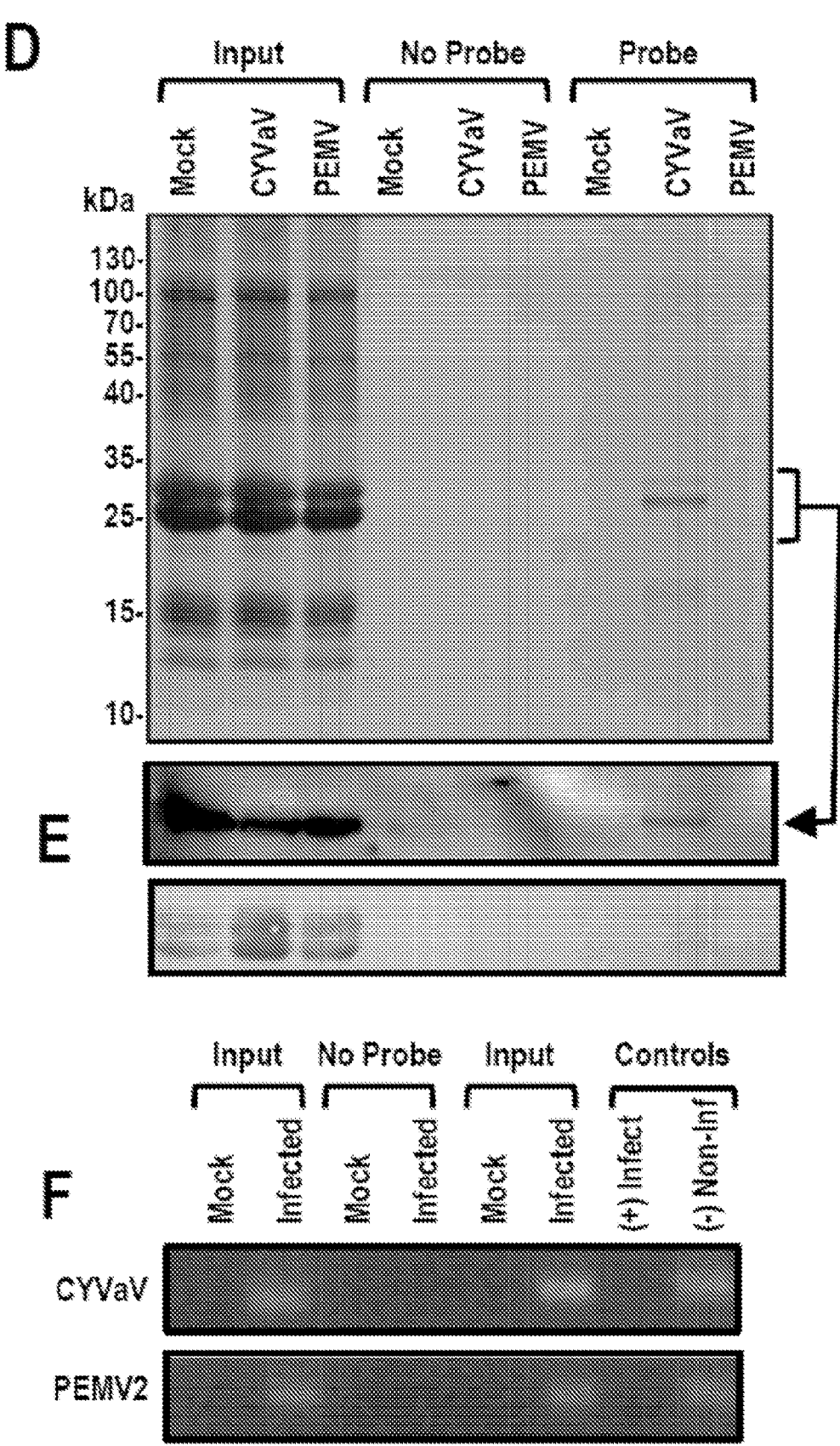
FIG. 30 illustrates CYVaV binding to phloem protein 2 (PP2) in cucumber and *N. benthamiana* phloem. Referring to Panel A, phloem exudates from uninfected (mock) and two CYVaV-infected cucumber (CYVaV 1 and 2) were collected, crosslinked with formaldehyde (Input) and then used for pull down assays using streptavidin beads with and without attached 5'-biotinylated CYVaV probes (Probe and No Probe, respectively). SDS PAGE gel was stained with Coomassie Blue. Referring to Panel B, samples from A were subjected to electrophoresis and then transferred to nitrocellulose membranes and analyzed by Western Blot using polyclonal antibody to cucumber PP2 (CsPP2) (upper panel). Panel B, lower panel, is the Ponceau S-stained membrane. Referring to Panel C, total RNA recovered from pulldown assay before RNase treatment was subjected to RT-PCR to verify the presence of CYVaV. (+), RNA from CYVaV-infected *N. benthamiana*; (–), RNA from an uninfected cucumber plant. Similar assays were conducted utilizing *N. benthamiana* infected with CYVaV or PEMV2 (Panels D, E and F). For PEMV2 pull down, PEMV2-specific probes were attached to beads.

Referring to FIG. 30, CYVaV binds to phloem protein 2 (PP2). Panels A, B and C relate to experiments involving a mock (uninfected) cucumber plant and two cucumber plants infected with CYVaV. In panel A, phloem exudates from the uninfected (mock) and two CYVaV-infected (CYVaV 1 and 2) plants were collected, crosslinked with formaldehyde (Input) and then used for pull down assays using streptavidin beads with and without attached 5'-biotinylated CYVaV probes (Probe and No Probe, respectively). SDS PAGE gel was stained with Coomassie Blue. As indicated in the three input lanes, an analysis of all proteins present in the sap includes significant amounts of protein with a molecular weight of about 25 kDa, which corresponds with the molecular weight of a common PP2. In the middle three lanes, essentially no proteins were found, indicating that PP2 does not bind to the streptavidin beads. In the right three lanes, a significant amounts of protein with a molecular weight of about 25 kDa was again found, indicating that PP2 was bound to CYVaV attached to the probe attached to the beads before being washed down from the beads. In panel B, samples from the right three lanes of A were subjected to electrophoresis and then transferred to nitrocellulose membranes and analyzed by Western Blot using polyclonal antibody to cucumber PP2 (CsPP2) (upper panel). Panel B, lower panel, is the Ponceau S-stained membrane. In panel C, total RNA recovered from the pull down assay before RNase treatment was subjected to RT-PCR to verify the presence of CYVaV. Additional controls were: (+), RNA from CYVaV-infected *N. benthamiana*; and (−), RNA from an uninfected cucumber plant. The assay indicates that CYVaV was bound to CsPP2 in the sap of the cucumber plant. FIG. 30, Panels D, E and F show a similar assay using *N. benthamiana* infected with CYVaV or PEMV2. For the PEMV2 pull down, PEMV2-specific probes were attached to beads. PEMV2 in this assay acts as a further control. The results indicate that CYVaV was bound to PP2 in the sap of the *N. benthamiana* plant by PEMV2 was not bound to PP2 in the sap of the *N. benthamiana* plant.

PP2 is believed to be involved with the movement or viroids but has not been reported to be involved in the coating or movement of any virus. Similarly, in the results described above. PP2 did not bind to PEMV2 in the sap of the plant. Without intending to be limited by theory, we believe that PP2 bound to CYVaV in the sap of a plant may also be responsible for the movement of CYVaV. While the early reports of CYVaV suggest that CYVaV does not move within a plant without a helper virus (CVEV) providing a movement protein, we have demonstrated that CYVaV moves systemically within a plant without a helper virus. However, a helper virus may still be required in nature for encapsidation to allow CYVaV to leave the phloem of a host plant and travel to another plant. In other experiments similar to the description above, CYVaV appears to bind to PP2 in the sap of tomato and melon plants. PP2 is found in essentially all plants and may allow iRNA-based vectors to move in, and systemically infect, a wide range of host plants.

Figure 19:
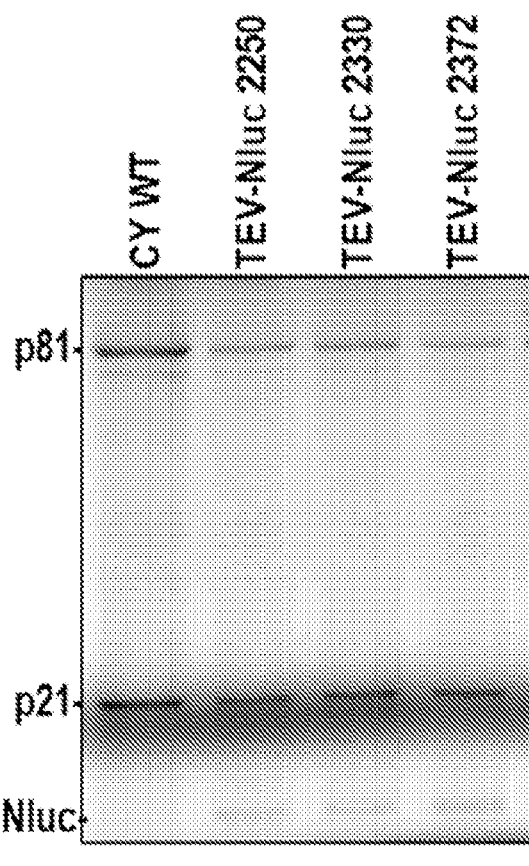
FIG. 19 demonstrates that CYVaV is capable of expressing an extra protein from its 3'UTR using a TEV IRES. The location of three separate inserts (in three separate constructs) of nanoluciferase downstream of the Tobacco etch virus (TEV) internal ribosome entry site (IRES) are shown (Panel A). In vitro translation was measured in wheat germ extracts for the three constructs (Panel B). Note the location of the nanoluciferase protein (Nluc) is near the bottom of the gel. Expression of nanoluciferase was measured in protoplasts in vivo (Panel C). Full-length RNA transcripts of the constructs (Panel A) were transformed into protoplasts: 18 hours later, total protein was extracted and nanoluciferase activity measured in a luminometer.

CYVaV can express an extra protein from its 3'UTR using a TEV IRES. Location of three separate inserts of nanoluciferase downstream of the Tobacco etch virus (TEV) internal ribosome entry site (IRES) were identified (FIG. 19). In vitro translation in wheat germ extracts of the three constructs was evaluated. Location of the nanoluciferase protein (Nluc) is near the bottom of the gel. Expression of nanoluciferase in protoplasts in vivo was investigated (FIG. 19, Panel C). Full-length RNA transcripts of the constructs shown in (A) were transformed into protoplasts. 18 hours later, total protein was extracted and nanoluciferase activity measured in a luminometer.

Figure 20:
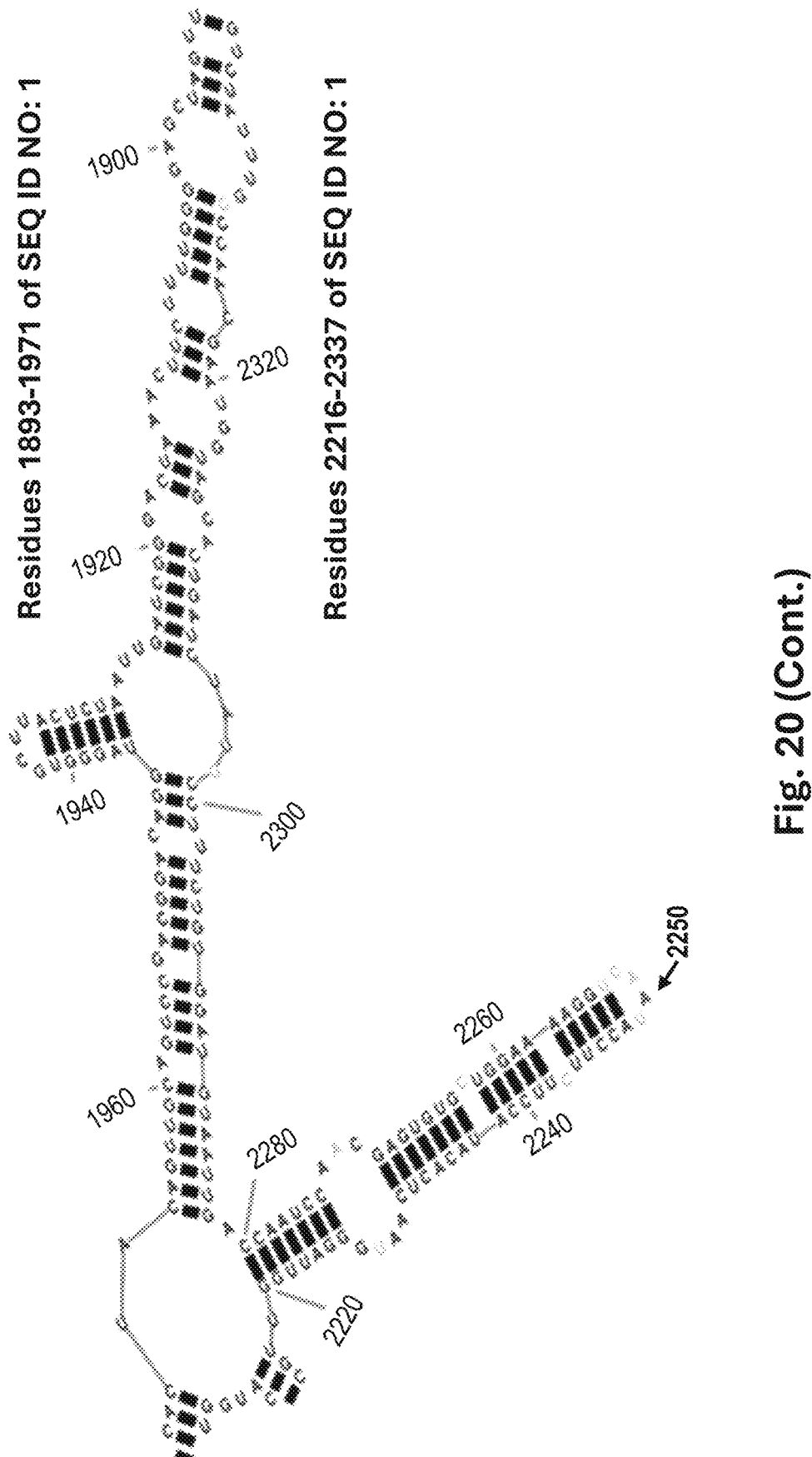
FIG. 20 illustrates a stable hairpin insert at position 2250. A schematic representation of CY2250sfPDS60 is shown in Panel A. The location of the insert in the secondary structure of CYVaV is shown in Panel B, which location corresponds to a region for accommodating inserted hairpins, such as shown by double line box in FIG. 9. Data from wheat germ extract in-vitro translation assay of T7 transcripts from CYVaV-wt, and CYVaV VIGS vectors containing different amounts of sequence at position 2250) are shown in Panel C. For example, construct sfPDS60 demonstrated excellent systemic movement in plants. Northern blot analysis of total RNA isolated from *A. thaliana* protoplasts infected by CYVaV wt and CYVaV VIGS vectors. CYVaV-GDD negative control is shown in Panel D. (+) represents plus-strands and (−) are minus strand replication intermediates. An image of *N. benthamiana* infected by CY2250sfPDS60 is shown in Panel E. RT-PCR products from local leaf and systemic leaf are shown in Panel F. The primer set amplify positions 1963-2654 in the 3' region of CYVaV. The sequence of the insertion region (underlined) of the vector collected from systemic leaf is shown in Panel G, with dashed line boxed sequences on either side of the insert forming the stem of the hairpin.
Figure 20:
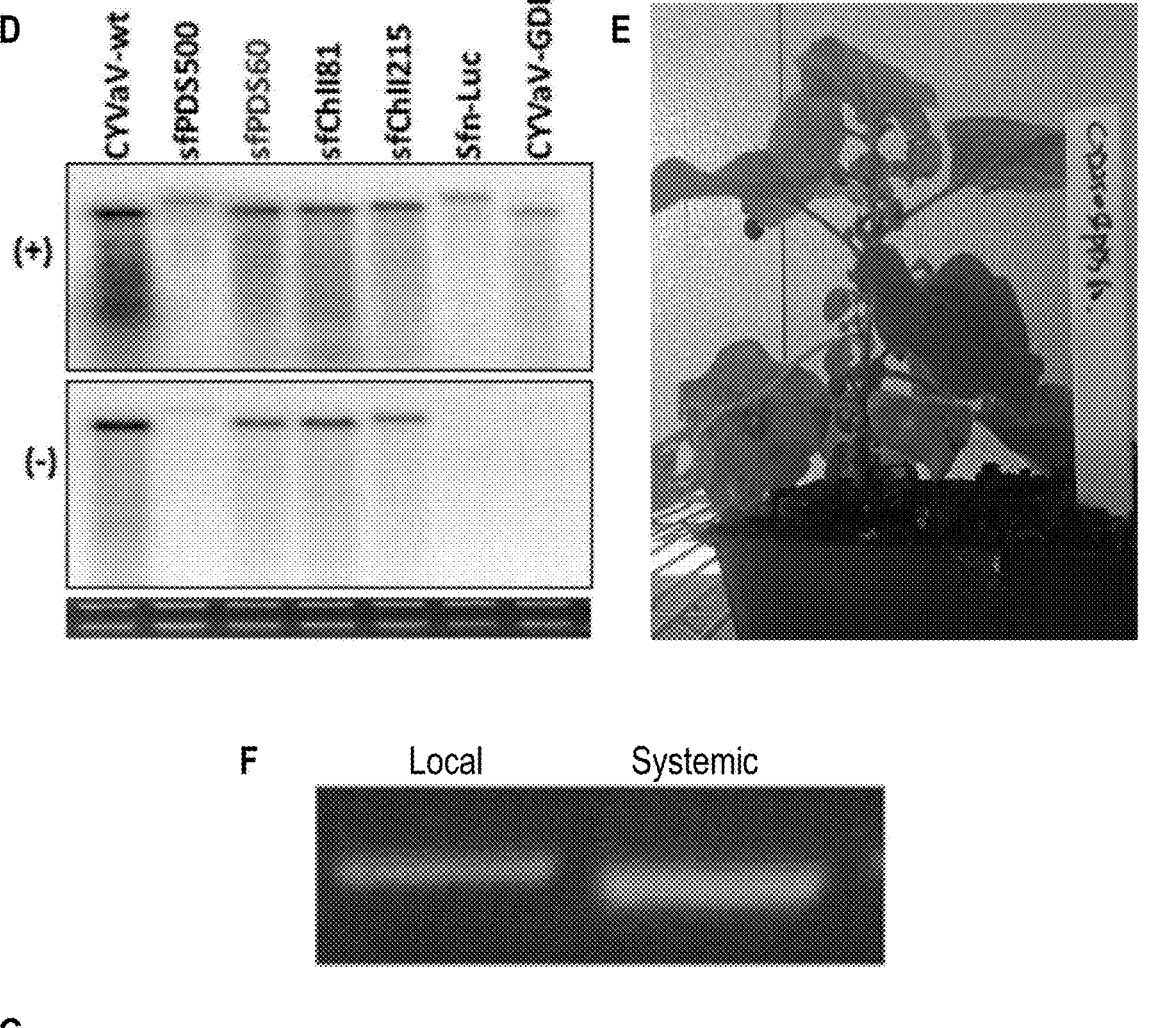
Figure 21:
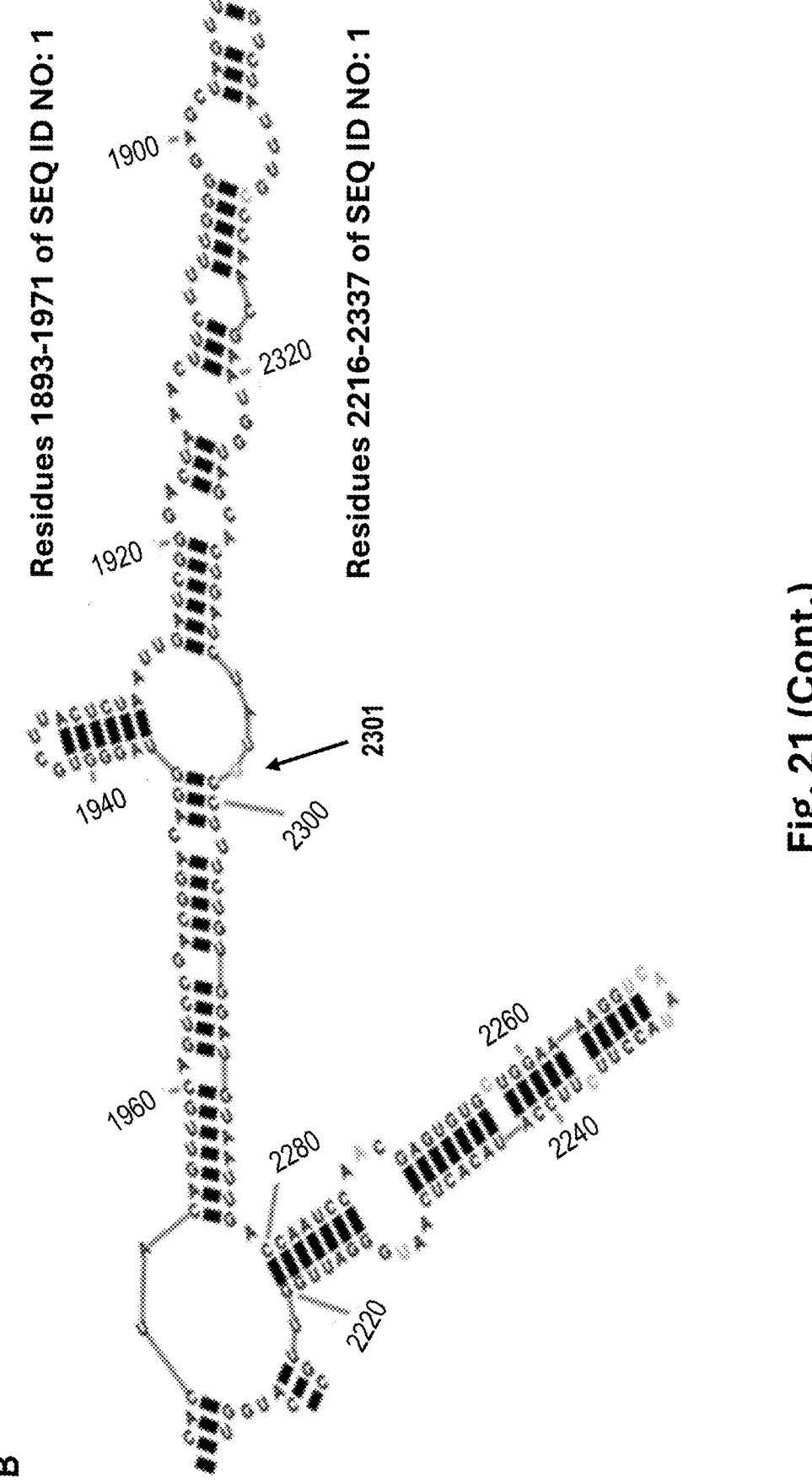
FIG. 21 illustrates a stable hairpin insert at position 2301. A schematic representation of CY2301sfPDS60 is shown in Panel A. The location of the insert in the secondary structure of CYVaV is shown in Panel B, and corresponds to a region for accommodating inserted hairpins, such as shown by double line box in FIG. 9. Data from wheat germ extract in-vitro translation assay of T7 transcripts from CYVaV-wt, and CYVaV VIGS vectors containing different amounts of sequence at positions 2301 and 2319 are shown in Panel C. For example, construct PDS60 demonstrated excellent systemic movement in plants. Northern blot analysis of total RNA isolated from *A. thaliana* protoplasts infected by CYVaV wt and CYVaV VIGS vectors. CYVaV-GDD and negative control. is shown in Panel D. (+) represents plusstrands and (−) are minus strand replication intermediates. An image of *N. benthamiana* infected by CY2301sfPDS60 is show in Panel E. RT-PCR products from local leaf and systemic leaf are shown in Panel F. The primer set amplify positions 1963-2654 in the 3' region of CYVaV. The sequence of the insertion region of the virus vector collected from systemic leaf is shown in Panel G, with dashed line boxed sequences forming the stem of the hairpin.
Figure 21:
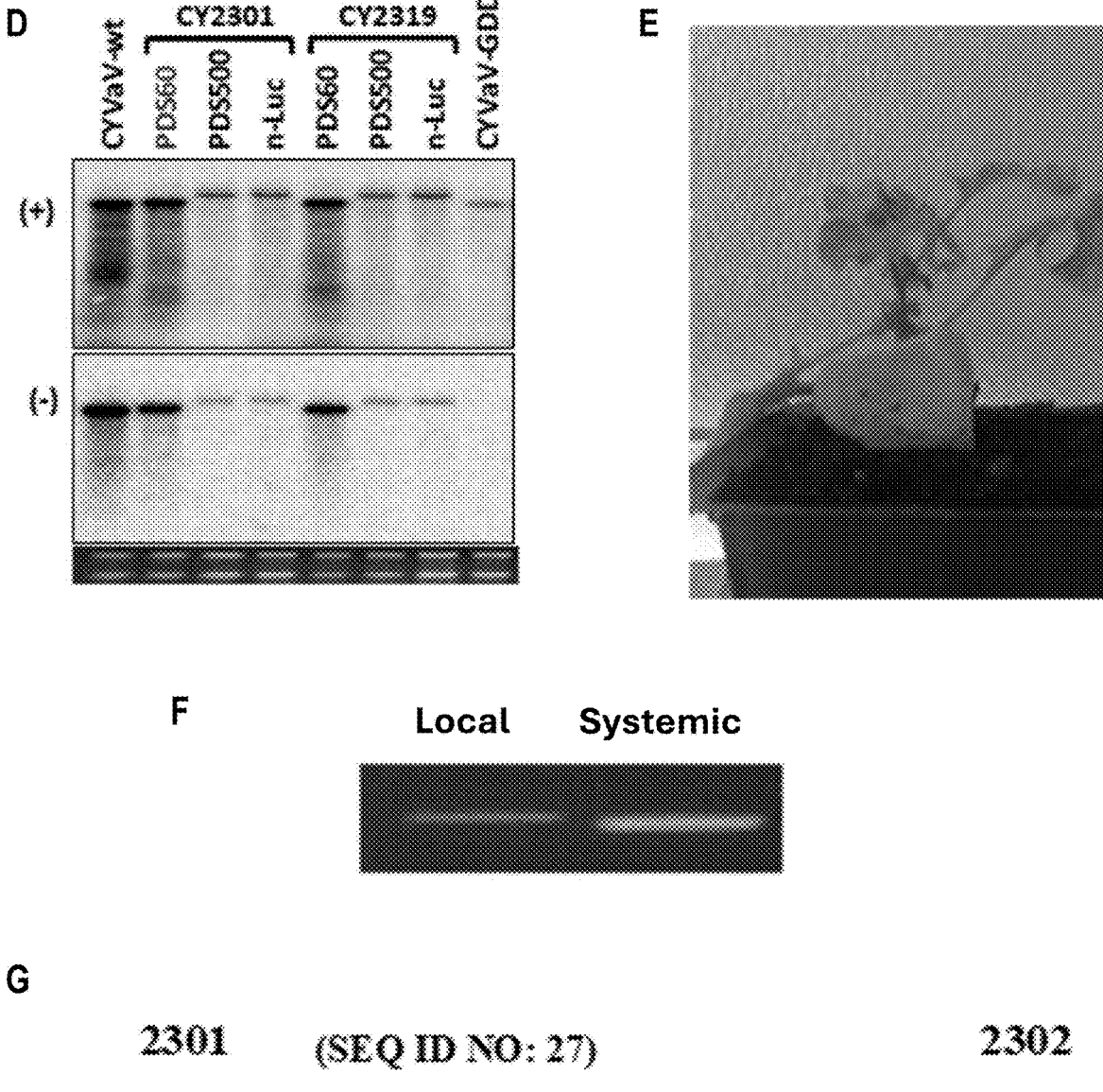
Figure 22:
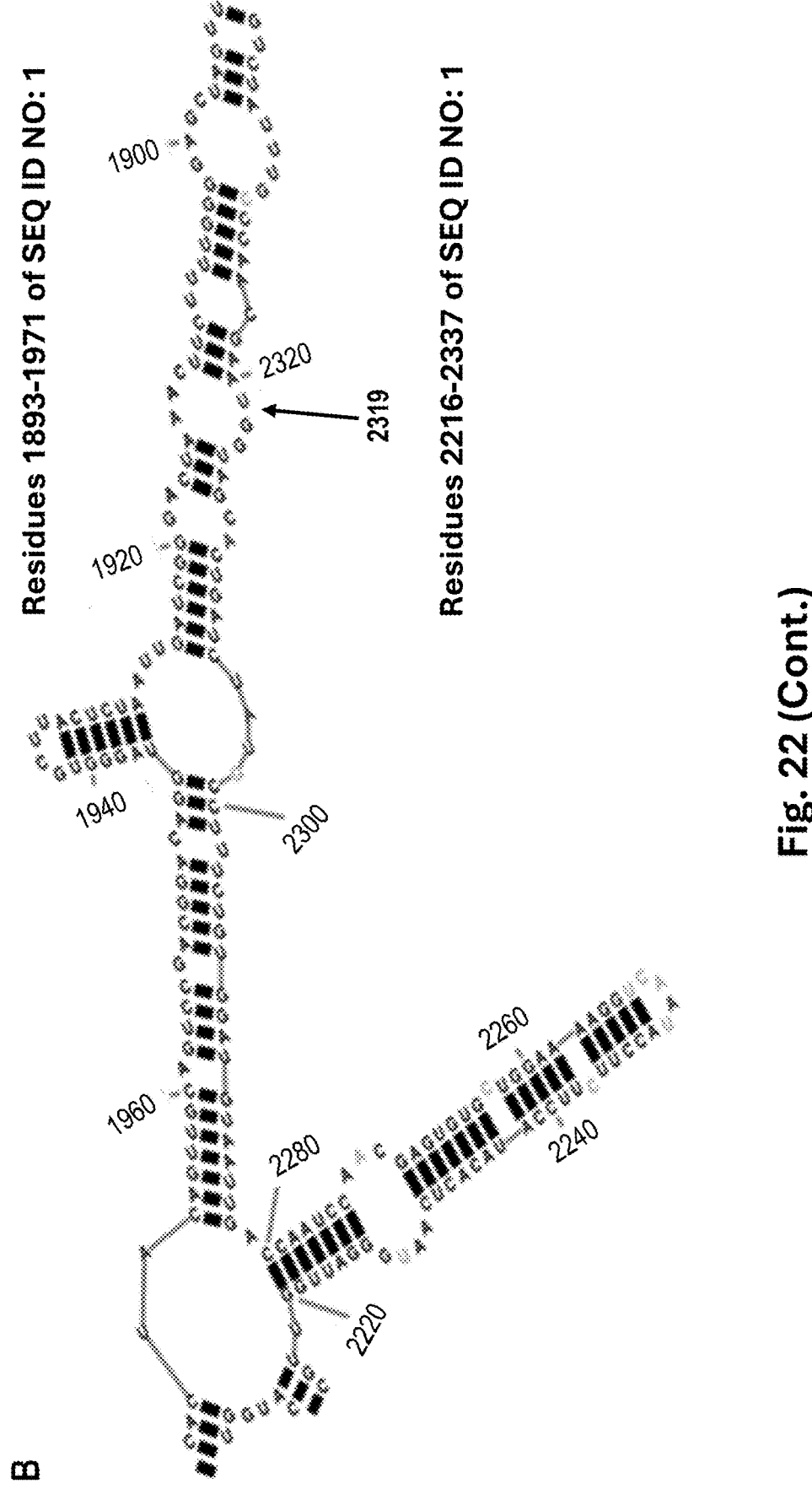
FIG. 22 illustrates a stable hairpin insert at position 2319. A schematic representation of CY2319sfPDS60 is shown in Panel A. The location of the insert in the secondary structure of CYVaV is shown in Panel B, and corresponds to the region for accommodating inserted hairpins shown by double line box in FIG. 9. Data from wheat germ extract in-vitro translation assay of T7 transcripts from CYVaV-wt, and CYVaV VIGS vectors containing different amounts of sequence at position 2301 and 2319 are shown in FIG. 21, Panel C. Northern blot analysis of total RNA isolated from *A. thaliana* protoplasts infected by CYVaV wt and CYVaV VIGS vectors. CYVaV-GDD and negative control is also shown in FIG. 21, Panel D. An image of *N. benthamiana* infected by CY2319sfPDS60 is shown in Panel C. RT-PCR products from local leaf and systemic leaf is shown in Panel D. The primer set amplify positions 1963-2654 in the 3' region of CYVaV.
Figure 23:
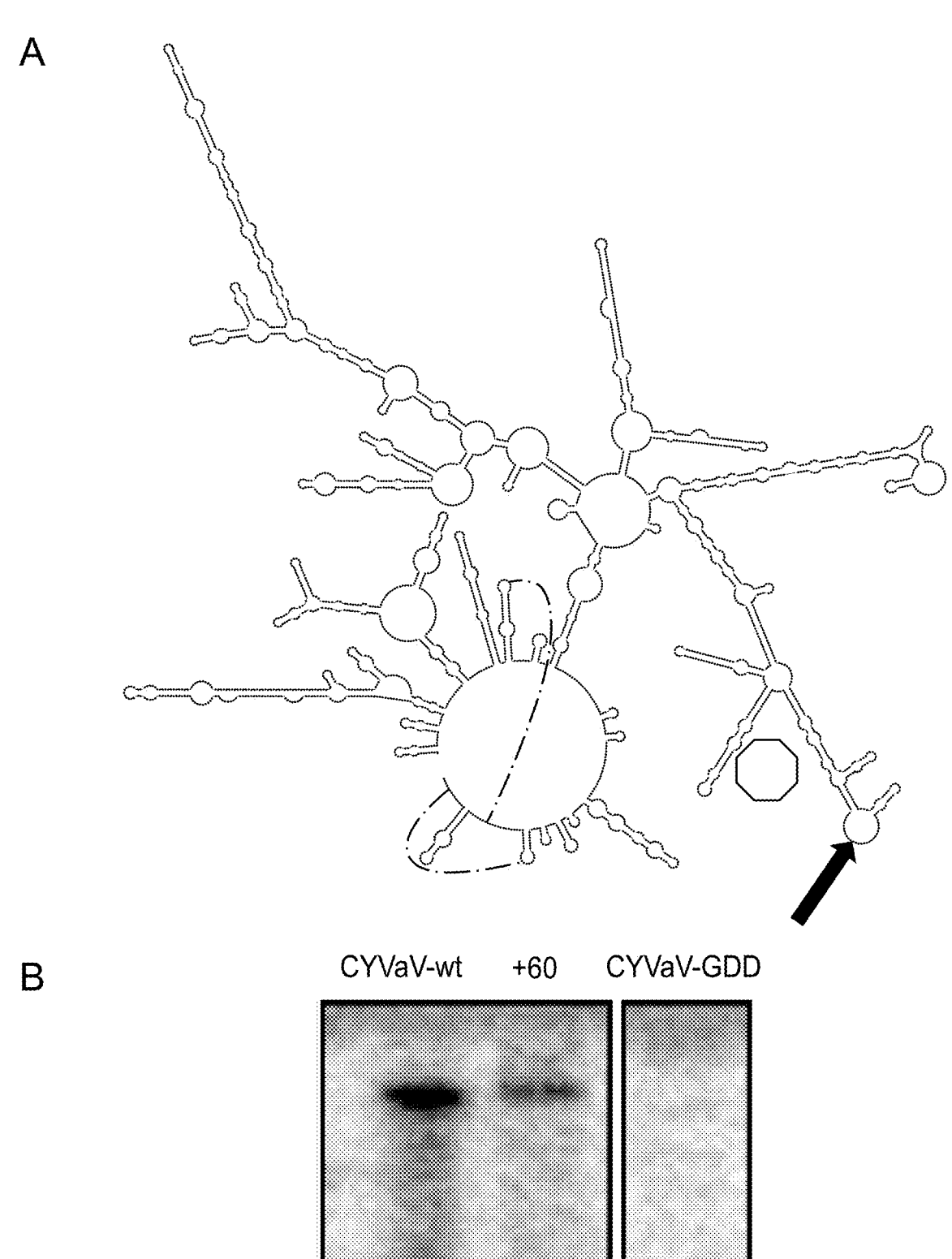
FIG. 23 illustrates the location of a 60 nt insertion (non-hairpin) onto the ORF of the RdRp of CYVaV (Panel A). The location of the insert is indicated by the black arrow. A stop codon, indicated by the black hexagon, was engineered just upstream of the insert to truncate the RdRp. Northern blot of plus-strand RNA levels in *Arabidopsis* protoplasts is shown in Panel B. CYVaV-GDD is a nonreplicating control.

Exemplary locations for stable hairpin inserts at positions 2250, 2301 and 2319 were evaluated. The location for each of the inserts falls within an exemplary region noted above (see FIG. 9). Wheat germ extract in-vitro translation assay of T7 transcripts from CYVaV-wt, and CYVaV VIGS vectors containing different amounts of sequence at position 2250 was conducted (FIG. 20). For example, construct sfPDS60 demonstrated excellent systemic movement in plants. Wheat germ extract in-vitro translation assay of T7 transcripts from CYVaV-wt, and CYVaV VIGS vectors containing different amounts of sequence at positions 2301 and 2319 was conducted (FIG. 21). Northern blot analysis of total RNA isolated from *A. thaliana* protoplasts infected by CYVaV wt and CYVaV VIGS vectors. CYVaV-GDD and negative control was conducted (FIG. 20, Panel D). Northern blot analysis of total RNA isolated from *A. thaliana* protoplasts infected by CYVaV wt and CYVaV VIGS vectors. CYVaV-GDD and negative control. was conducted (FIG. 21, Panel D). Constructs CY2250sfPDS60, CY2301PDS60, CY2301sfPDS60, CY2319sfPDS60 (including inserts at positions 2250, 2301, 2319, respectively) all demonstrated excellent systemic movement with insertion. In addition, constructs CY2331PDS60 (including inserts at position 2331) also demonstrated the ability to move systemically throughout the host. A further construct, CY2083TAAPDS60, includes an insert at position 2083, which location is in the RdRp ORF (preceded by an inserted stop codon).

The sequences of the insertion regions (underlined below and as shown in FIG. 20, Panel G, and FIG. 21, Panel G) of the vector collected from systemic leaf is presented below:

```
                                    (SEQ ID NO: 26)
taggcctcgacacgggaaggtagctgtcccggcactgggttgcacatat
tccgtgccgacgccac
```

```
                                    (SEQ ID NO: 27)
ccggcctcgacacgggaaggtagctattccgtgccgacgccgt
``` iRNA-Based Vector Platform

In one embodiment, an iRNA-based vector is provided for treating disease in the citrus industry caused by CLas bacteria (HLB). An isolate of CYVaV is utilized as a vector to target both the bacteria and the psyllid insects that deliver the bacteria into the trees. As discussed above, CYVaV is limited to the phloem where it replicates and accumulates to extremely high levels comparable to the best plant viruses. In addition, its relatively small size makes it exceptionally easy to genetically engineer. Thus, consideration of the structure and biology of CYVaV aided in the development of this novel infectious agent as a vector and model system for phloem transit.

The structure of the 3′UTR of CYVaV was determined based on SHAPE RNA structure mapping (FIG. 9). In addition, a number of replication and translation elements were identified based on biochemical assays, as well as phylogenetic conservation (with umbraviruses) of their sequence and/or structure and position (FIG. 19, Panel A). An I-shaped element was also identified that serves as a cap-independent translation enhancer (3′CITE). A series of long-distance kissing-loop interactions (double arrows) were also identified, which are believed to be involved in stabilizing the RNA and accumulation in the absence of a silencing suppressor. Based on this structure, a number of areas were identified as suitable locations for sequence insertion, which should not disturb the surrounding structure.

Certain sites have been identified for potential inserts in the 3′ UTR and the RdRp ORF that can accommodate RNA hairpins, e.g., for generation of siRNAs that target feeding insects, sites that accommodate reporter ORFs and still allow for replication of an engineered CYVaV in agro-infiltrated *N. benthamiana*, and sites that trigger high level translation of reporter proteins in vitro. An engineered CYVaV incorporating the added ORF and siRNAs is introduced into a storage host tree, and then pieces thereof are usable for straight-forward introduction into field trees by grafting. Given the rarity of CYVaV (to date, it has only been identified in the four limequat trees by Weathers in the 1950s), there is little risk of superinfection exclusion.

Various insert locations were identified wherein replication or translation properties of the vector were not significantly reduced or eliminated. Insert locations adversely affecting such properties (likely due to disrupting the RNA structure or other important aspect of the CYVaV vector) were not pursued further. Four exemplary insert locations on the CYVaV-based vector were identified at positions 2250, 2301, 2319 and 2331. Alternatively or additionally, inserts may be located at positions 2330, 2336 and/or 2375. 50 nt hairpin inserts were successfully deployed in these locations with no disruption to translation in vitro or replication in protoplasts and CYVaV was able to move systemically in *N. benthamiana*.

Although CYVaV has no additional ORFs, both genomic (g)RNA and a subgenomic (sg)RNA of about 500 nt are detectable using probes to plus- and minus-strands. Investigation of the region that should contain an sgRNA promoter revealed an element with significant similarity to the highly conserved sgRNA promoter of umbraviruses and to a minimal but highly functional sgRNA promoter of carmovirus TCV. In addition, similar RNAs that also only express the RdRp and are related to Tombusviruses all generate a similar sized subgenomic RNA, and may simplify expression of peptides and proteins.

In order to determine where inserts are tolerated downstream of the sgRNA promoter in CYVaV, an evaluation of where critical elements exist in the 3′ UTR of CYVaV was conducted, so that such elements are avoided when inserting heterologous sequences. As described about, the 3′ CITE for CYVaV was identified, as well as several additional 3′ proximal hairpins that are highly conserved in umbraviruses and known to be critical for replication and translation. Using deletions/point mutations, the sequence downstream of the putative sgRNA promoter and upstream of the CAS (~120 nt) was investigated for regions that do not impact either accumulation in protoplasts or systemic movement in *N. benthamiana*. A similar strategy was previously utilized by the present inventors to identify regions in the 3′ UTR of TCV that can accommodate hairpins targeted by RNase III-type enzymes (Aguado, L. C. et al. (2017). *RNase III nucleases from diverse kingdoms serve as antiviral effectors*. Nature 547:114-117).

After identifying suitable regions for accommodating deletions/mutations (e.g., regions not involved in critical functions), heterologous sequences of different lengths were inserted therein to evaluate CYVaV functionality with an extended 3′ UTR. Such investigation aids in determining maximal insert length to ensure that such insert will be tolerated by the CYVaV-based vector while still accumulating to robust levels and engaging in systemic movement. It is believed that the CYVaV-based vector may be able to accommodate an insert having a size of up to 2 kb. In this regard, the nearest related viruses (papaya umbra-like viruses, which like CYVaV, only encode a replicase-associated protein and the RdRp) are 1 to 2 kb larger, with all of the additional sequence length expanding their 3' UTRs (Quito-Avila, D. F. et al. (2015). Detection and partial genome sequence of a new umbra-like virus of papaya discovered in Ecuador. Eur J Plant Pathol 143:199-204). Various size sequence fragments were evaluated, beginning at 50 nt (the size of an inserted hairpin for small RNA production), up to about 600 nt (the size of an enzybiotic ORF). Initial small RNA fragments include a reporter for knock down of phytoene desaturase, which turns tissue white. The longer size fragments include nano luciferase and GFP ORFs, which may also be used as reporters for examining expression level. Inserts are made in constructs containing the wild-type (WT) sgRNA promoter and the enhanced sgRNA promoter.

Figure 24:
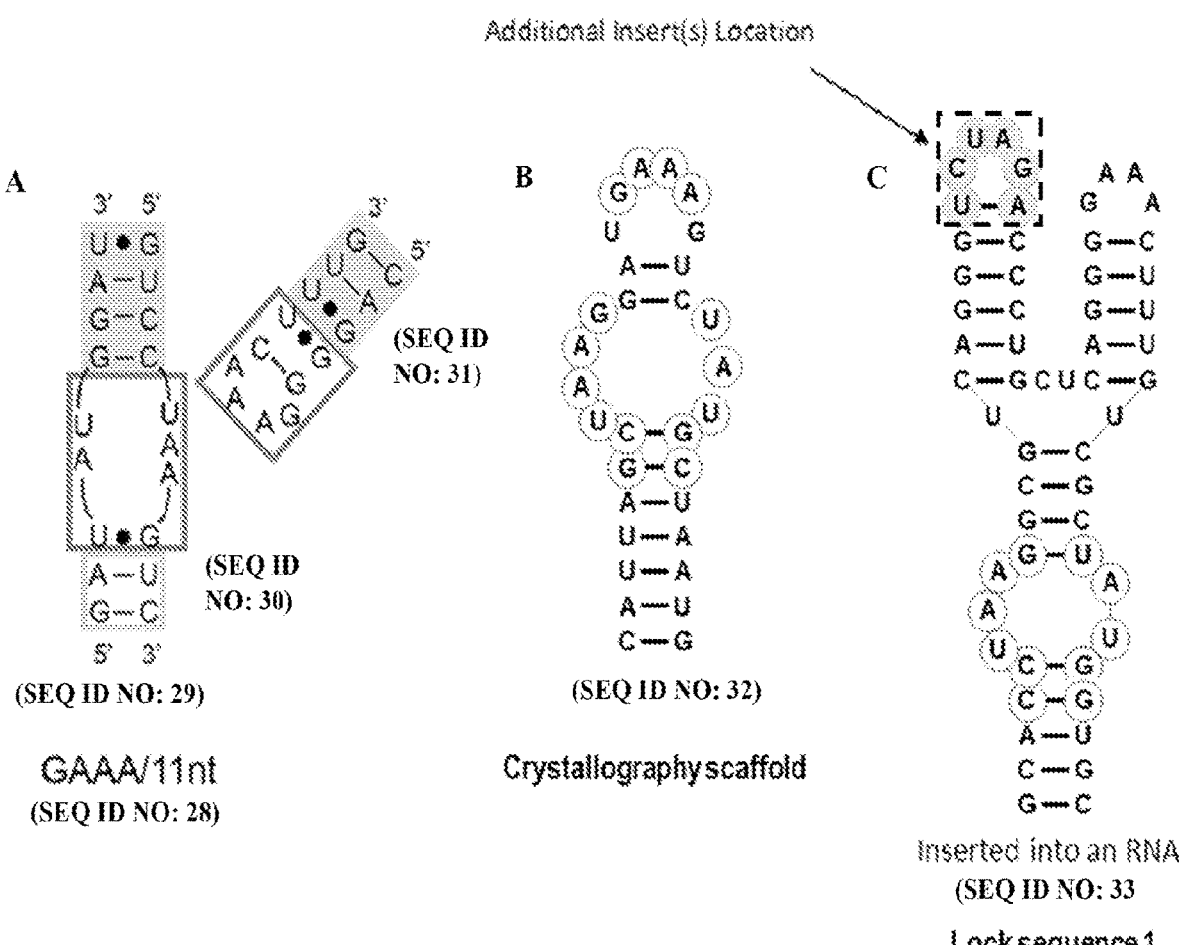
FIG. 24 illustrates a lock and dock sequence for stabilizing the base of inserts. Referring to Panel A, tetraloop GNRA (GAAA) docking with its docking sequence generates an extremely stable structure, and represents a basic lock and dock sequence. Referring to Panel B, use of a scaffold consisting of a docked tetraloop (analogous to the similar structure sometimes used as a crystallography scaffold) is shown. Referring to Panel C, a unique lock and dock structure is shown. Inserts (hairpins or non-hairpin sequences) may be added to the restriction site (as identified by dashed line box). Circled bases in the sequences are the docking sequences for the GAAA tetraloop.

Lock and Dock Sequence for stabilizing the base of inserts. Referring to FIG. 24, Panel A, the basic structure of the lock and dock sequence is shown. Tetraloop GNRA sequence (e.g., GAAA) docking with its docking sequence generates an extremely stable structure. Sequences shown in FIG. 24, Panel A, are presented below:

(SEQ ID NO: 28)
gaaa (SEQ ID NO: 29)
gauauggau (SEQ ID NO: 30)
guccuaaguc (SEQ ID NO: 31)
caggggaaacuuug The use of a scaffold comprising a docked tetraloop as a crystallography scaffold is provided (FIG. 24, Panel B). The sequence shown in FIG. 24, Panel B, is presented below:

(SEQ ID NO: 32)
cauuagcuaaggaugaaagucuaugcuaaug

A lock and dock structure in accordance with disclosed embodiments is shown in FIG. 24, Panel C. Inserts (hairpins or non-hairpin sequences) may be added to the restriction site at the identified additional insert location. Circled bases are docking sequences for the tetraloop. The sequence shown in FIG. 24, Panel C, is presented below:

(SEQ ID NO: 33)
gcaccuaaggcgucagggucuagacccugcucaggggaaacuuugucgc
uauggugc

Figure 31:
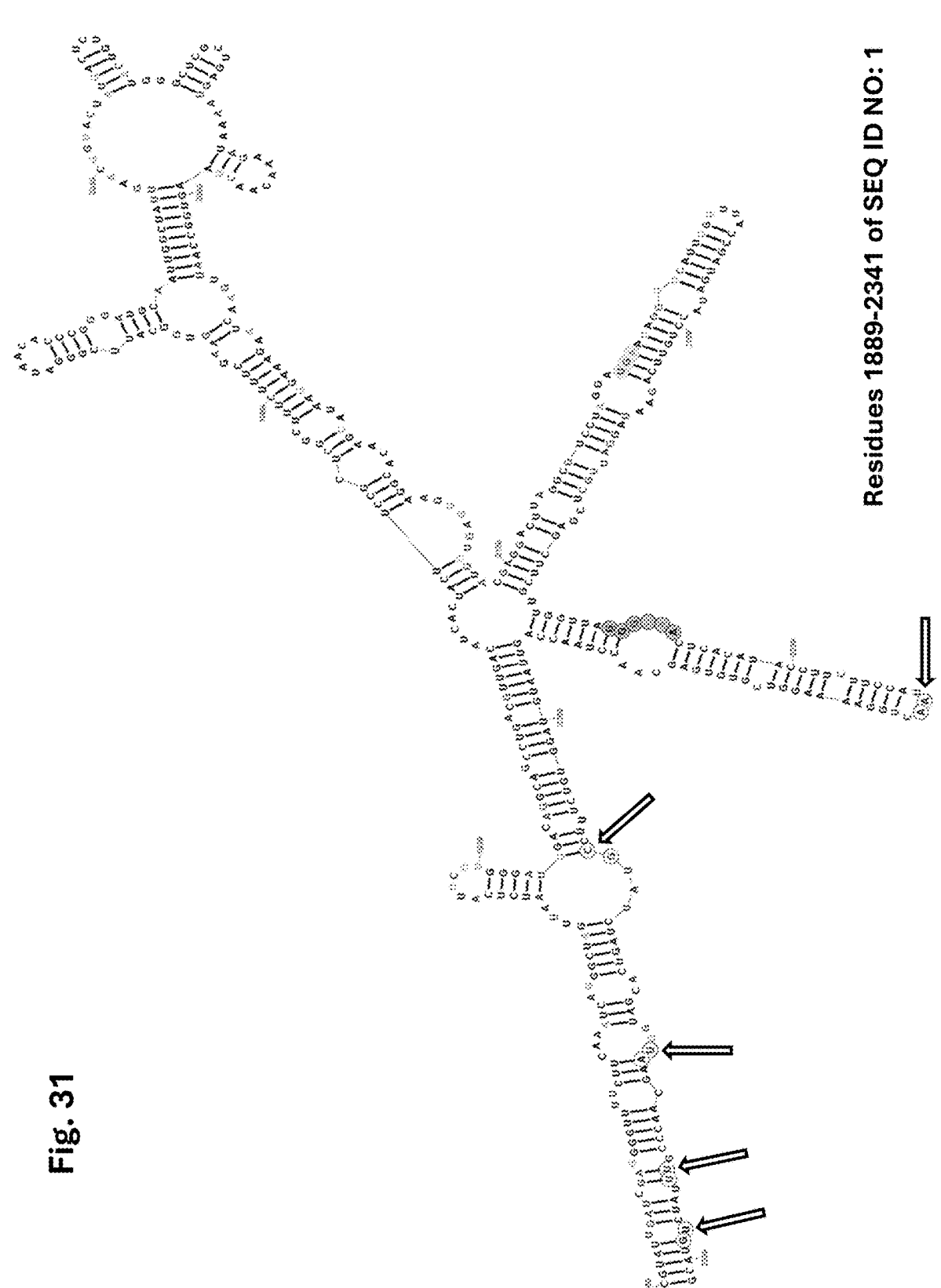
FIG. 31 illustrates shows the structure and sequence of CYVaV from position numbers 1889-2341. Potential insert positions at 2250, 2301, 2319, 2330 and 2336 are shown, each with an adjacent pair of bases in a light blue circle. The structures and sequences of lock and dock 1 and lock and dock 2 (FIG. 29), and/or another lock and dock structure in accordance with the present disclosure, may be inserted, e.g., at any of the five positions 2250, 2301, 2319, 2330 and/or 2336 (identified by arrows).

Lock and dock elements can be inserted into iRNA to stabilize the resulting vector despite the presence of hairpins or other inserts. FIG. 29 shows additional examples of lock and dock structures. Each of the two lock and dock structures shown, L&D1 (SEQ ID NO:42) and L&D2 (SEQ ID NO:43), were separately inserted into position 2301 in CYVaV to make two examples of CYVaV based vectors, one having L&D1 and the other having L&D2. The sequences shown in FIG. 29, Panel A, are presented below:

(SEQ ID NO: 42)
gcgauauggauucagggacuagucccugcucaggggaaacuuuguguccuaagucgc (SEQ ID NO: 43)
gcgauauggaucaggacuaguccugucacccucacuucgguguccagggaaacuuugugggugaguccuaagucgc Replication, movement and stability of both of the CYVaV based vectors, each with a lock and dock structure, was demonstrated by systemically infecting *N. benthamiana* plants CYVaV-L&D1 and CYVaV-L&D2. In other examples, L&D1 or L&D2 may be inserted at position 2250, 2319, 2330, 2336 and 2375 (see FIG. 31).

The term "lock and dock" is used to indicate that the structure has a highly stable locked or lockable portion and a docking portion suitable for the addition of one or more inserts. In the examples shown, the highly stable portion is provided by way of a tetraloop GNRA sequence (wherein N is A, C, G, or U: R is A or G), e.g., GAAA, and a tetraloop dock sequence (alternatively called a tetraloop lock sequence). In use, the structure folds with the tetraloop GNRA becoming associated (though not bonded in the sense of forming Watson-Crick pairs) with the tetraloop dock sequence to generate an extremely stable structure, called the "lock". The "dock", represented in the Figure by the fragment insert side or a portion of the lock and dock including the fragment insert site, is separated from the iRNA backbone by the lock. One or more inserts added to the dock are inhibited from interfering with folding of the iRNA backbone by the lock. Inserts (hairpins or non-hairpin sequences) may be added to the fragment insert site. In other examples, the two-way stem shown is replaced with a three-way stem to provide a lock and dock structure having a lock and two docks. The examples shown include a dividing (e.g. two-way or three-way) stem, the base and one arm of which are within a tetraloop or other locking structure, and another arm of the dividing stem having an insert site.

In addition to particular iRNA constructs, the disclosed scaffolds and lock and dock structures may be utilized for attaching a heterologous segment(s) to and/or stabilizing any RNA vector, including plant or animal vectors. An RNA-based vector may be modified via the addition of one or more lock and dock structures, such as a tetraloop GNRA docking structure. Optionally, a parental or wild-type RNA molecule suitable for use as a vector may be modified by truncating a sequence non-specific hairpin located at a particular position. Generally, the hairpin is truncated by removing an upper or distal portion of the hairpin; however, a lower portion of the hairpin (e.g., 3-5 base pairs proximate to the main structure of the RNA molecule) is retained in the truncated hairpin. The resulting truncated hairpin forms or defines an insertion site. In some embodiments an insert, which may include a scaffold such as a lock and dock structure (e.g., a tetraloop sequence), is then attached to the insertion site. The lock and dock structure may comprise a heterologous segment(s), which is thereby attached to the modified RNA molecule. In some embodiments and at particular positions, a heterologous segment(s) may be attached directly to the insertion site of the truncated hairpin and without a lock and dock or other scaffold structure intermediate the insertion site and the heterologous segment(s).

In one example, a 30 base non-hairpin sequence was inserted into L&D1, which was in turn inserted into position 2301 in CYVaV to make a CYVaV based vector. The CYVaV vector was agroinfiltrated into an *N. benthamiana* plant and achieved systemic movement in the plant.

Figure 25:
FIG. 25 illustrates that stabilizing the local 3'UTR structure is highly detrimental, but insertion of a destabilizing insert nearby restores viability. Referring to Panel A, a schematic representation of CYVaV-wt. CYVaV-wt 3'stb is the parental stabilized construct containing 6 nt changes converting G:U pairs to G:C pairs. Two insertions of 60 nucleotides were added to the stabilized parental construct at positions 2319 and 2330 forming CY2319PDS60_3'stb and CY2330PDS60_3'stb. Nucleotide changes made to stabilize the structure and generate CYVaV-wt 3'stb are circled in Panel B. Insertion sites are indicated by the arrows for each constructs: left arrow in Panel A indicting insertion site for construct CY2319PDS60_3 stb; right arrow in Panel A indicating insertion site for construct CY2330PDS60_3'stb. Referring to Panel C, data is shown from wheat germ extract in-vitro translation assay of T7 transcripts from the constructs shown in Panel A. Note that p81 levels (the frameshift product) is strongly affected by stabilizing this region. Referring to Panel D, northern blot analysis of total RNA isolated from *A. thaliana* protoplast infected by CYVaV-wt, CYVaV-wt 3'stb, CY2319PDS60_3'stb, CY2330PDS60_3'stb, and CYVaV-GDD (non-replicating control) is shown. (+) represents plus-strands and (–) are minus strand replication intermediates.

Stabilizing the local 3'UTR structure is detrimental; however insertion of a destabilizing insert nearby restores viability. Referring to FIG. 25, Panel A, a representation of CYVaV-wt is shown. CYVaV-wt 3'stb is the parental stabilized construct containing 6 nt changes converting G:U pairs to G:C pairs. Two insertions of 60 nucleotides were added to the stabilized parental construct at positions 2319 and 2330 forming CY2319PDS60_3'stb and CY2330PDS60_3'stb. Nucleotide changes made to stabilize the structure and generate CYVaV-wt 3'stb are circled in Panel B. The sequences shown in FIG. 25, Panel B, is presented below:

```
                                   (SEQ ID NO: 34)
ggcuaguuaaucucauucgugggauggacaggcagccugacguugac (SEQ ID NO: 35)
guuaauguaggugucuuuccguaucuagu
(unmodified G:U pairs)

(SEQ ID NO: 36)
gucaacgcaggugccuguccguaucuagcc
(converted G:C pairs)
```

Targets for Treatment and Management

An anti-biotic insert for delivery by the disclosed vector is provided, which comprises either an enzybiotic or small peptide engineered to destroy the CLas bacterium. Enzybiotics prefer sugar rich, room temperature environments such as found in the plant phloem. The enzybiotic is translated in companion cells during the engineered CYVaV infection cycle. Proteins produced in the cytoplasm of the phloem are naturally able to exit into the sieve element (the default pathway for translated proteins), where CLas and other plant pathogenic bacteria take up residence. In the sieve element, the enzyme molecules move with the photo-assimilate up and down the trunk and lyse any bacteria upon contact. Since enzybiotics are targeted towards a specific class of bacteria, they preferably do not disturb the microbiome of the host tree. Various agents that target CLas have been developed (e.g., Hailing Jin, University of California, Riverside, CA). Thus, numerous inserts that target CLas bacterium are known in the art and may be utilized with the CYVaV vectors of the present disclosure.

As a further embodiment, it can be beneficial to target multiple pathways for destroying the disease and the disease psyllid vector. As a result, in certain embodiments the disclosed vectors include the enzy biotic and/or peptides described above, as well as inserts that trigger the production of siRNAs that interfere with either gene expression of the tree or the disease-carrying psyllid. In the case of the ACP, the RNA could kill the vector or render it wingless and thus harmless.

iRNA-Based Vector Targeting Host Gene Expression

Figure 27:
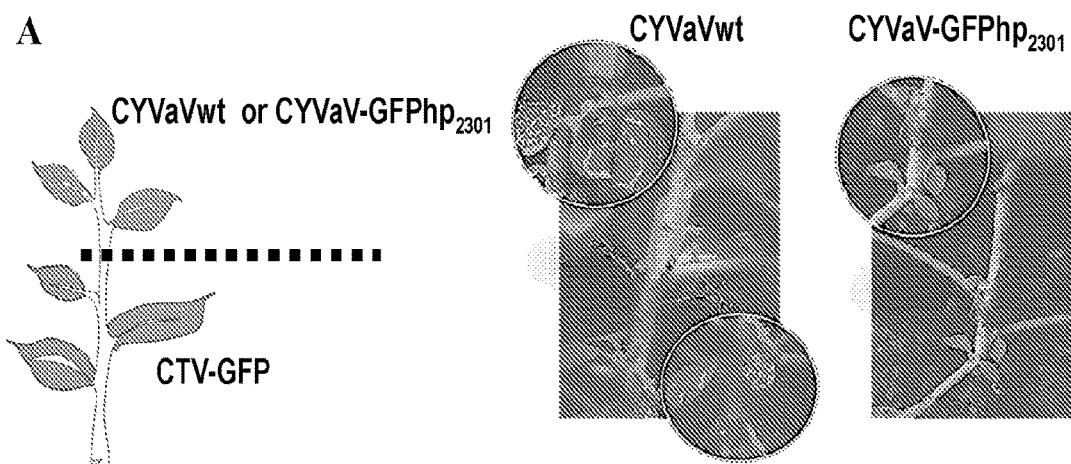
FIG. 27 illustrates a CYVaV VIGS vector that targets CTV. *N. benthamiana* infected with CTV-GFP (CTV expressing GFP) was used as root stock grafted to wild-type CYVaV (CYVaVwt) or CYVaV-GFPhp$_{2301}$ scions (Panel A). A hairpin targeting GFP (Panel B) is inserted in construct CYVaV-GFPhp$_{2301}$. The CYVaVwt scion had no effect on CTV-GFP infecting newly emerging rootstock leaves (Panel A, center image). However, green flecks were absent in stipules when CYVaV-GFPhp$_{2301}$ was present in the scion (Panel A, right image), demonstrating that movement of CYVaV-GFPhp$_{2301}$ down into the root stock inhibited progression of the CTV infection. When CYVaVwt was present in the root stock, new leaves from the CTV-GFP scion fluoresced green under UV light, demonstrating that widespread CTV infection was continuing unabated (Panel C, middle image). When CYVaV-GFPhp$_{2301}$ was in the root stock, the upper leaves in all CTV-GFP-infected scions were either partially or nearly fully absent of GFP flecks (Panel C, right image). RT-PCR of the red region (Panel C, right image, circled A) and green region (circled B) in the leaves absent of GFP flecks indicated that high levels of CYVaV-GFPhp$_{2301}$ correlated with red fluorescence (region A), with such tissue having between 3,000-fold and 440,000-fold less CTV compared to green region (region B), as shown graphically in Panel D. Fully infected *N. benthamiana* were agroinfiltrated with CYVaV carrying a hairpin that targeted a conserved sequence in the CTV genome (Panel F). After four days, CTV levels were about 10-fold lower in the infiltrated tissue as compared with tissue infiltrated with CYVaV wild-type (Panel E). Leaves co-infiltrated with CTV-GFP and CYVaV wild-type or CYVaV with a different CTV genome-targeting hairpin (Panel H) showed significant reductions in CTV-GFP at 6 days post-infiltration (Panel G).
Figure 27:
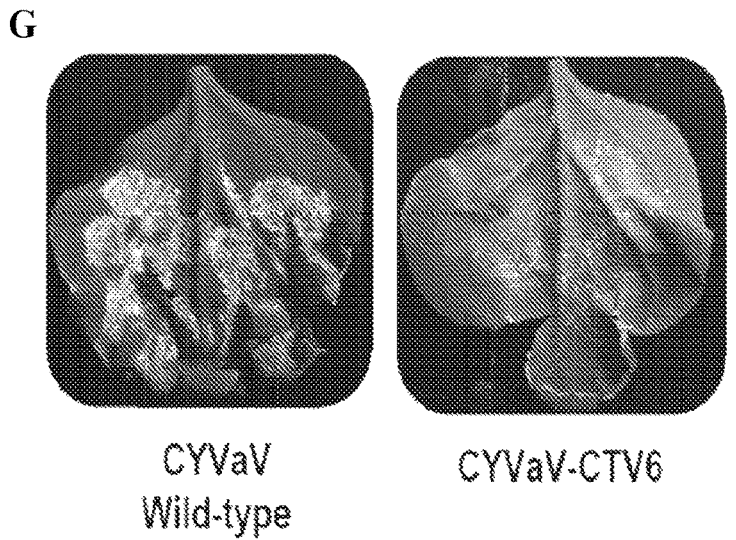

An iRNA-based virus-induced gene-silencing (VIGS) vector (the acronym VIGS being used herein for convenience, although the iRNA is not necessarily a virus) is provided that effectively targets host gene expression. An CYVaV-based vector was constructed that included a hairpin that targets green fluorescent protein (GFP) mRNA expressed in *N. benthamiana* 16C plants. The hairpin sequence (SEQ ID NO:37: FIG. 27, Panel B) targeting GFP was inserted and tested separately in two positions: 2301 and 2250. In the *N. benthamiana* 16C plants, GFP is expressed in every cell from the strongest plant promoter available (cauliflower mosaic virus 35S (CaMV 35S) promoter with a double enhancer). This is far more mRNA that needs to be targeted than any natural host mRNA.

In a normal, non-infected leaf without a gene for GFP (FIG. 26, Panel A), chloroplasts fluoresce bright red when observed under ultraviolet light (shown as dark grey in Panel A). In comparison, a leaf expressing relatively high levels of GFP (FIG. 26, Panel B), appeared dull orange with green stems in coloration under UV light (shown as lighter grey in Panel B).

Leaves expressing GFP were infected with the constructed iRNA-based VIGS vector including the GFP-suppressing hairpin at position 2301 (CYVaV-GFPhp$_{2301}$). The infected leaves demonstrated effective gene silencing (FIG. 26, Panel C). siRNAs targeted and silenced GFP mRNA first in the phloem, as readily apparent from leaf vasculature (FIG. 26. Panel C). As the VIGS construct migrated throughout the plant (FIG. 26, Panel D), siRNAs responsible for GFP gene silencing in turn were distributed throughout the leaves and plant over time, and continued to silence the target gene in all cells. GFP was significantly reduced, first in phloem (visible as bright red fluorescence in leaf veins under UV light; shown in Panel C as dark grey vein coloration). As the VIGS construct continued to migrate throughout the plant, gene suppression continued throughout the entire leaf and plant structures (visible as bright red fluorescence of entire leaves, as well as bright red coloration of younger leaves and all new leaves; shown in Panel D as dark grey coloration). Note that the same leaf in Panel C is also identified in Panel D (identified by white arrows in Panels C and D), and appeared almost completely red when observed under UV light.

Figure 26:
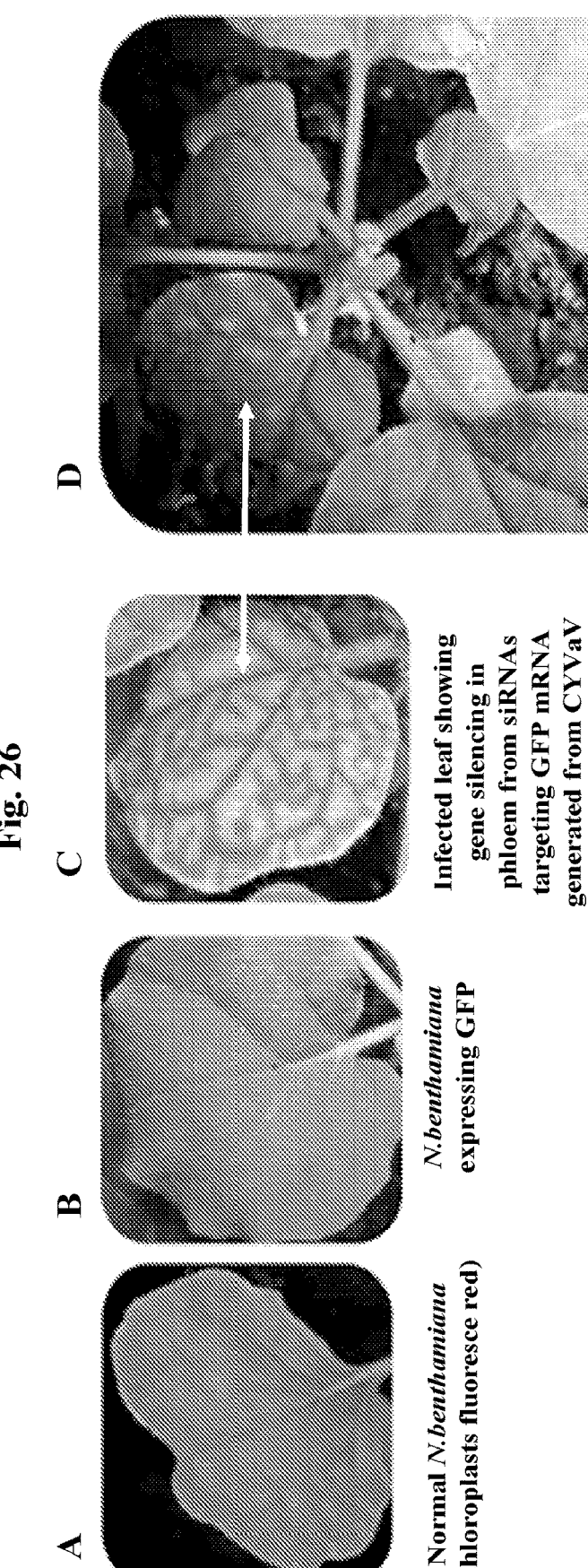
FIG. 26 illustrates a CYVaV VIGS construct that targets host gene expression. A normal, non-infected leaf without an gene for GFP is shown in Panel A, wherein chloroplasts fluoresced bright red when observed under ultraviolet light (shown as dark grey in Panel A). A leaf expressing GFP is shown in Panel B, and appeared dull orange with green stems in coloration under UV light (shown as lighter grey in Panel B). A leaf expressing GFP and infected with an exemplary VIGS construct is shown in Panel C, wherein infected leaves demonstrated effective gene silencing with siRNAs targeting and silencing GFP mRNA via the phloem in leaf vasculature. As shown in Panel D, after 14 days the VIGS construct migrated throughout the host plant (including the leaf shown in Panel C, identified by arrows), wherein siRNAs responsible for GFP gene silencing were distributed throughout the leaves and plant.

Thus, gene silencing effectively spread throughout much of the entire host plant over time (see FIG. 26, Panel D, image taken 14 days after infection with CYVaV-GFPhp$_{2301}$). Similar results were obtained by infecting leaves expressing GFP with the VIGS construct including the same GFP-suppressing hairpin (FIG. 27, Panel B) at position 2250 (CYVaV-GFPhp$_{2250}$).

CYVaV-Based Vector Targeting Expression of Callose Synthase.

A vector comprising an RNA insert is provided that triggers the reduction of callose production and build-up in a host tree. A sufficiently large amount of the gene that produces callose in the phloem in response to bacteria is silenced via insertion of an siRNA sequence that is excised by the plant.

CYVaV-based vector may be utilized as a virus-induced gene-silencing (VIGS) vector to down-regulate expression of callose synthase in the phloem. VIGS has been widely used to down-regulate gene expression in mature plants to examine plant functional genomics (Senthil-Kumar et al. (2008). Virus-induced gene silencing and its application in characterizing genes involved in water-deficit-stress tolerance. J Plant Physiol 165(13): 1404-1421). A complementary sequence is inserted into CYVaV at a suitable location as identified above (either anti-sense or a RNase III-cleavable hairpin). A citrus version of the gene is known (Enrique et al. (2011). Novel demonstration of RNAi in citrus reveals importance of citrus callose synthase in defense against *Xanthomonas citri* subsp. *citri*. Plant Biotech J 9:394-407).

Callose is a ß 1,3-glucan that is synthesized in various tissues during development and biotic and abiotic stress (Chen, X. Y. and Kim, J. Y. (2009). Callose synthesis in higher plants. Plant Sig Behav 4(6):489-492). Deposition of callose in the sieve plates of sieve elements inhibits photoassimilate flow in the phloem, leading to over accumulation of starch in source (young) leaves, which contributes to the death of trees during bacterial infections such as HLB. All plants contain 12-14 callose synthase genes; one member of this gene family, CalS7 (*Arabidopsis* nomenclature), is mostly responsible for rapid callose deposition in sieve pores of the phloem in response to wounding and various pathogens (Xie et al. (2011). CalS7 encodes a callose synthase responsible for callose deposition in the phloem. Plant J 65(1): 1-14). Complete inhibition of GSL7 impacted both normal phloem transport and inflorescence development in *Arabidopsis* (Barratt et al. (2011). Callose Synthase GSL7 Is Necessary for Normal Phloem Transport and Inflorescence Growth in *Arabidopsis*. Plant Physiol 155(1):328-341). A CYVaV-based vector is utilized to down-regulate the *N. benthamiana* and orange tree orthologues of CalS7 in mature plants in order to investigate the consequences of reduced (but not eliminated) sieve plate callose deposition. Alternatively, or in addition, the vector provides for an insert that expresses a callose-degrading enzyme.

iRNA-Based Vector Targeting CTV

An iRNA-based VIGS vector was constructed that targets CTV. As demonstrated by the data, disclosed constructs may be utilized for immunization as well as reduction of virus levels in host plants with mature infections. *N. benthamiana* infected with CTV-GFP (CTV expressing GFP) was used as root stock grafted to wild-type CYVaV (CYVaVwt) and CYVaV-GFPhp$_{2301}$ scions (FIG. 27, Panel A). The hairpin targeting GFP (FIG. 27, Panel B) was inserted at position 2301 in the construct (CYVaV-GFPhp2301). The sequence shown in FIG. 27, Panel B, is presented below:

(SEQ ID NO: 37)
ugaagcggcacgacuucuucaagagcgccagaauucuggcgcucuugaa
gaagucgugccgcuuca partially or nearly fully absent of GFP flecks (FIG. 27, Panel C, right image). RT-PCR of the red and green regions in the leave absent of GFP flecks (FIG. 27, Panel C, circled areas 'A' and 'B') showed that high levels of CYVaV-GFPhp$_{2301}$ correlated with red fluorescence (region A), with this tissue having between 3,000-fold and 440,000-fold less CTV compared to green region (region B). In particular, relative levels of CTV in region A were $4.4\times10^5$ fold lower as compared to CTV levels in region B. In addition, relative levels of CYVaV-GFPhp$_{2301}$ in region A were 2.3 times greater than CYVaV-GFPhp$_{2301}$ levels in region B (FIG. 27, Panel D).

As noted above, CTV is composed of two capsid proteins and with a genome of more than 19 kb. 76 CTV isolates have been characterized, which all contain regions of conserved nucleotides. Two sequence portions (18 and 6) of a CTV isolate are identified in Table 1 below, showing fully conserved polynucleotides (underlined below) as well as less-conserved nucleotides (in bold) with other nucleotides present in some isolates (listed as identified and bolded nucleotides in each sequence from left to right). For example, in the sequence portion for CTV18 shown in Table 1, the 3 non-conserved nucleotides include, from left to right: guanine (G) which position instead includes adenine (A) in 10 CTV isolates: cytosine (C) which position instead includes uracil (U) in about half of the CTV isolates; and G which position instead includes A in 6 CTV isolates. In the sequence portion for CTV6, the 6 non-conserved nucleotides include, from left to right: G which position instead includes A in 1 CTV isolate: G which position instead includes A in 3 CTV isolates; U which position instead includes C in 3 CTV isolates: A which position instead includes G in 9 CTV isolates: U which position instead includes C in 1 CTV isolate; and A which position instead includes G in 1 CTV isolate.

TABLE 1

Sequence Portions of CTV Isolates.

| # | CTV Position | Sequence (conserved nucleotides in known CTV isolates underlined): | Non-conserved nucleotides (bolded in sequence): |
|---|---|---|---|
| 18 | 15173 | UCCGUGGACGUCAUGUGUAAG (SEQ ID NO: 66) | G: A in 10 isolates<br>C: U in ~half isolates<br>G: A in 6 isolates |
| 6 | 17856 | GGAAGUGAUGGACGAAAUUAAUGA (SEQ ID NO: 67) | G: A in 1 isolate<br>G: A in 3 isolates<br>U: C in 3 isolates<br>A: G in 9 isolates<br>U: C in 1 isolate<br>A: G in 1 isolate |

The CYVaV-GFPhp$_{2301}$ hairpin targeted the GFP ORF of CTV, thereby cleaving CTV. In contrast, the CYVaVwt scion had no effect on CTV-GFP infecting newly emerging rootstock leaves, as evidenced by green fluorescent flecks visible under UV light in the young leaves (FIG. 27, Panel A, center image). However, green flecks were absent in stipules when CYVaV-GFPhp$_{2301}$ was present in the scion (FIG. 27, Panel A, right image), demonstrating that movement of CYVaV-GFPhp$_{2301}$ down into the root stock inhibited progression of the CTV infection.

When WT CYVaV was present in the root stock, new leaves from the CTV-GFP scion still fluoresced green under UV light, thus showing that widespread CTV infection continuing unabated (FIG. 27, Panel C, middle image). However, when CYVaV-GFPhp$_{2301}$ was in the root stock, the upper leaves in all CTV-GFP-infected scions were either Fully CTV-infected *N benthamiana* were agroinfiltrated with CYVaV-based vector carrying a hairpin at position 2301 that targeted a conserved sequence in the CTV genome (SEQ ID NO:38; FIG. 27, Panel F). The CYVaV-CTV18 hairpin contained a polynucleotide sequence (SEQ ID NO:39; identified in the dashed line box, Panel F) complementary to a corresponding sequence of CTV18 in all of its variants. The sequences identified in FIG. 27, Panel F, are identified below:

(SEQ ID NO: 38)
uccguggacgucauguguaaggguacccuuacacaugacguccacgga (SEQ ID NO: 39)
cuuacacaugacguccacgga After four days, CTV levels in plants infected with the CYVaV-CTV18 vector were about 10-fold lower in the infiltrated tissue as compared with tissue infiltrated with CYVaV wild-type (FIG. 27, Panel E).

Leaves co-infiltrated with CTV-GFP and CYVaV wild-type or CYVaV-CTV6 containing another CTV genome-targeting hairpin (SEQ ID NO:40; FIG. 27, Panel H) also showed significant reductions in CTV-GFP at 6 days post-infiltration (FIG. 27, Panel G). The CYVaV-CTV6 hairpin contained a polynucleotide sequence (SEQ ID NO:41; identified in the dashed line box, Panel H) that is complementary to a corresponding sequence of CTV6 in all of its variants. The sequences identified in FIG. 27, Panel H, are identified below:

```
                                         (SEQ ID NO: 40)
ggaagugauggacgaaauuaaugaccaaucauuaauuucguccaucacu
uccag (SEQ ID NO: 41)
ucauuaauuucguccaucacuucc
```

CTV levels in plants infected with the CYVaV-CTV6 vector were visibly lower in infiltrated tissue as compared with tissue infiltrated with CYVaV wt.

Stability of Hairpin Targeting GFP without and with L&D

The stability of a 30 nt hairpin targeting GFP (SEQ ID NO:49: FIG. 32, Panel E) was evaluated when inserted at position 2301 without any lock and dock structure (CY2301GFP30) and with L&D1 (CY2301 LDIGPF30s).

*N. benthamiana* 16C plant infected with CYVaV with the 30 nt hairpin insert at position 2301 (CY2301GFP30s) is shown in FIG. 32, Panel A. Virus-induced gene silencing (VIGS) effect was not detected. Sequence alignment between input CYVaV (CY2301GFP30) and the CYVaV accumulating in systemic tissue is shown in FIG. 32, Panel B. The later CYVaV contains a 19 nt deletion acquired during infection showing the construct was not stable. The sequences identified in FIG. 32, Panel B, are shown below:

```
                                         (SEQ ID NO: 44)
Agttaatgtaggtgtctttcctgaagcggcacgacttcttcaagagcgc
cagtatctagt (SEQ ID NO: 45)
agttaatgtaggtgtctttcctgaagcggc (SEQ ID NO: 46)
cagtatctagt
```

*N. benthamiana* 16C plant infected with CYVaV with L&D1 and the 30 nt hairpin insert (SEQ ID NO:49) at position 2301 (CY2301 LD1GFP30s) is shown in FIG. 32, Panel C. Obvious GFP silencing (plant fluorescing red, shown as darker gray in Panel C) by the VIGS vector was observed. Sequence alignment between CY2301LD1GFP30s infected plant and the original construct is shown in FIG. 32, Panel D. As shown, L&D1 substantially enhanced stability of the 30 nt hairpin insert. The sequences shown in FIG. 32, Panels D and E, are shown below:

```
                                         (SEQ ID NO: 47)
agttaatgtaggtgtctttccgcgatatggattcagggacttgaagcgg
cacgacttcttcaagagcgccaagtccctgctcaggggaaactttgtgt
cctaagtcgcgtatctagtcac
```

```
                                         (SEQ ID NO: 48)
agttaatgtaggtgtctttccgcgatatggattcagggacttgaagcgg
cacgacttcttcaagagcgccaagtccctgctcaggggaaactttgtgt
cctaagtcgcgtatctagtcac (SEQ ID NO: 49)
ugaagcggcacgacuucuucaagagcgcca
```

Stability of L&D1 and L&D1+Hairpin Targeting Callose Synthase

The stability of L&D1 inserted at position 2250 (CYm2250LD1), and of L&D1+a 30 nt hairpin (SEQ ID NO:59; FIG. 33, Panel E) targeting Callose Synthase (CYm2250LD1Cal_30 as), were evaluated.

*N. benthamiana* plant infected by CYm2250LD1 is shown in FIG. 33, Panel A, which contains L&D1 at the end of a truncated hairpin. The addition of these inserts at the end of the complete wild-type hairpin (at position 2250) were not found to be stable. Sequencing alignment (FIG. 33, Panel B) between CYm2250LD1 in infected tissue (RT-PCR) and the original construct shows complete stability. The sequences shown in FIG. 33, Panel B, are shown below:

```
                                         (SEQ ID NO: 50)
tgatacctgttcagaataggattgctcgagcttcgttggttagggtaac
tca (SEQ ID NO: 51)
gcgatatggattcagggactagtccctgctcaggggaaactttgtgtcc
taagtcgcac (SEQ ID NO: 52)
ctaaccagt (SEQ ID NO: 53)
aatagggtcattggtttaccgatgatacctgttcagaataggattgctc gagcttcgttggttagggtaactcacataccttcttccatagcgatatg gattcagggactagtccctgctcaggggaaactttgtgtcctaagtcgc actggaaaaggtcgtgtgagcaacctaaccagt
```

*N. benthamiana* 16C plant infected by CYm2250LD1asCal7_30 as (CYVaV containing L&D1 with the 30 nt insert (SEQ ID NO:59) targeting Callose Synthase is shown in FIG. 33, Panel C. Sequence alignment (FIG. 33, Panel D) between CYm2250LD1Cal730as accumulating in the infected plant (RT-PCR) and the original construct showing that the 30 nt insert was stable within L&D1. The 30 nt Callose synthase 7 siRNA sequence (antisense orientation) that targets the Callose Synthase that is active in phloem is shown in FIG. 33, Panel E. The sequences shown in FIG. 33, Panels D and E, are shown below:

```
                                         (SEQ ID NO: 54)
gatacctgttcagaataggattgctcgagcttcgttggttagggtaact
ca (SEQ ID NO: 55)
gcgatatggattcagggacttgatgttggatccatcctatgagcctttt
cagtccctgctcaggggaaactttgtgtcctaagtcgcac (SEQ ID NO: 56)
ctaaccagttaatgtaggtgtctttccgtatctagtcac (SEQ ID NO: 57)
aatagggtcattggtttaccgatgatacctgttcagaataggattgctc
gagcttcgttggttagggtaactcacataccttcttccatagcgatatg
gattcagggact
```

-continued

```
                                            (SEQ ID NO: 58)
agtccctgctcaggggaaactttgtgtcctaagtcgcactggaaaaggt cgtgtgagcaacctaaccagttaatgtaggtgtctttccgtatctagtc ac
```

```
                                            (SEQ ID NO: 59)
ugauguuggauccauccuaugagccuuuuc
```

In some examples, iRNA with a truncated hairpin (of the iRNA) and an insert have been stable over long test periods, for example over 40 days. Without intending to be limited by theory, truncating a hairpin of the iRNA (e.g., CYVaV), for example a structurally required hairpin, in combination with adding an insert to the hairpin of the iRNA results in the hairpin of the iRNA resembling its original size and/or retaining its structural integrity. It should be understood however, that the inserted hairpin or unstructured short RNA sequence need not be the same or similar size to truncated hairpin.

iRNA-Based Vector Containing Multiple Inserts

An iRNA-based vector was constructed that includes an insert at position 2301 and another insert at position 2330 (CY2301LD2/2330CTV6sh). The insert at position 2330 is a hairpin targeting CTV6 (SEQ ID NO:60) and the other insert at position 2301 is an empty L&D2 structure (SEQ ID NO:43; FIG. 34, Panel A). The sequences shown in FIG. 34, Panel A, are shown below:

```
                                            (SEQ ID NO: 43)
gcgauauggaucaggacuaguccugucacccucacuucggguguccaggg gaaacuuugugggugaguccuaagucgc
```

```
                                            (SEQ ID NO: 60)
ggaagugauggacgaaauuaaugaccaaucauuaauuucguccaucacu ucc
```

*N. benthamiana* infected with CY2301LD2/2330CTV6sh is shown in FIG. 34, Panel B. RT-PCR result from CY2301LD2/2330CTV6sh-infected plant is shown in FIG. 34, Panel C. The top band had both inserts and was the same as the original infiltrated construct. The lower band has a deletion in L&D2. The data show that two inserts were tolerated and the construct was infectious.

Enhanced Stability Lock and Dock Structure

Extending base-pairing at the base of the disclosed lock and dock structures improved stability of larger unstructured inserts. Base-pairing was extended in L&D1 to include three additional base pairs (G-C, C-G, G-C) (FIG. 35, Panel C) thereby resulting in a third lock and dock structure (L&D3). The sequence of L&D3 is provided below:

```
                                            (SEQ ID NO: 61)
gcggcgauauggauucagggacuagucccugcucaggggaaacuuugug uccuaagucgccgc
```

*N. benthamiana* plant infected with L&D3 at position 2301 (CY2301LD3) is shown in FIG. 35, Panel A. RT-PCR from the symptomatic leaf of infected plant showing a single band (no obvious deletions) is shown in FIG. 35, Panel B. Sequence alignment (FIG. 35, Panel D) of CYVaV with L&D1 in position 2301 and with RT-PCR sequencing of CY2301LD3 from infected plant tissue is shown. No instability was detected. The sequences shown in FIG. 35, Panel C, are shown below:

```
                                            (SEQ ID NO: 62)
tgtaggtgtctttccgcgatatggattcagggactagtccctgctcagg ggaaactttgtgtcctaagtcgcgtatctagtcacgatgg
```

```
                                            (SEQ ID NO: 63)
ttccataactggaaaaggtcgtgtgagcaacctaaccagttaatgtagg tgtctttccgcggcgatatggattcagggactagtccctgctcagggga aactttgtgtcctaagtcgccgcgtatctagtcacgatggtaagcaacc cgtttatctgtacggcgctcacccgtgggtaga
```

In some embodiments, an insert is provided that targets one or more viral and/or fungal and/or bacterial pathogens. In some embodiments, a hairpin or short RNA sequence (about 100 nt or less, e.g. between about 20 nt and about 80 nt, or between about 30 nt and about 60 nt, or about 30 nt) insert is provided that generates an siRNA that directly targets CVEV, since CVEV is known to slightly intensify the yellowing impacts of CYVaV and to enable transport of CYVaV between trees. In some embodiments, a hairpin insert is provided that targets CTV, since CTV is a highly destructive viral pathogen of citrus (second only to CLas). In other embodiments, an insert is provided that targets another citrus (or other) virus. In some embodiments, an insert is provided that targets a fungal pathogen(s), given that such pathogen(s) are able to take up siRNAs from the phloem. In some embodiments, an insert is provided that targets a bacterial pathogen, given that such pathogen(s) are able to take up siRNAs from the phloem.

In some embodiments, the CYVaV-based (or other iRNA) vector includes an insert(s) engineered to modify a phenotypic property of a plant that emanates from gene expression in companion cells. In one implantation, an insert is provided that triggers dwarfism, so that the fruit is easier to harvest and growth space requirements are reduced. Additional and/or other traits may also be targeted as desired. The iRNA vectors of the present disclosure comprising 1, 2, 3 or more inserts demonstrate stability and functionality.

In some embodiments, an RNA vector is the same as, essentially the same as, or substantially similar to, an RNA vector that is produced by a method described herein but made differently, for example, by a synthetic manufacturing method that might or might not pass through an equivalent of a wild type or parental form. For example, rather than actually truncating or stabilizing a wild type RNA vector, an RNA may be manufactured synthetically that has the same nucleic acid sequence as a truncated or stabilized wild type RNA vector. In this case, it may not be necessary to manufacture the full wild type vector and then truncate or stabilize it but rather the truncated or stabilized structure can be manufactured directly. Similarly, it is not necessary to produce an RNA backbone and then add a heterologous insert to the RNA backbone. Instead, an RNA vector may be manufactured directly with the insert present. Thus descriptions of actions or states based on verbs such as to insert, to truncate, or to stabilize, or referring to starting from parental or wild type structures, should be interpreted notionally so as to include a resulting nucleic acid sequence whether that action was actually performed or not and whether the specified starting material was actually used or not. For example, an optionally truncated or stabilized parental structure with an added heterologous element may instead be made by determining its nucleic acid sequence and synthetically manufacturing an equivalent or similar molecule was created by some other sequence of steps or method.

All identified publications and references mentioned in this specification are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. An RNA vector derived from citrus yellow vein associated virus (CYVaV) consisting essentially of the nucleic acid sequence of SEQ ID NO: 1 and one or more heterologous segment(s) at position 2250, 2301, 2319, 2330, 2331, 2336, 2375 or 2083 of SEQ ID NO:1.

2. The RNA vector of claim 1, wherein the CYVaV based RNA comprises stabilizing changes.

3. The RNA vector of claim 2, wherein the CYVaV based RNA comprises changes converting G: U pairs to G: C pairs in the 3'UTR structure.

4. The RNA vector of claim 1 wherein the heterologous segment(s) comprise a sequence complementary to a sequence within Citrus tristeza virus (CTV).

5. The RNA vector of claim 4, wherein the sequence within CTV is conserved in multiple CTV strains.

6. A plant comprising a sour orange rootstock and the RNA vector of claim 4.

7. The plant of claim 6, wherein said heterologous segment(s) comprises a sequence conserved in multiple CTV strains.

8. The RNA vector of claim 1, which is capable of systemic and phloem-limited movement and replication within a host plant.

* * * * *